US012559481B2

(12) United States Patent
Huebsch et al.

(10) Patent No.: US 12,559,481 B2
(45) Date of Patent: Feb. 24, 2026

(54) QUINOLINE DERIVATIVES

(71) Applicant: ELANCO ANIMAL HEALTH GMBH, Monheim Am Rhein (DE)

(72) Inventors: Walter Huebsch, Wuppertal (DE); Nils Griebenow, Dormagen (DE); Hans-Georg Schwarz, Dorsten (DE); Daniel Kulke, Leverkusen (DE); Claudia Boehm, Hannover (DE); Kirsten Boerngen, Cologne (DE); Bernd Alig, Koenigswinter (DE); Wei Zhuang, Monheim am Rhein (DE); Iring Heisler, Duesseldorf (DE); Thomas Ilg, Monheim am Rhein (DE); Johannes Koebberling, Neuss (DE); Adeline Koehler, Langenfeld (DE); Niels Lindner, Wuppertal (DE); Ulrich Goergens, Ratingen (DE); Claudia Welz, Dusseldorf (DE); Maike Hink, Vaihingen/Enz (DE)

(73) Assignee: Elanco Animal Health GmbH, Monheim am Rhein (DE)

( * ) Notice: Subject to any disclaimer, the term of this patent is extended or adjusted under 35 U.S.C. 154(b) by 0 days.

(21) Appl. No.: 18/063,766

(22) Filed: Dec. 9, 2022

(65) Prior Publication Data

US 2023/0141809 A1 May 11, 2023

Related U.S. Application Data

(63) Continuation of application No. 17/053,680, filed as application No. PCT/EP2019/061725 on May 7, 2019, now Pat. No. 11,572,357.

(30) Foreign Application Priority Data

May 9, 2018 (EP) .................................... 18171490

(51) Int. Cl.
*C07D 405/14* (2006.01)
*A61P 33/10* (2006.01)
*C07D 405/12* (2006.01)

(52) U.S. Cl.
CPC ............ *C07D 405/14* (2013.01); *A61P 33/10* (2018.01); *C07D 405/12* (2013.01)

(58) Field of Classification Search
None
See application file for complete search history.

(56) References Cited

U.S. PATENT DOCUMENTS

| | | | |
|---|---|---|---|
| 4,343,804 | A | 8/1982 | Munson et al. |
| 4,870,082 | A | 9/1989 | Rector et al. |
| 7,354,934 | B2 | 4/2008 | Bridger et al. |
| 7,872,036 | B2 | 1/2011 | Toriyabe |
| 7,977,349 | B2 | 7/2011 | Fuerstner et al. |
| 8,536,340 | B2 | 9/2013 | Hamamoto |
| 8,697,867 | B2 | 4/2014 | Hamamoto |
| 8,946,234 | B2 | 2/2015 | Maue |
| 8,980,912 | B2 | 3/2015 | Hamamoto |
| 9,580,405 | B2 | 2/2017 | Yang |
| 9,591,857 | B2 | 3/2017 | Buysse |
| 9,717,242 | B2 | 8/2017 | Kagabu |
| 9,750,252 | B2 | 9/2017 | Satoh |
| 9,938,292 | B2 | 4/2018 | Wu |
| 10,889,573 | B2 | 1/2021 | Huebsch et al. |
| 2008/0306048 | A1 | 12/2008 | Kaplan |
| 2013/0210844 | A1 | 8/2013 | Gharat |
| 2014/0213448 | A1 | 7/2014 | Buysse |
| 2014/0275503 | A1 | 9/2014 | Giampietro |

(Continued)

FOREIGN PATENT DOCUMENTS

| | | | |
|---|---|---|---|
| CN | 101715774 | A | 6/2010 |
| CN | 101337937 | B | 12/2010 |

(Continued)

OTHER PUBLICATIONS

International Search Report of International Patent Application No. PCT/EP2019/061725, mailed Jul. 16, 2019.

(Continued)

*Primary Examiner* — Adam C Milligan
*Assistant Examiner* — Jed A Kucharczk
(74) *Attorney, Agent, or Firm* — McBee Moore & Vanik IP, LLC

(57) ABSTRACT

The present invention covers new quinoline compounds of general formula (I):

(I)

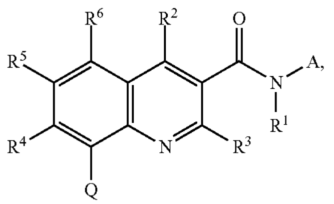

in which A, $R^1$, $R^2$, $R^3$, $R^4$, $R^5$, $R^6$, and Q are as defined herein, methods of preparing said compounds, intermediate compounds useful for preparing said compounds, pharmaceutical compositions and combinations comprising said compounds and the use of said compounds for manufacturing pharmaceutical compositions for the treatment, control and/or prevention of diseases, in particular of helminth infections, as a sole agent or in combination with other active ingredients.

18 Claims, No Drawings

(56) References Cited

U.S. PATENT DOCUMENTS

| | | | |
|---|---|---|---|
| 2018/0014543 | A1 | 1/2018 | Kai |
| 2020/0024264 | A1 | 1/2020 | Huebsch et al. |
| 2021/0115026 | A1 | 4/2021 | Huebsch et al. |

FOREIGN PATENT DOCUMENTS

| | | | |
|---|---|---|---|
| CN | 102391261 | A | 3/2012 |
| CN | 101337940 | B | 5/2012 |
| CN | 103265527 | B | 8/2014 |
| CN | 103109816 | B | 9/2014 |
| CN | 103232431 | B | 11/2014 |
| CN | 103524422 | B | 5/2015 |
| DE | 3639877 | A1 | 5/1988 |
| EP | 0263209 | A2 | 4/1988 |
| EP | 0326331 | A2 | 8/1989 |
| EP | 0523512 | A1 | 1/1993 |
| EP | 2647626 | A1 | 10/2013 |
| IL | 266407 | A | 10/2021 |
| JP | S62502469 | A | 9/1987 |
| JP | 2008214323 | A | 9/2008 |
| JP | 2010018586 | A | 1/2010 |
| RU | 2325387 | C2 | 5/2008 |
| RU | 2433125 | C2 | 11/2011 |
| WO | 8605982 | A2 | 10/1986 |
| WO | 2002004444 | A2 | 1/2002 |
| WO | 2003106457 | A1 | 12/2003 |
| WO | 2004099160 | A1 | 11/2004 |
| WO | 2005037826 | A1 | 4/2005 |
| WO | 2006003494 | A2 | 1/2006 |
| WO | 2006043635 | A1 | 4/2006 |
| WO | 2006103120 | A2 | 10/2006 |
| WO | 2007040280 | A1 | 4/2007 |
| WO | 2007040282 | A1 | 4/2007 |
| WO | 2010052161 | A2 | 5/2010 |
| WO | 2010066780 | A1 | 6/2010 |
| WO | 2011085575 | A1 | 7/2011 |
| WO | 2011105506 | A1 | 9/2011 |
| WO | 2011151146 | A1 | 12/2011 |
| WO | 2012029672 | A1 | 3/2012 |
| WO | 2012034403 | A1 | 3/2012 |
| WO | 2012112363 | A1 | 8/2012 |
| WO | 2013050317 | A1 | 4/2013 |
| WO | 2013064465 | A1 | 5/2013 |
| WO | 2013096151 | A1 | 6/2013 |
| WO | 2013115391 | A1 | 8/2013 |
| WO | 2013118071 | A1 | 8/2013 |
| WO | 2013144213 | A1 | 10/2013 |
| WO | 2013162715 | A2 | 10/2013 |
| WO | 2013162716 | A2 | 10/2013 |
| WO | 2013174780 | A1 | 11/2013 |
| WO | 2014187846 | A1 | 11/2014 |
| WO | 2015058021 | A1 | 4/2015 |
| WO | 2015058028 | A1 | 4/2015 |
| WO | 2015078800 | A1 | 6/2015 |
| WO | 2015144001 | A1 | 10/2015 |
| WO | 2016005276 | A1 | 1/2016 |
| WO | 2016133011 | A1 | 8/2016 |
| WO | 2017103851 | A1 | 6/2017 |
| WO | 2017178416 | A1 | 10/2017 |
| WO | 2018087036 | A1 | 5/2018 |
| WO | 2010051926 | A2 | 5/2020 |

OTHER PUBLICATIONS

Hogantharanni Govender et al., "Synthesis and Bioactivity of Quinoline-3-carboxamide Derivatives", J. Heterocyclic Chem., 2018, https://doi.org/10.1002/jhet.3132, pp. 1002-1009 , vol. 55.

Exhibit A, "Biology—Life Cycle of D. immitis", Life cycle image and information courtesy of DPDx., Feb. 8, 2012, 2 pages.

Baumgarten, H.E. et al. "Naphthyridines. IV. Synthesis of Benzo[f]-1-7-naphthyridines (1,2)," J. Heterocyclic Chem, 18: 925-928, 1981.

Berge, S. "Pharmaceutical Salts," Journal of Pharmaceutical Sciences; 66(1):1-19, Jan. 1977.

Blad, C.C. et al. "Novel 3,6,7-Subsituted Pyrazolopyrimidines as Positive Allosteric Modulators for the Hydroxycarboxylic Acid Receptor 2 (GPR109A)," Journal of Medicinal Chemistry, 55: 3563-3567, 2012.

Bonnefous, C. et al. "Discovery of Inducible Nitric Oxide Synthase (iNOS) Inhibitor Development Candidate KD7332, Part 1: identification of a Novel, Potent, and Selective Series of Quinolinone iNOS Dimerization Inhibitors that are Orally Active in Rodent Pain Models," J. Med. Chem. 52: 3047-3062, 2009.

Cross et al. "International Union of Pure and Applied Chemistry: Organic Chemistry Division Commission on Nomenclature of Organic Chemistry" Pure & Appl. Chem. 45:11-30, 1976.

Djerassi, C. et al. "Brominations with Pyridine Hydrobromide Perbromide," J. Am. Chem. Soc., 70: 417-418, 1948.

T.W. Greene and P.G.M. Wuts in "Protective Groups in Organic Synthesis", 3rd edition, Wiley, 1999.

International Search Report mailed Jan. 4, 2018 for PCT Application No. PCT/EP2017/078319, filed Nov. 6, 2017, 6 pages, Nov. 6, 2017.

Kotha, S. et al. "Recent applications of the Suzuki-Miyaura cross-coupling reaction in organic synthesis," Tetrahedron 58: 9633-9695, 2002.

Lennox, A.J.J. et al. "Selection of boron reagents for Suzuki-Miyaura coupling," Chem. Soc. Rev. 43: 112-443, 2014.

Maltais, F. et al. "In Vitro and in Vivo Isotope Effects with Hepatitis C. Protease Inhibitors: Enhanced Plasma Exposure of Deuterated Telaprevir versus Telaprevir in Rats," J. Med. Chem.; 52(24):7993-8001, 2009.

Mehlhorn et al. Encyclopedia of Parasitology, 4th edition, Springer-Verlag, Berlin Heidelberg, 2016.

Mutlib, A. et al. "The Species-Dependent Metabolism of Efavirenz Produces a Nephrotoxic Glutathione Conjugate in Rats," Toxicology and Applied Pharmacology; 169;102-113, 2000.

Muller, S. et al. "Pyridostatin analogues promote telomere dysfunction and long-term growth inhibition in human cancer cells," Org. Biomol. Chem. 10: 6537-6546, 2012.

Ochiana, S.O. et al. "Repurposing Human PDE4 Inhibitors for Neglected Tropical Diseases. Evaluation of Analogs of the Human PDE4 Inhibitor GSK-256066 as Inhibitors of PDEB1 of Trypanosoma brucei," Chem. Biol. Drug Des. 85: 548-564, 2015.

Ohnmacht Jr., C.J. et al. "Antimalarials. 5. A-Dibutylaminomethyl-and a-(2-Piperidyl)-3-quinolinemethanols," Journal of Medicinal Chemistry 14: 17-24, 1971.

Perrin, C. et al. "Stereochemistry of B-Deuterium Isotope Effects on Amine Basicity," J. Am. Chem. Soc; 127 (26):9641-9647, 2005.

Perrin, C. et al. "Secondary Deuterium Isotope Effects on the Acidity of Carboxylic Acids and Phenols," J. Am. Chem. Soc.; 129(14):4490-4497, 2007.

Plevova, K. et al. "Building a library of monofluorinated anilinomethylidenes and spectroscopic studies of their properties," Monatsch Chem 146: 291-302, 2015.

Prier, C.K. et al. "Visible Light Photoredox Catalysis with Transition Metal Complexes: Applications in Organic Synthesis," Chem. Rev. 113:5322-5363, 2013.

Rosman, K. et al. Isotopic Compositions of the Elements 1997, Pure & Appl. Chem., 70(1): 217-235, 1998.

Schneider, F. et al. "Enhanced Plasma Concentration by Selective Deuteration of Rofocoxib in Rats," Arzneim .- Forsch./Drug Res.; 56(4):295-300, 2006.

Schroder, E. et al. "Non-steroidal anti-inflammatoires 4. (1) Substituted aza-napthylacetic acids with antiphlogistic effect," Eur. J. Med. Chem. 14(6): 499-506, 1979.

Sharma, A. et al. "Nevirapine Bioactivation and Covalent Binding in the Skin," Chem. Res. Toxicol.; 26:410-421, 2013.

Shaw, M.H. et al. "Photoredox Catalysis in Organic Chemistry," J. Org. Chem: 81: 6898-6926, 2016.

Tayar, N.E. et al. "The lipophilicity of deuterium atoms. A comparison of shake-flask and HPLC methods," Int. J. Pharm.; 19(3):271-281, 1984.

The Pesticide Manual, 16th Ed., British Crop Protection Council, 2012.

(56) References Cited

OTHER PUBLICATIONS

Wendeborn, S. et al. "A new synthesis of functionalized imidazole-2-ones," Tetahedron Letters 41: 6387-6391, 2000.
Wenthur, C. et al. "Discovery of (R)-(2-FLuoro-4-((-4methoxyphenyl)ethnyl)phenyl)(3-Hydroxypiperidin-1-yl) methanone (ML337), An mGlu3 Selective and CNS Penetrant Negative Allosteric Modulator (NAM)," J. Med. Chem.; 56: 5208-5212, 2013.
Wilkinson, J.H. "Some meso-Amino-acridines and -quinolines derived from 2-Aminodiphenyl," Chemical Society, 1950: 464-468, 1950.
Wood, A. "Compendium of Pesticide Common Names," located at http://www.alanwood.net/pesticides.
Zask, A. et al. "Synthesis and SAR of Bicyclic Heteroaryl Hydroxamic Acid MMP and TACE Inhibitors," Bioorganic & Medicinal Chemistry Letters 13: 1487-1490, 2003.
H Avedissian et al., "Cobalt-catalyzed alkenylation of zinc organometallics", Tetrahedron Letters, vol. 39, 1998, pp. 6163-6166.
Xiang et al., "Discovery and optimization of 1-(H-indol-1yl) enthanone derivatives as CBP/EP300 bromodomain inhibitors for the treatment of castration-resistant prostate cancer", European Journal of Medicinal Chemistry, vol. 147, 2018, pp. 238-252.
Klose et al., "2-Propanephosphonic acid anhydrive (T3P)-mediated segment coupling and head-to-tail cyclization of sterically hindered peptides", Chem. Commun., 1999, pp. 1847-1848.
Butters et al., "Process development of voriconazole: a novel broad-spectrum triazole anifungal agent", Org. Proc. Res. and Dev., vol. 5, 2001, pp. 28-36 (Abstract).

QUINOLINE DERIVATIVES

CROSS REFERENCE TO RELATED APPLICATIONS

This application is a continuation of U.S. application Ser. No. 17/053,680, filed 6 Nov. 2020, which is the National Stage entry of International Application No. PCT/EP2019/061725, filed 7 May 2019, which claims priority to European Patent Application No. 18171490.8, filed 9 May 2018, the content of each these applications is herein incorporated by reference in their entirety.

The present invention covers new quinoline derivatives of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the control, treatment and/or prevention of diseases, in particular for the control, treatment and/or prevention of infections with helminths, more particularly of infections with gastro-intestinal and extra-intestinal nematodes, in animals and humans, formulations containing such compounds and methods for the control, treatment and/or prevention of infections with helminths, more particularly of infections with gastro-intestinal and extra-intestinal nematodes, in animals and humans as a sole agent or in combination with other active ingredients.

BACKGROUND

The occurrence of resistances against all commercial anthelmintics seems to be a growing problem in the area of veterinary medicine. The extensive utilisation of anthelmintics to manage the control of nematodes resulted in significant selection of highly resistant worm populations. Therefore, the spread of resistance against all anthelmintic drug classes threatens effective worm control in cattle, goats, sheep and horses. Furthermore, successful prevention of heartworm disease in dogs, which currently solely relies on the utilisation of macrocyclic lactones, is in danger as loss of efficacy for multiple macrocyclic lactones has been described for some regions of the United States of America—especially in those areas where the bear worm challenge for infection is high. Finally, experimental infection studies with *Dirofilaria immitis* larvae from suspected field loss of efficacy cases in the Lower Mississippi Delta provided in vivo confirmation of the existence of macrocyclic lactone resistance.

Although resistance of human helminths against anthelmintics seems currently to be rare, the spread of anthelmintic resistance in the veterinary field as mentioned before needs to be considered in the treatment of human helminthosis as well. Persistent underdosed treatments against filariosis may lead to highly resistant genotypes and resistances have already been described for certain anthelmintics (e.g. praziquantel, benzimidazole and niclosamide).

Therefore, resistance-breaking anthelmintics with new molecular modes of action are urgently required.

It is an object of the present invention to provide compounds which can be used as anthelmintics in the medical, especially veterinary, field with a satisfactory or improved anthelmintic activity against a broad spectrum of helminths, particularly at relatively low dosages, for the control, treatment and/or prevention of infections with helminths in animals and humans, preferably without any adverse toxic effects to the treated organism.

Certain quinoline carboxamides are described in JP2008-214323A as agents suitable for treatment and/or prevention of skin diseases, like acne vulgaris, dermatitis or the like.

The WO2017103851 discloses quinoline-3-carboxamides as H-PGDS inhibitors, useful for treating atherosclerosis, psoriasis, sinusitis, and duchenne muscular dystrophy.

WO2018087036 discloses quinoline-3-carboxamides as anthelmintics in the medical especially veterinary field.

However, the state of the art does not describe the new quinoline derivatives of general formula (I) of the present invention as described and defined herein.

It has now been found, and this constitutes the basis of the present invention, that the compounds of the present invention have surprising and advantageous properties.

In particular, the compounds of the present invention have surprisingly been found to effectively interact with Slo-1 calcium-gated potassium channels of nematodes. This interaction is characterized by achieving paralysis/inhibition in particular of gastro-intestinal nematodes, of free-living nematodes, and of filariae, for which data are given in the biological experimental section. Therefore the compounds of the present invention may be used as anthelmintics for the control, treatment and/or prevention of gastro-intestinal and extra-intestinal helminth infections, in particular gastro-intestinal and extra-intestinal infections with nematodes, including filariae.

DESCRIPTION OF THE INVENTION

In accordance with a first aspect, the present invention covers compounds of general formula (I):

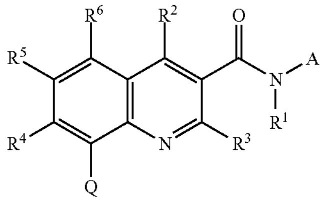

(I)

in which:

A is A1 or A2,

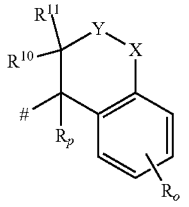

A1

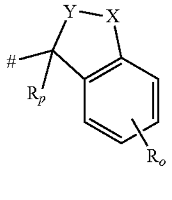

A2 is 0, 1, 2, 3 or 4,

R is selected from the group consisting of hydrogen, halogen, cyano, nitro, —OH, $C_1$-$C_4$-alkyl, $C_1$-$C_1$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, $R_p$ is selected from the group consisting of hydrogen, $C_1$-$C_4$-alkyl, X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—, $R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_4$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_3$-halogenoalkyl having 1 to 5 halogen atoms, $C_1$-$C_4$-alkoxy, $C_1$-$C_3$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of tetrahydro-2H-pyran-4-yl, 3,6-dihydro-2H-pyran-4-yl, ethyl and 3-fluoroazetidin-1-yl, $R^3$ is hydrogen or $C_1$-$C_4$-alkyl, $R^4$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, preferably hydrogen, halogen and $C_1$-$C_4$-alkoxy, more preferably fluorine, chlorine, methoxy and isopropoxy, $R^5$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, $R^6$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, $R^7$ is selected from the group consisting of hydrogen, —OH, fluorine, $C_1$-$C_4$-alkyl and $C_1$-$C_4$-alkoxy, $R^8$ is selected from the group consisting of hydrogen, —OH, fluorine, $C_1$-$C_4$-alkyl and $C_1$-$C_4$-alkoxy, or $R^7$ and $R^8$ together form an oxo group (=O), or $R^7$ and $R^8$ form, together with the carbon atom to which they are attached, a 3- to 6-membered ring selected from the group consisting of $C_3$-$C_6$-cycloalkyl and 3- to 6-membered heterocycloalkyl, $R^9$ is selected from the group consisting of hydrogen, $C_1$-$C_4$-alkyl, $C_3$-$C_4$-halogenoalkyl having 1 to 5 halogen atoms and $C_1$-$C_4$-alkoxy, $R^{10}$ is selected from the group consisting of hydrogen, —OH, $C_1$-$C_4$-alkyl and $C_1$-$C_4$-alkoxy, $R^{11}$ is selected from the group consisting of hydrogen, $C_1$-$C_4$-alkyl and $C_1$-$C_4$-alkoxy, or $R^{10}$ and $R^{11}$ form, together with the carbon atom to which they are attached, a 3- to 6-membered ring selected from the group consisting of $C_3$-$C_6$-cycloalkyl and 3- to 6-membered heterocycloalkyl, Q is 2,3,5-trifluorophenyl, wherein when Y is O, S or N—$R^9$, none of $R^7$, $R^8$, $R^{10}$ and $R^{11}$ is —OH or $C_1$-$C_4$-alkoxy, and wherein when X is O, S or N—$R^9$, none of $R^7$ and $R^8$ is —OH or $C_1$-$C_4$-alkoxy;

and wherein a compound according to the formula

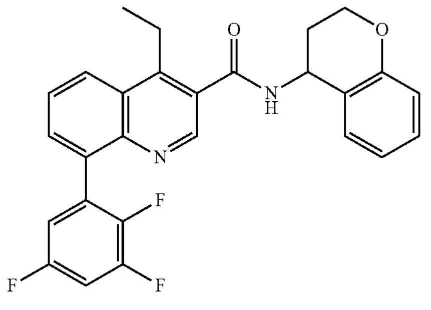 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

Should a composite substituent be composed of more than one parts, e.g. ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

As used herein, the position via which a respective substituent is connected to the rest of the molecule may in a drawn structure be depicted by a hash sign (#) or a dashed line in said substituent.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

The term "$C_1$-$C_6$-alkyl" means a linear or branched, saturated, monovalent hydrocarbon group having 1, 2, 3, 4, 5 or 6 carbon atoms. The term "$C_1$-$C_4$-alkyl" means a linear or branched, saturated, monovalent hydrocarbon group having 1, 2, 3, or 4 carbon atoms, e.g. a methyl, ethyl, n-propyl, isopropyl, n-butyl, sec-butyl, isobutyl or a tert-butyl group, or an isomer thereof. Particularly, said group has 1, 2 or 3 carbon atoms ("$C_1$-$C_3$-alkyl"), e.g. a methyl, ethyl, n-propyl or isopropyl group.

The term "$C_1$-$C_4$-hydroxyalkyl" means a linear or branched, saturated, monovalent hydrocarbon group in which the term "$C_1$-$C_4$-alkyl" is defined supra, and in which 1 or 2 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "—NH($C_1$-$C_4$-alkyl)" or "—N($C_1$-$C_4$-alkyl)$_2$" means a linear or branched, saturated, monovalent group in which the term "$C_1$-$C_4$-alkyl" is as defined supra, e.g. a methylamino, ethylamino, n-propylamino, isopropylamino, N,N-dimethylamino, N-methyl-N-ethylamino or N,N-diethylamino group.

The term "—S—$C_1$-$C_4$-alkyl", "—S(O)—$C_1$-$C_4$-alkyl" or "—$SO_2$—$C_1$-$C_4$-alkyl" means a linear or branched, saturated group in which the term "$C_1$-$C_4$-alkyl" is as defined supra, e.g. a methylsulfanyl, ethylsulfanyl, n-propylsulfanyl, isopropylsulfanyl, n-butylsulfanyl, sec-butylsulfanyl, isobutylsulfanyl or tert-butylsulfanyl group, a methylsulfinyl, ethylsulfinyl, n-propylsulfinyl, isopropylsulfinyl, n-butylsulfinyl, sec-butylsulfinyl, isobutylsulfinyl or tert-butylsulfinyl group, or a methylsulfonyl, ethylsulfonyl, n-propylsulfonyl, isopropylsulfonyl, in-butylsulfonyl, sec-butylsulfonyl, isobutylsulfonyl or tert-butylsulfonyl group.

The term "$C_1$-$C_4$-halogenoalkyl" means a linear or branched, saturated, monovalent hydrocarbon group in which the term "$C_1$-$C_4$-alkyl" is as defined supra, and in which one or more of the hydrogen atoms are replaced, identically or differently, with a halogen atom. Particularly, said halogen atom is a fluorine atom. More particularly, all said halogen atoms are fluorine atoms ("$C_1$-$C_4$-fluoroalkyl"). Said $C_1$-$C_4$-halogenoalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_4$-alkoxy" means a linear or branched, saturated, monovalent group of formula ($C_1$-$C_4$-alkyl)-O—, in which the term "$C_1$-$C_4$-alkyl" is as defined supra, e.g. a methoxy, ethoxy, n-propoxy, isopropoxy, n-butoxy, sec-butoxy, isobutoxy or tert-butoxy group, or an isomer thereof.

The term "$C_1$-$C_4$-halogenoalkoxy" means a linear or branched, saturated, monovalent $C_1$-$C_4$-alkoxy group, as defined supra, in which one or more of the hydrogen atoms is replaced, identically or differently, with a halogen atom. Particularly, said halogen atom is a fluorine atom. Said $C_1$-$C_4$-halogenoalkoxy group is, for example, fluoromethoxy, difluoromethoxy, trifluoromethoxy, 2,2,2-trifluoroethoxy or pentafluoroethoxy.

The term "$C_2$-$C_4$-alkenyl" means a linear or branched, monovalent hydrocarbon group, which contains one double bond, and which has 2, 3 or 4 carbon atoms. Said $C_2$-$C_4$-alkenyl group is, for example, an ethenyl (or "vinyl"), a prop-2-en-1-yl (or "allyl"), prop-1-en-1-yl, but-3-enyl, but-2-enyl, but-1-enyl, prop-1-en-2-yl (or "isopropenyl"), 2-methylprop-2-enyl, 1-methylprop-2-enyl, 2-methylprop-1-enyl or a 1-methylprop-1-enyl, group. Particularly, said group is allyl.

The term "$C_2$-$C_4$-alkynyl" means a linear monovalent hydrocarbon group which contains one triple bond, and which contains 2, 3 or 4 carbon atoms. Said $C_2$-$C_4$-alkynyl group is, for example, an ethynyl, a prop-1-ynyl, prop-2-ynyl (or "propargyl"), but-1-ynyl, but-2-ynyl, but-3-ynyl or 1-methylprop-2-ynyl, group. Particularly, said alkynyl group is prop-1-ynyl or prop-2-ynyl.

The term "$C_3$-$C_6$-cycloalkyl" means a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl group.

The term "$C_3$-$C_6$-halogenocycloalkyl" means a saturated, monovalent, monocyclic hydrocarbon ring in which the term "$C_3$-$C_6$-cycloalkyl" is as defined supra, and in which one or more of the hydrogen atoms are replaced, identically or differently, with a halogen atom. Particularly, said halogen atom is a fluorine or chlorine atom. Said $C_3$-$C_6$-halogenocycloalkyl group is for example, a monocyclic hydrocarbon ring substituted with one or two fluorine or chlorine atoms, e.g. a 1-fluoro-cyclopropyl, 2-fluorocyclopropyl, 2,2-difluorocyclopropyl, 2,3-difluorocyclopropyl, 1-chlorocyclopropyl, 2-chlorocyclopropyl, 2,2-dichlorocyclopropyl, 2,3-dichlorocyclopropyl, 2-fluoro-2-chlorocyclopropyl and 2-fluoro-3-chlorocyclopropyl group.

The term "benzo-$C_5$-$C_6$-cycloalkyl" means a monovalent, bicyclic hydrocarbon ring wherein a saturated, monovalent, monocyclic hydrocarbon ring which contains 5 or 6 carbon atoms ("$C_5$-$C_6$-cycloalkyl") is annelated to a phenyl ring. Said benzo-$C_5$-$C_6$-cycloalkyl group is for example, a bicyclic hydrocarbon ring, e.g. an indane (i.e. 2,3-dihydro-1H-indene) or tetraline (i.e. 1,2,3,4-tetrahydronaphthalene) group.

The term "spirocycloalkyl" means a saturated, monovalent bicyclic hydrocarbon group in which the two rings share one common ring carbon atom, and wherein said bicyclic hydrocarbon group contains 5, 6, 7, 8, 9, 10 or 11 carbon atoms, it being possible for said spirocycloalkyl group to be attached to the rest of the molecule via any one of the carbon atoms except the spiro carbon atom. Said spirocycloalkyl group is, for example, spiro[2.2]pentyl, spiro[2.3]hexyl, spiro[2.4]heptyl, spiro[2.5]octyl, spiro[2.6]nonyl, spiro[3.3]heptyl, spiro[3.4]octyl, spiro[3.5]nonyl, spiro[3.6]decyl, spiro[4.4]nonyl, spiro[4.5]decyl, spiro[4.6]undecyl or spiro[5.5]undecyl.

The term "heterocycloalkyl" means a monocyclic or bicyclic, saturated or partially saturated heterocycle with 4, 5, 6, 7, 8, 9 or 10 ring atoms in total (a "4- to 10-membered heterocycloalkyl" group), particularly 4, 5 or 6 ring atoms (a "4- to 6-membered heterocycloalkyl" group), which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, oxolanyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl, 1,3-thiazolidinyl or 1,2,4-triazolidinyl, for example; or a 6-membered ring, such as tetrahydropyranyl, tetrahydrothiopyranyl, piperidinyl, morpholinyl, dithianyl, thiomorpholinyl, piperazinyl, oxanyl, 1,3-dioxanyl, 1,4-dioxanyl or 1,2-oxazinanyl, for example; or a 7-membered ring, such as azepanyl, 1,4-diazepanyl or 1,4-oxazepanyl, for example; or a bicyclic 7-membered ring, such as 6-oxa-3-azabicyclo[3.1.1]heptan, for example; or a bicyclic 8-membered ring, such as 5,6-dihydro-4H-furo[2,3-c]pyrrole or 8-oxa-3-azabicyclo[3.2.1]octan, for example; or a bicyclic 9-membered ring, such as octahydro-1H-pyrrolo[3,4-b]pyridine, 1,3-dihydro-isoindol, 2,3-dihydro-indol or 3,9-dioxa-7-azabicyclo[3.3.1]nonan, for example; or a bicyclic 10-membered ring, such as decahydroquinoline or 3,4-dihydroisoquinolin, for example.

The term "heterospirocycloalkyl" means a bicyclic, saturated heterocycle with 6, 7, 8, 9, 10 or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxazaspiro[4.3]octyl, oxaazaspiro[2.5]octyl, azaspiro[4.5]decyl, oxazaspiro[5.5]undecyl, diazaspiro[3.3]heptyl, thiazaspiro[3.3]heptyl, thiazaspiro[4.3]octyl, azaspiro[5.5]undecyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "6- or 10-membered aryl" means a monovalent, monocyclic or bicyclic aromatic ring having 6 or 10 carbon ring atoms, e.g. a phenyl or naphthyl group.

The term "heteroaryl" means a monovalent, monocyclic, bicyclic or tricyclic aromatic ring having 5, 6, 9 or 10 ring atoms (a "5- to 10-membered heteroaryl" group), particularly 5 or 6 ring atoms (a "5- to 6-membered heteroaryl" group), which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, dihydropyridinyl, pyridazinyl, pyrimidinyl, tetrahydropyrimidinyl, pyrazinyl or triazinyl.

The term "heterocyclyl" means a heterocycle selected from the group consisting of heterocycloalkyl and heteroaryl. Particularly, the term "4- to 6-membered heterocyclyl" means a heterocycle selected from the group consisting of 4- to 6-membered heterocycloalkyl and 5- to 6-membered heteroaryl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_4$", as used in the present text, e.g. in the context of the definition of "$C_1$-$C_4$-alkyl", "$C_1$-$C_4$-halogenoalkyl", "$C_1$-$C_4$-hydroxyalkyl", "$C_1$-$C_4$-alkoxy" or "$C_1$-$C_4$-halogenoalkoxy" means an alkyl group having a finite number of carbon atoms of 1 to 4, i.e. 1, 2, 3 or 4 carbon atoms.

Further, as used herein, the term "$C_3$-$C_6$", as used in the present text, e.g. in the context of the definition of "$C_3$-$C_6$-cycloalkyl" or $C_3$-$C_6$-halogenocycloalkyl, means a cycloalkyl group having a finite number of carbon atoms of 3 to 6, i.e. 3, 4, 5 or 6 carbon atoms.

When a range of values is given, said range encompasses each value and sub-range within said range.

For example:

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_4$" encompasses $C_3$, $C_4$, and $C_3$-$C_4$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_5$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_4$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$, and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

An oxo substituent in the context of the invention means an oxygen atom, which is bound to a carbon atom via a double bond.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (T)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^{2}H$ (deuterium), 3H (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prevention of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^{3}H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO20121112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome POW.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quaternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with a second embodiment of the first aspect, the present invention covers compounds of general formula (I), supra, in which:

A is A1 or A2,

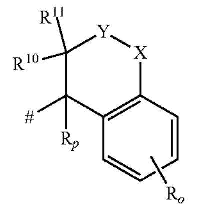

A1

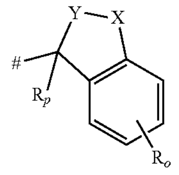

A2 is 0, 1, 2, 3 or 4,

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, $R_p$ is selected from the group consisting of hydrogen, $C_1$-$C_4$-alkyl, X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—, $R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of tetrahydro-2H-pyran-4-yl, 3,6-dihydro-2H-pyran-4-yl, ethyl and 3-fluoroazetidin-1-yl, $R^3$ is hydrogen, or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, preferably hydrogen, halogen and $C_1$-$C_4$-alkoxy, more preferably fluorine, chlorine, methoxy and isopropoxy, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, $R^7$ is selected from the group consisting of hydrogen, —OH, fluorine, $C_1$-$C_4$-alkyl and $C_1$-$C_4$-alkoxy, $R^8$ is selected from the group consisting of hydrogen, —OH, fluorine, $C_1$-$C_4$-alkyl and $C_1$-$C_4$-alkoxy, or $R^7$ and $R^8$ together form an oxo group (═O), $R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy, $R^{10}$ is selected from the group consisting of hydrogen, —OH, $C_1$-$C_4$-alkyl and $C_1$-$C_4$-alkoxy, $R^{11}$ is selected from the group consisting of hydrogen, $C_1$-$C_4$-alkyl and $C_1$-$C_4$-alkoxy, Q is 2,3,5-trifluorophenyl, wherein when Y is O, S or N—$R^9$, none of $R^7$, $R^8$, $R^{10}$ and $R^{11}$ is —OH or $C_1$-$C_4$-alkoxy, and wherein when X is O, S or N—$R^9$, none of $R^7$ and $R^8$ is —OH or $C_1$-$C_4$-alkoxy;

and wherein a compound according to the formula

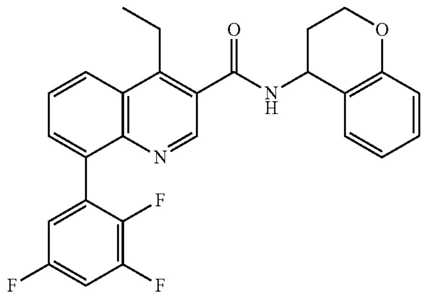 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In accordance with a third embodiment of the first aspect, the present invention covers compounds of general formula (I), supra, in which:

A is A1 or A2,

A1

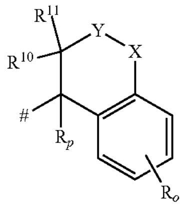

A2

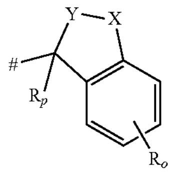

is 0, 1 or 2,

R is selected from the group consisting of halogen, $C_1$-$C_4$-alkyl and $C_1$-$C_4$-alkoxy, cyano, $C_1$-$C_4$-halogenoalkyl having 1 to 5 halogen atoms, $R_p$ is selected from the group consisting of hydrogen, $C_1$-$C_4$-alkyl, X, Y are independently selected from the group consisting of $CR^7R^8$, O, S, and N—$R^9$, wherein at least one of X and Y is $CR^7R^8$, $R^1$ is selected from the group consisting of hydrogen, $C_1$-$C_4$-alkyl, $C_3$-$C_6$-cycloalkyl, $C_1$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, $R^2$ is selected from the group consisting of tetrahydro-2H-pyran-4-yl, 3,6-dihydro-2H-pyran-4-yl, ethyl and 3-fluoroazetidin-1-yl, $R^3$ is hydrogen or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, preferably hydrogen, halogen and $C_1$-$C_4$-alkoxy, more preferably fluorine, chlorine, methoxy and isopropoxy, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_1$-alkyl), —N($C_1$-$C_1$-alkyl)$_2$, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$.

$R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^9$ is $C_1$-$C_4$-alkyl, $R^{10}$ is selected from the group consisting of hydrogen, —OH, $C_1$-$C_4$-alkyl and $C_1$-$C_4$-alkoxy, $R^{11}$ is hydrogen, Q is 2,3,5-trifluorophenyl, wherein when Y is O, S or N—$R^9$, $R^{10}$ is not —OH or $C_1$-$C_4$-alkoxy;

and wherein a compound according to the formula

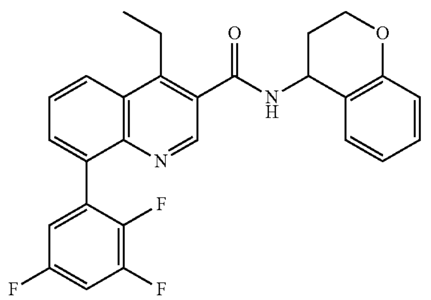 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In accordance with a fourth embodiment of the first aspect, the present invention covers compounds of general formula (I), supra, in which:

A is A1 or A2,

A1

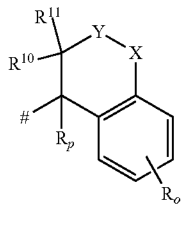

-continued

A2

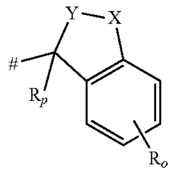

is 0, 1 or 2.

R is selected from the group consisting of halogen, $C_1$-$C_4$-alkyl, $C_1$-$C_4$-alkoxy and cyano, $R_p$ is selected from the group consisting of hydrogen, $C_1$-$C_4$-alkyl.

X is selected from the group consisting of $CR^7R^8$, O, S, and N—$R^9$,

Y is $CR^7R^8$ or O, $R^1$ is hydrogen or $C_1$-$C_4$-alkyl, $R^2$ is selected from the group consisting of tetrahydro-2H-pyran-4-yl, 3,6-dihydro-2H-pyran-4-yl, ethyl and 3-fluoroazetidin-1-yl, $R^3$ is hydrogen or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, preferably hydrogen, halogen and $C_1$-$C_4$-alkoxy, more preferably fluorine, chlorine, methoxy and isopropoxy, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^9$ is $C_1$-$C_4$-alkyl, $R^{10}$ is selected from the group consisting of hydrogen, —OH and $C_1$-$C_4$-alkyl, $R^{11}$ is hydrogen.

Q is 2,3,5-trifluorophenyl, wherein a compound according to the formula

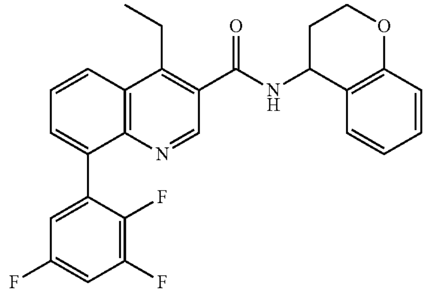 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In accordance with a fifth embodiment of the first aspect, the present invention covers compounds of general formula (I), supra, in which:

A is selected from the group consisting of
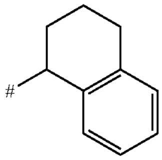
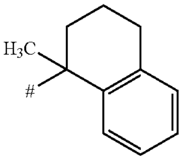
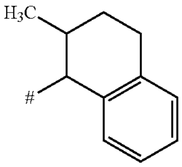
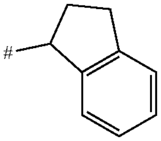
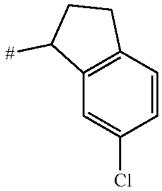
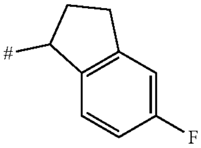
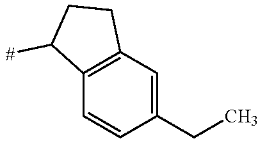
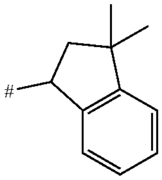
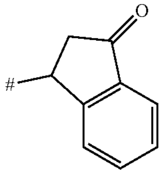
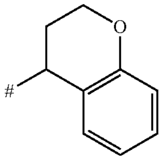
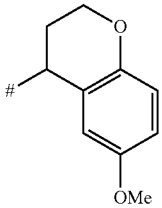
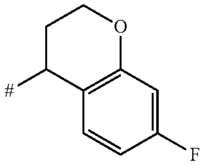
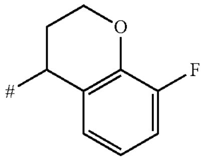
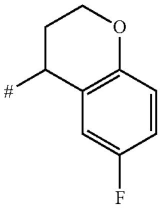
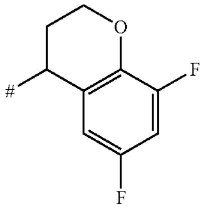
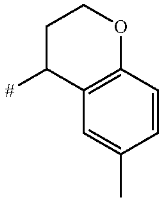
-continued
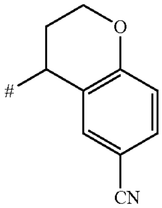
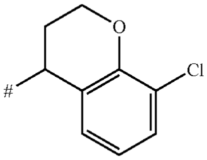
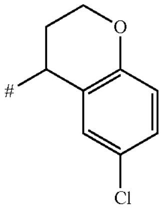
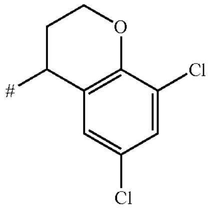
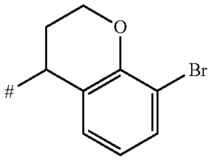
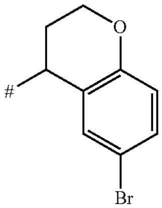
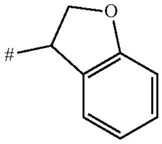
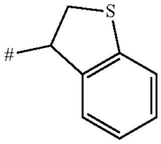
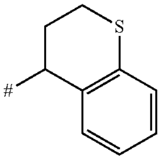
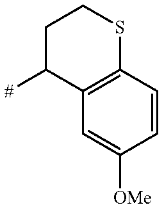
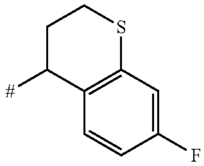
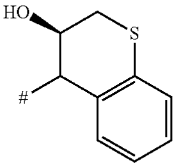
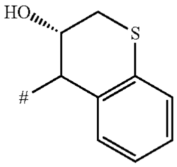
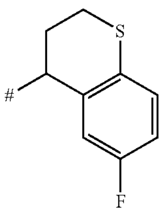
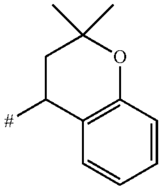
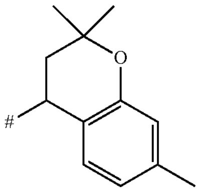
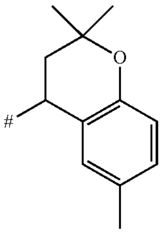

-continued

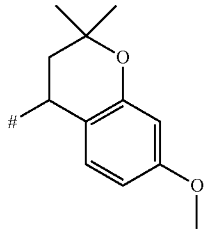
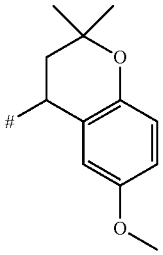
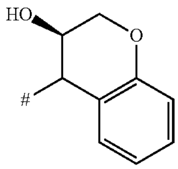
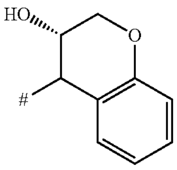
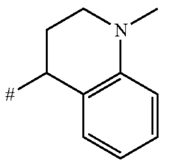
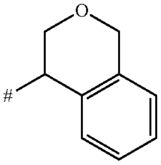
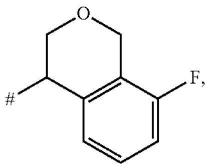

$R^1$ is hydrogen or methyl, $R^2$ is selected from the group consisting of tetrahydro-2H-pyran-4-yl, 3,6-dihydro-2H-pyran-4-yl, ethyl and 3-fluoroazetidin-1-yl, $R^3$ is hydrogen or methyl, $R^4$ is selected from the group consisting of hydrogen, fluorine, chlorine, —OH, cyano, methyl, methoxy, trifluoromethyl, trifluoromethoxy and $NH_2$, preferably hydrogen, fluorine, chlorine and $C_1$-$C_4$-alkoxy, more preferably fluorine, chlorine, methoxy and isopropoxy, $R^5$ is selected from the group consisting of hydrogen, fluorine, chlorine, —OH, cyano, methyl, methoxy and trifluoromethyl, $R^6$ is selected from the group consisting of hydrogen, fluorine, chlorine, —OH, cyano, methyl and methoxy, Q is 2,3,5-trifluorophenyl, wherein a compound according to the formula

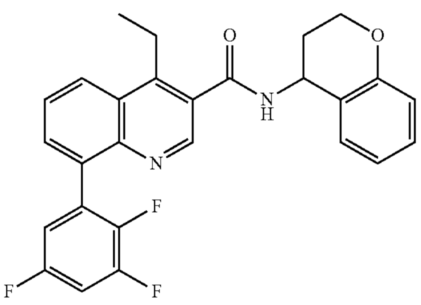 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In accordance with a sixth embodiment of the first aspect, the present invention covers compounds of general formula (I), supra, in which:

A is selected from the group consisting of

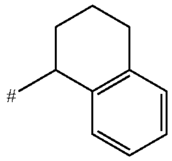
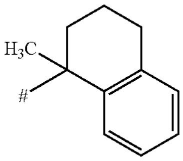
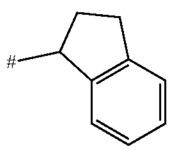
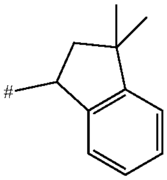
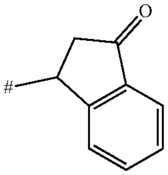
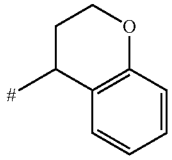
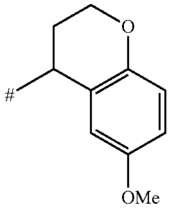
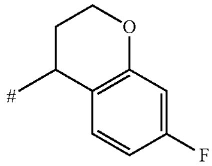
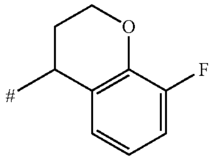
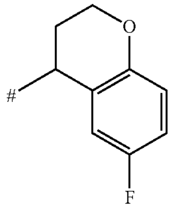
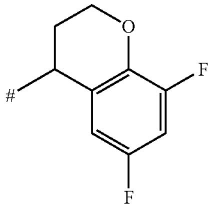
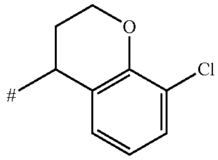
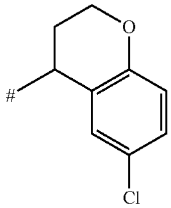
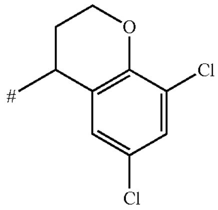
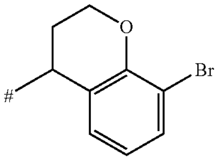
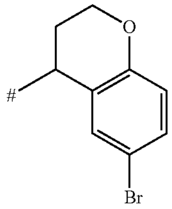
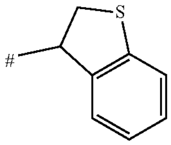

-continued

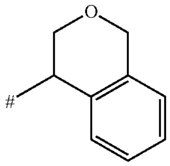
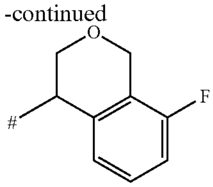
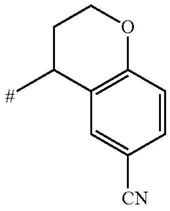
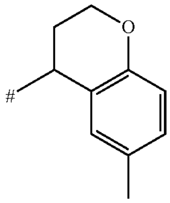
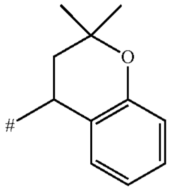
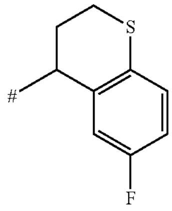
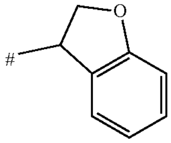
, $R^1$ is hydrogen or methyl, $R^2$ is selected from the group consisting of tetrahydro-2H-pyran-4-yl, 3,6-dihydro-2H-pyran-4-yl, ethyl and 3-fluoroazetidin-1-yl, $R^3$ is hydrogen or methyl, $R^4$ is selected from the group consisting of hydrogen, chlorine, fluorine, methyl, methoxy, isopropoxy and trifluoromethyl, preferably hydrogen, fluorine, chlorine, methoxy and isopropoxy, $R^5$ is selected from the group consisting of hydrogen, chlorine, fluorine, —OH, cyano, methyl, trifluoromethoxy and NHL.

$R^6$ is selected from the group consisting of hydrogen, fluorine, chlorine, —OH, cyano, methyl and methoxy, Q is 2,3,5-trifluorophenyl, wherein a compound according to the formula

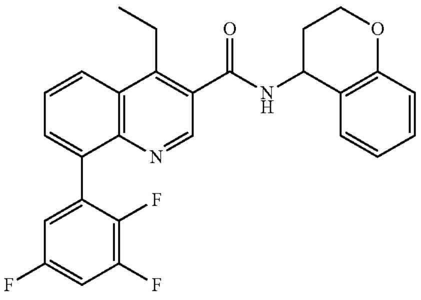 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts, thereof, and mixtures of same.

In accordance with a seventh embodiment of the first aspect, the present invention covers compounds of general formula (I), supra, in which:

A is selected from the group consisting of

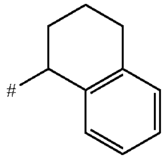
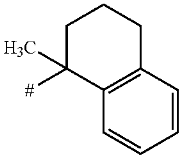
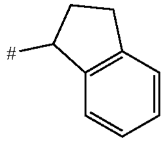
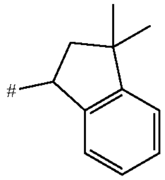
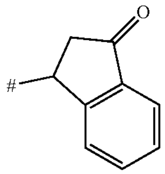
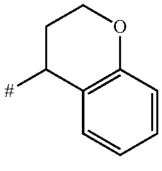
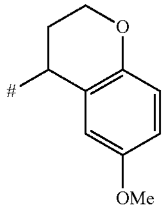
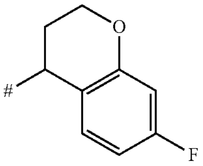
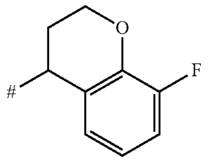
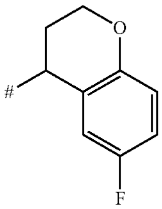
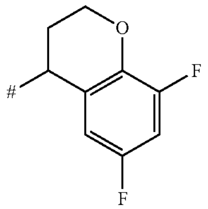
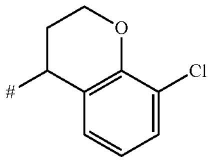
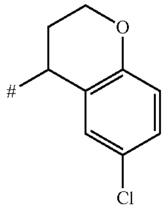
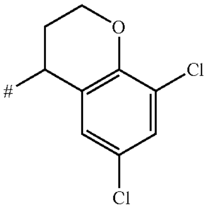
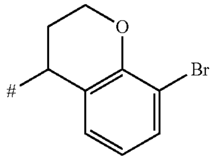
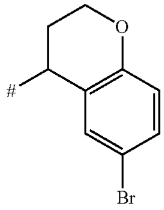

-continued

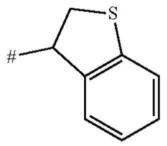

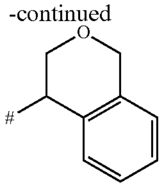

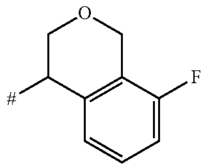

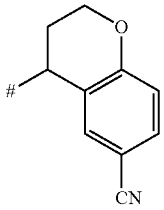

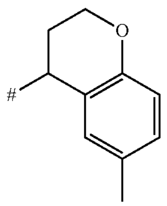

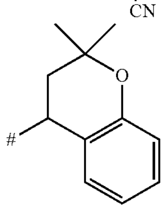

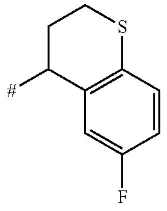

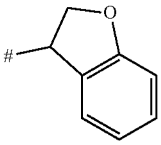, $R^1$ is hydrogen or methyl, $R^2$ is selected from the group consisting of tetrahydro-2H-pyran-4-yl, 3,6-dihydro-2H-pyran-4-yl, ethyl and 3-fluoroazetidin-1-yl, $R^3$ is hydrogen or methyl, $R^4$ is selected from the group consisting of hydrogen, chlorine, fluorine, —OH, cyano, methyl, methoxy, trifluoromethyl, trifluoromethoxy and $NH_2$, preferably hydrogen, fluorine, chlorine, methoxy and isopropoxy, $R^5$ is selected from the group consisting of hydrogen, chlorine, fluorine, —OH, cyano, methyl, methoxy and trifluoromethyl, $R^5$ is selected from the group consisting of hydrogen, fluorine, chlorine, —OH, cyano, methyl and methoxy, Q is 2,3,5-trifluorophenyl, wherein a compound according to the formula

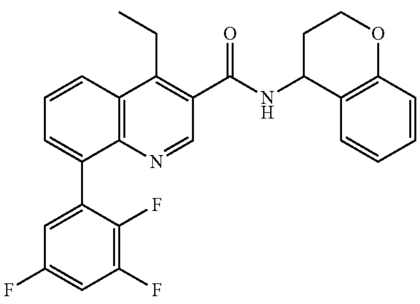 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In accordance with an eighth embodiment of the first aspect, the present invention covers compounds of general formula (I), supra, in which:

A is A3 or A4

A3

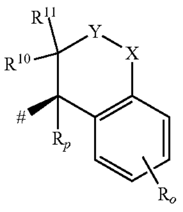

A4

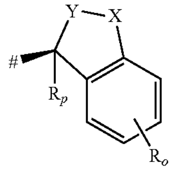

is 0 or 1,

R is selected from the group consisting of halogen, $C_1$-$C_4$-alkyl, $C_1$-$C_4$-alkoxy and cyano, $R_p$ is selected from the group consisting of hydrogen, $C_1$-$C_4$-alkyl, X is selected from the group consisting of $CR^7R^8$, O, S, and N—$R^9$, Y is $CR^7R^8$ or O, $R^1$ is hydrogen or $C_1$-$C_4$-alkyl, $R^2$ is selected from the group consisting of tetrahydro-2H-pyran-4-yl, 3,6-dihydro-2H-pyran-4-yl, ethyl and 3-fluoroazetidin-1-yl, $R^3$ is hydrogen or $C_1$-$C_4$-alkyl, $R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $NH_2$, preferably hydrogen, halogen and $C_1$-$C_4$-alkoxy, more preferably fluorine, chlorine, methoxy and isopropoxy, $R^5$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^9$ is $C_1$-$C_4$-alkyl, $R^{10}$ is selected from the group consisting of hydrogen, —OH and $C_1$-$C_4$-alkyl, $R^{11}$ is hydrogen, Q is 2,3,5-trifluorophenyl, wherein a compound according to the formula

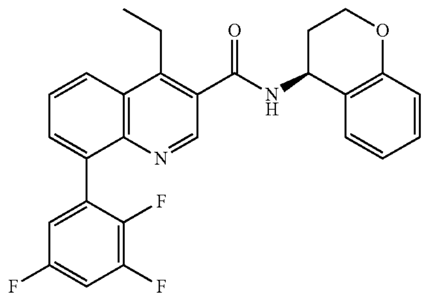 [SMILES: CCc1c(C(=O)N[C@H]2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

Further embodiments of the first aspect of the present invention:

In a further embodiment of the first aspect, the present invention covers compounds of formula (I), supra, in which:

A is A1 or A2,

A1

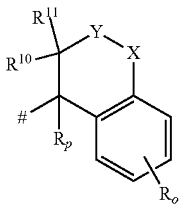

A2

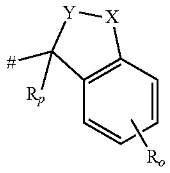

is 0, 1 or 2,

R is selected from the group consisting of halogen, $C_1$-$C_4$-alkyl and $C_1$-$C_4$-alkoxy, cyano, $C_1$-$C_4$-halogenoalkyl having 1 to 5 halogen atoms, $R_p$ is hydrogen, X, Y are independently selected from the group consisting of $CR^7R^8$, O, S, and N—$R^9$, wherein at least one of X and Y is $CR^7R^8$, $R^7$ is selected from the group consisting of hydrogen and $C_1$-$C_4$-alkyl, $R^8$ is selected from the group consisting of hydrogen and $C_1$-$C_4$-alkyl, $R^9$ is $C_1$-$C_4$-alkyl, $R^{10}$ is selected from the group consisting of hydrogen, —OH, $C_1$-$C_4$-alkyl and $C_1$-$C_4$-alkoxy, and $R^{11}$ is hydrogen, wherein when Y is O, S or N—$R^9$, $R^{10}$ is not —OH or $C_1$-$C_4$-alkoxy, and wherein a compound according to the formula

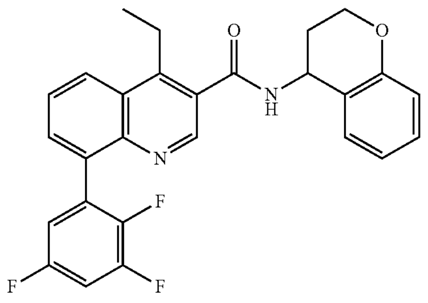 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further embodiment of the first aspect, the present invention covers compounds of formula (I), supra, in which:

A is A1 or A2,

A1

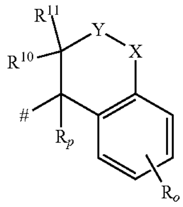

A2

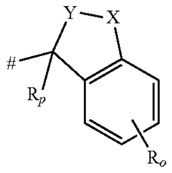

is 0, 1 or 2,

R is selected from the group consisting of halogen, $C_1$-$C_4$-alkyl and $C_1$-$C_4$-alkoxy, cyano, $C_1$-$C_4$-halogenoalkyl having 1 to 5 halogen atoms, $R_p$ is selected from the group consisting of hydrogen, $C_1$-$C_4$-alkyl, X, Y are independently selected from the group consisting of $CR^7R^8$, O, S, and N—$R^9$, wherein at least one of X and Y is $CR^7R^8$, $R^7$ is selected from the group consisting of hydrogen and $C_1$-$C_4$-alkyl.

$R^8$ is selected from the group consisting of hydrogen and $C_1$-$C_4$-alkyl, or $R^7$ and $R^8$ together form an oxo group (═O), $R^9$ is $C_1$-$C_4$-alkyl, $R^{10}$ is selected from the group consisting of hydrogen, —OH, $C_1$-$C_4$-alkyl and $C_1$-$C_4$-alkoxy, and $R^{11}$ is hydrogen, wherein when Y is O, S or N—$R^9$, $R^{10}$ is not —OH or $C_1$-$C_4$-alkoxy, and wherein a compound according to the formula

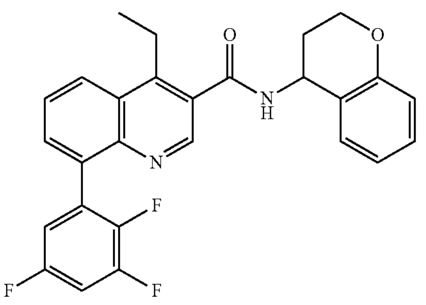 [SMILES: CCc1c(C(=O)NC2CCOc3ccccc32)cnc2c(-c3cc(F)cc(F)c3F)cccc12]

is excluded;

and stereoisomers, tautomers. N-oxides, hydrates, solvates, and salts thereof, and mixtures of same.

In a further embodiment of the first aspect, the present invention covers compounds of formula (I), supra, in which:

A is A1 or A2,

A1

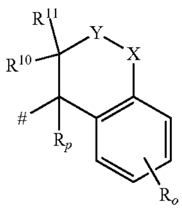

A2

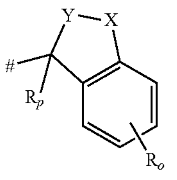

is 0, 1 or 2,

R is selected from the group consisting of halogen, $C_1$-$C_4$-alkyl and $C_1$-$C_4$-alkoxy, cyano, $C_1$-$C_4$-halogenoalkyl having 1 to 5 halogen atoms, $R_p$ is hydrogen, X, Y are independently selected from the group consisting of $CR^7R^8$, O, and S, wherein at least one of X and Y is $CR^7R^8$, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (=O), $R^{10}$ is selected from the group consisting of hydrogen, —OH, $C_1$-$C_4$-alkyl and $C_1$-$C_4$-alkoxy, and $R^{11}$ is hydrogen, wherein when Y is O, S or N—$R^9$, $R^{10}$ is not —OH, and wherein a compound according to the formula

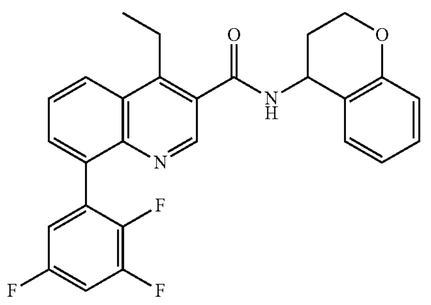 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further embodiment of the first aspect, the present invention covers compounds of formula (I), supra, in which:

A is A1 or A2,

A1

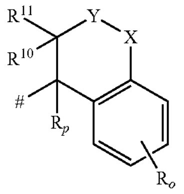

A2

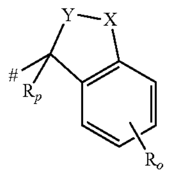

is 0 or 1,

R is selected from the group consisting of halogen, $C_1$-$C_4$-alkyl, $C_1$-$C_4$-alkoxy and cyano, $R_p$ is hydrogen, X is selected from the group consisting of $CR^7R^8$, O, S, and N—$R^9$, Y is $CR^7R^8$, $R^7$ is selected from the group consisting of hydrogen and $C_1$-$C_4$-alkyl, $R^8$ is selected from the group consisting of hydrogen and $C_1$-$C_4$-alkyl, $R^9$ is $C_1$-$C_4$-alkyl, $R^{10}$ is selected from the group consisting of hydrogen, —OH and $C_1$-$C_4$-alkyl, and $R^{11}$ is hydrogen, and wherein a compound according to the formula

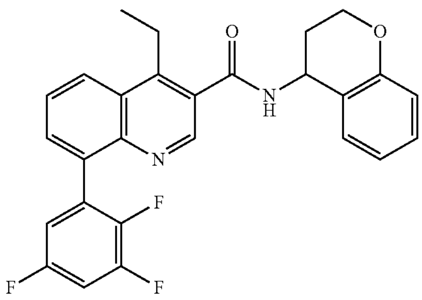 [SMILES: CCc1c(C(=O)NC2CCOc3ccccc32)cnc2c(-c3cc(F)cc(F)c3F)cccc12]

is excluded;

and stereoisomers, tautomers. N-oxides, hydrates, solvates, and salts thereof, and mixtures of same.

In a further embodiment of the first aspect, the present invention covers compounds of formula (I), supra, in which:

A is A1 or A2,

A1

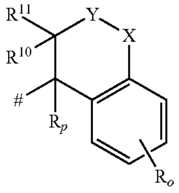

A2

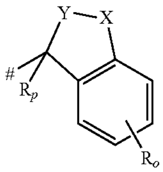

is 0 or 1,

R is selected from the group consisting of halogen, $C_1$-$C_4$-alkyl, $C_1$-$C_4$-alkoxy and cyano, $R_p$ is selected from the group consisting of hydrogen, $C_1$-$C_4$-alkyl, X is selected from the group consisting of $CR^7R^8$, O, S, and N—$R^9$, Y is $CR^7R^8$ or O, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^9$ is $C_1$-$C_4$-alkyl, $R^{10}$ is selected from the group consisting of hydrogen, —OH and $C_1$-$C_4$-alkyl, and $R^{11}$ is hydrogen, wherein a compound according to the formula

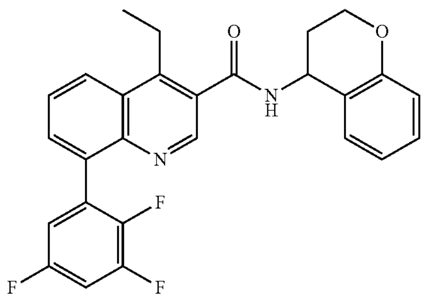 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further embodiment of the first aspect, the present invention covers compounds of formula (I), supra, in which:

A is A1 or A2,

A1

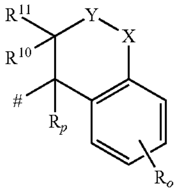

A2

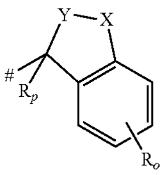

is 0 or 1,

R is selected from the group consisting of halogen, $C_1$-$C_4$-alkyl, $C_1$-$C_4$-alkoxy and cyano, $R_p$ is hydrogen, X is selected from the group consisting of $CR^7R^8$, O and S, Y is $CR^7R^8$ or O, $R^7$ is selected from the group consisting of hydrogen and $C_1$-$C_4$-alkyl, $R^8$ is selected from the group consisting of hydrogen and $C_1$-$C_4$-alkyl, or $R^7$ and $R^8$ together form an oxo group (═O), $R^{10}$ is selected from the group consisting of hydrogen, —OH and $C_1$-$C_4$-alkyl, and $R^{11}$ is hydrogen, wherein a compound according to the formula
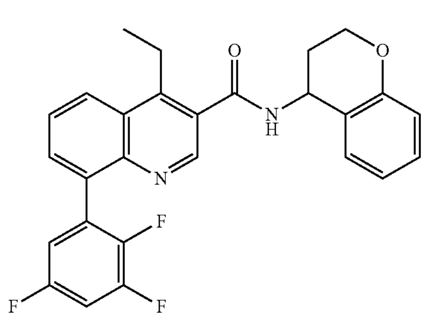 [SMILES: CCc1c(C(=O)NC2CCOc3ccccc32)cnc2c(-c3cc(F)cc(F)c3F)cccc12]
is excluded;
and stereoisomers, tautomers, N-oxides, hydrates, solvates, and salts thereof, and mixtures of same.
In a further embodiment of the first aspect, the present invention covers compounds of formula (I), supra, in which:
A is selected from the group consisting of
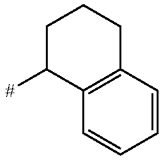
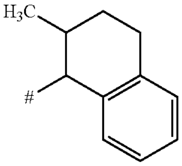
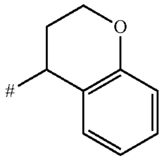
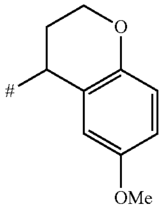
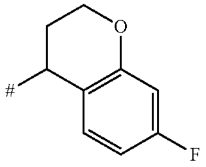
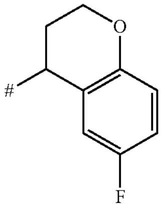
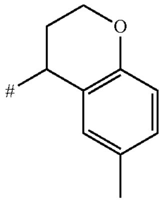
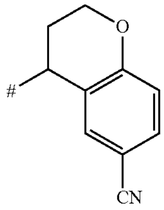
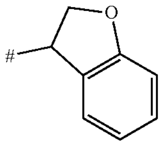
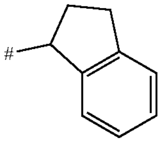
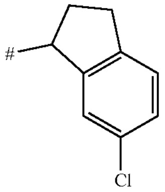
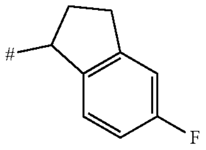
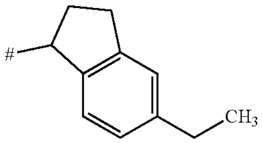
-continued
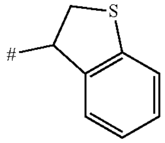
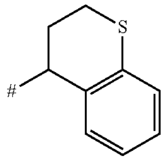
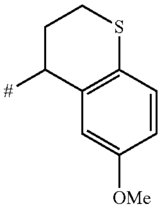
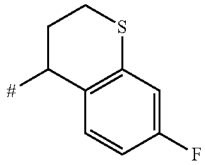
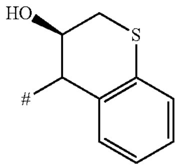
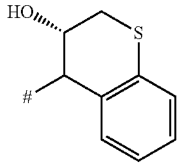
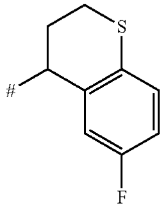
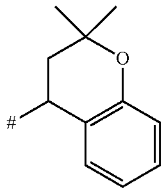
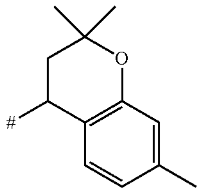
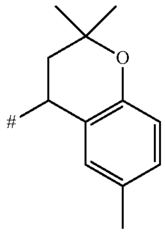
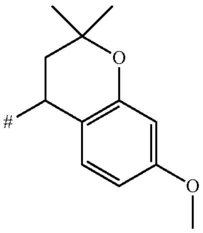
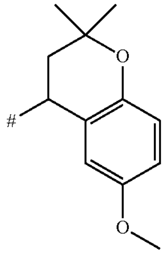
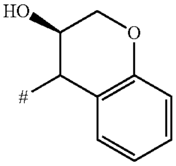
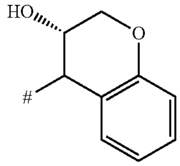
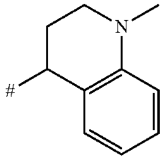

wherein a compound according to the formula
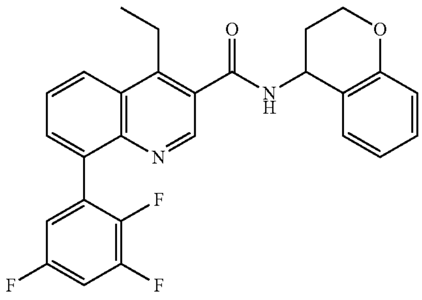 [SMILES: CCc1c(C(=O)NC2CCOc3ccccc32)cnc2c(-c3cc(F)cc(F)c3F)cccc12]
is excluded;
and stereoisomers, tautomers. N-oxides, hydrates, solvates, and salts thereof, and mixtures of same.
In a further embodiment of the first aspect, the present invention covers compounds of formula (I), supra, in which:
A is selected from the group consisting of
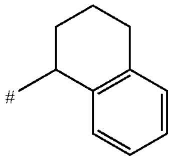
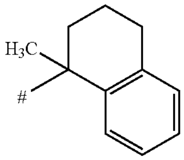
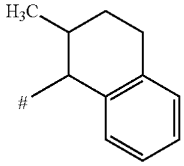
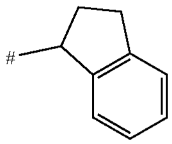
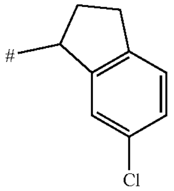
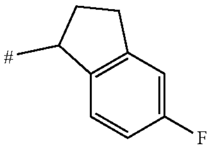
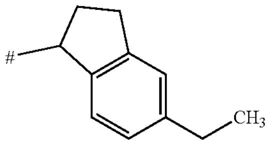
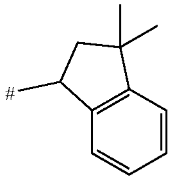
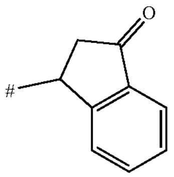
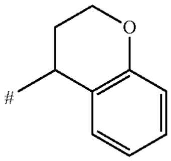
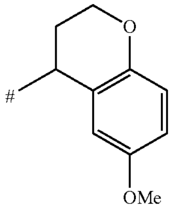
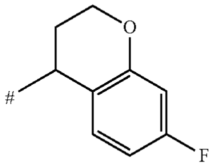
-continued
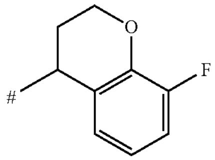
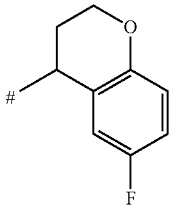
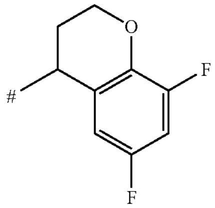
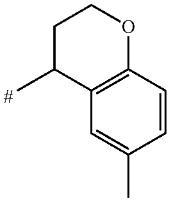
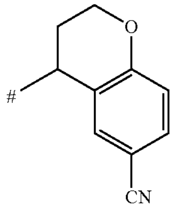
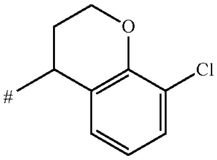
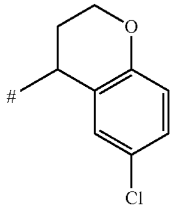
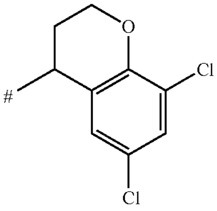
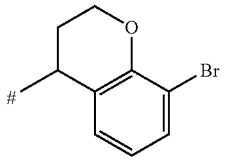
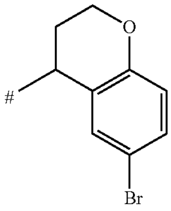
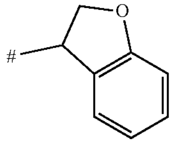
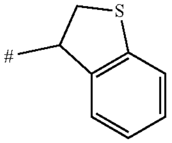
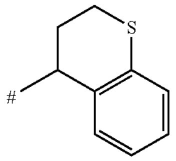
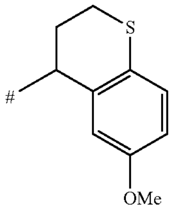
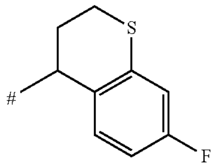
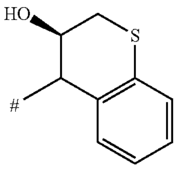

-continued
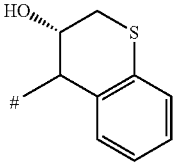
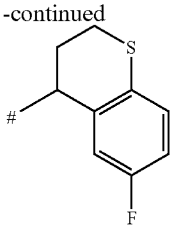
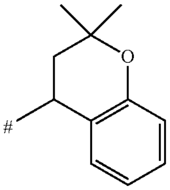
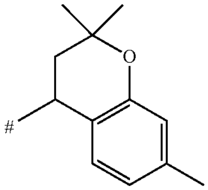
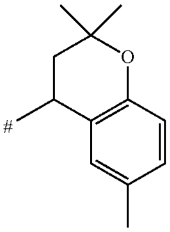
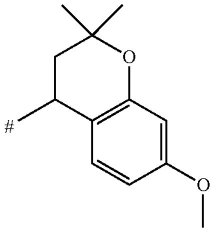
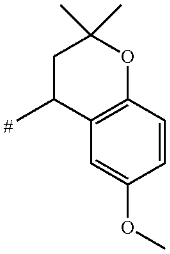
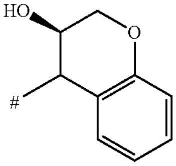
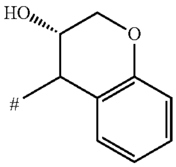
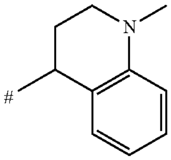
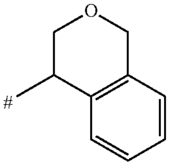
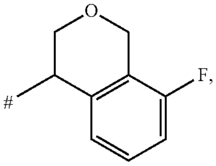,
wherein a compound according to the formula
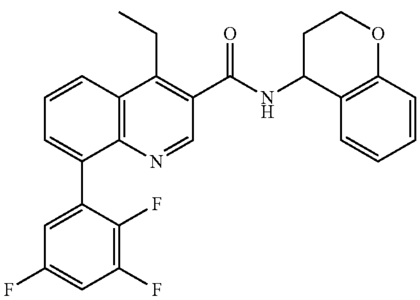 [SMILES: CCc1c(C(=O)NC2CCOc3ccccc32)cnc2c(-c3cc(F)cc(F)c3F)cccc12]
is excluded;
and stereoisomers, tautomers, N-oxides, hydrates, solvates, and salts thereof, and mixtures of same.
In a further embodiment of the first aspect, the present invention covers compounds of formula (I), supra, in which:
A is selected from the group consisting of
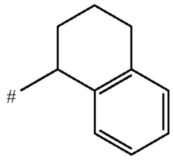
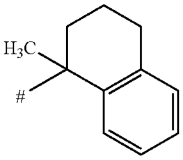
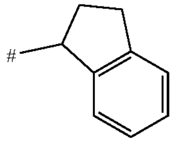
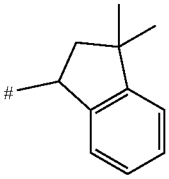
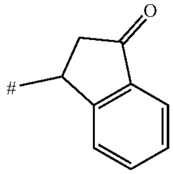
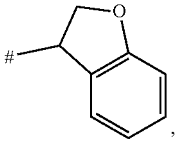,
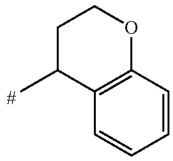
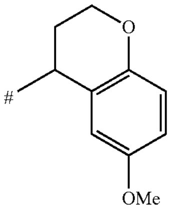
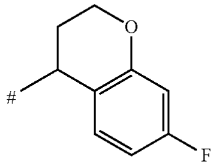
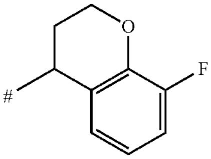
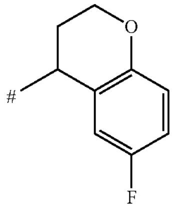
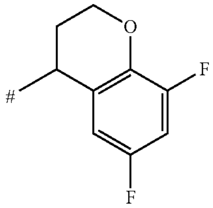
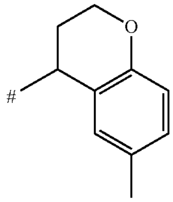
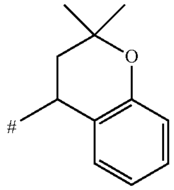
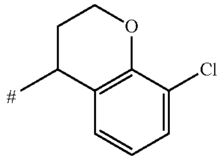
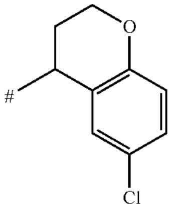

-continued

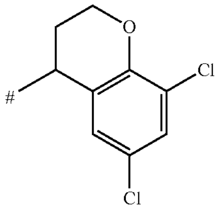
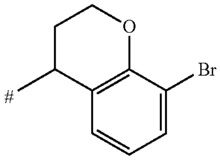
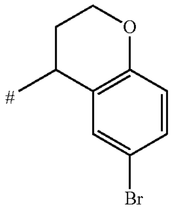
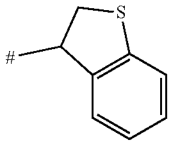
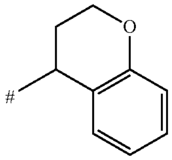
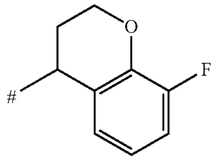
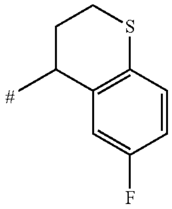
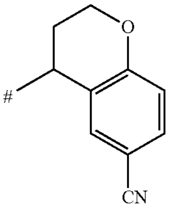
, preferably

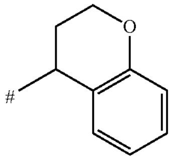
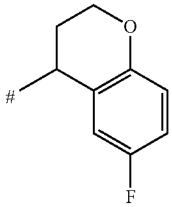
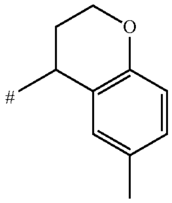
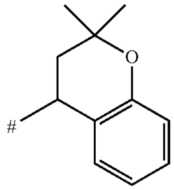
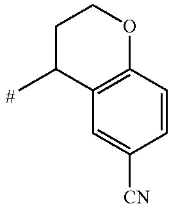
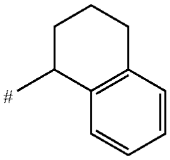
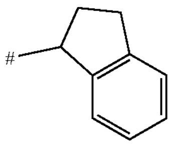
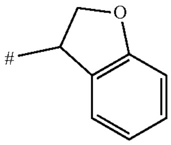
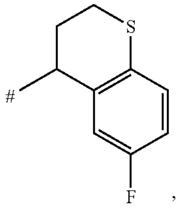
, wherein a compound according to the formula

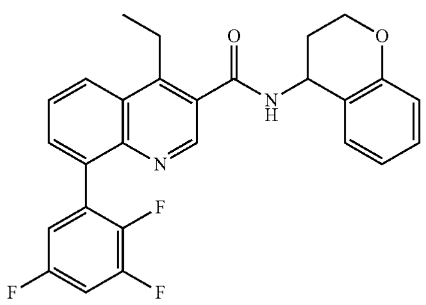 [SMILES: CCc1c(C(=O)NC2CCOc3ccccc32)cnc2c(-c3cc(F)cc(F)c3F)cccc12]

is excluded;

and stereoisomers, tautomers. N-oxides, hydrates, solvates, and salts thereof, and mixtures of same.

In a further embodiment of the first aspect, the present invention covers compounds of formula (I), supra, in which:

A is selected from a group $A^1$ as defined anywhere herein supra; preferably, A is

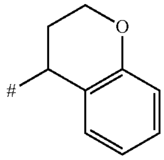
;

with the proviso that $R^4$ is not hydrogen when $R^2$ is ethyl and when A is

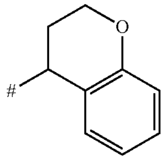
.

In a further embodiment of the first aspect, the present invention covers compounds of formula (I), supra, in which:

$R^2$ is selected from the group consisting of tetrahydro-2H-pyran-4-yl, 3,6-dihydro-2H-pyran-4-yl, ethyl and 3-fluoroazetidin-1-yl, wherein a compound according to the formula

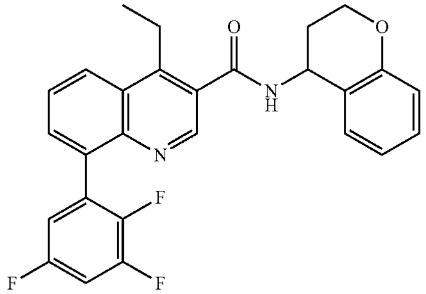 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further embodiment of the first aspect, the present invention covers compounds of formula (I), supra, in which:

$R_p$ is hydrogen or $C_1$-$C_4$-alkyl, wherein a compound according to the formula

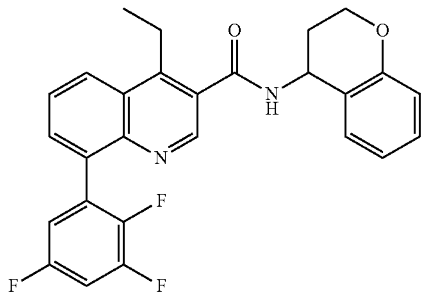 [SMILES: CCc1c(C(=O)NC2CCOc3ccccc32)cnc2c(-c3cc(F)cc(F)c3F)cccc12]

is excluded;

and stereoisomers, tautomers. N-oxides, hydrates, solvates, and salts thereof, and mixtures of same.

In a further embodiment of the first aspect, the present invention covers compounds of formula (I), supra, in which:

$R_p$ is hydrogen or methyl, wherein a compound according to the formula

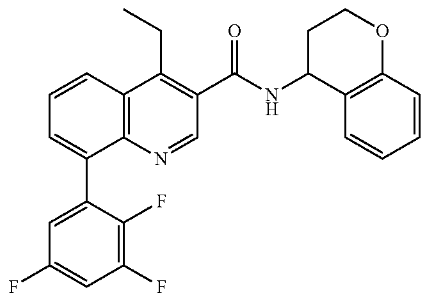 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further embodiment of the first aspect, the present invention covers compounds of formula (I), supra, in which:

$R^3$ is hydrogen or $C_1$-$C_4$-alkyl, wherein a compound according to the formula

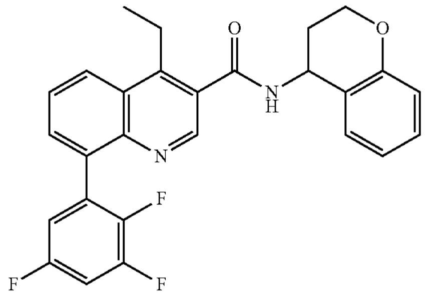 [SMILES: CCc1c(C(=O)NC2CCOc3ccccc32)cnc2c(-c3cc(F)cc(F)c3F)cccc12]

is excluded:

and stereoisomers, tautomers, N-oxides, hydrates, solvates, and salts thereof, and mixtures of same.

In a further embodiment of the first aspect, the present invention covers compounds of formula (I), supra, in which:

$R^3$ is hydrogen or methyl, wherein a compound according to the formula

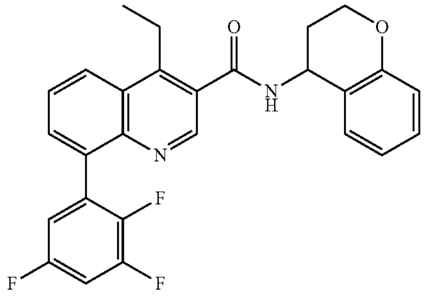 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further embodiment of the first aspect, the present invention covers compounds of formula (I), supra, in which:

$R^4$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $NH_2$, preferably hydrogen, halogen and $C_1$-$C_4$-alkoxy, more preferably fluorine, chlorine, methoxy and isopropoxy, wherein a compound according to the formula

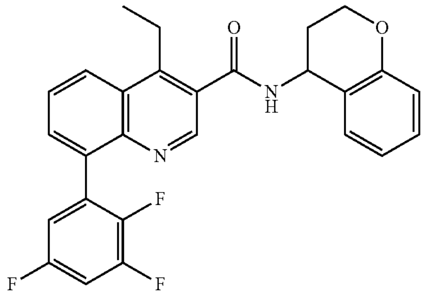 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further embodiment of the first aspect, the present invention covers compounds of formula (I), supra, in which:

$R^4$ is selected from the group consisting of hydrogen, chlorine, fluorine, —OH, cyano, methyl, methoxy, isopropoxy, trifluoromethyl, trifluoromethoxy and $NH_2$, preferably hydrogen, fluorine, chlorine, methoxy and isopropoxy, wherein a compound according to the formula

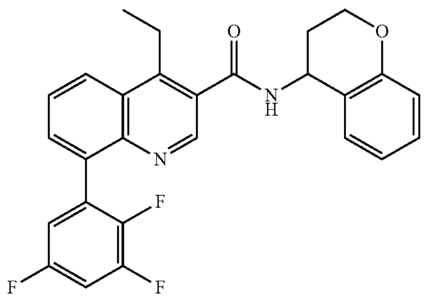 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further embodiment of the first aspect, the present invention covers compounds of formula (I), supra, in which:

$R^5$ is selected from the group consisting of hydrogen, —OH, cyano, $C_1$-$C_4$-alkyl, $C_1$-$C_4$-halogenoalkyl halogenoalkyl having 1 to 5 halogen atoms, $C_1$-$C_4$-alkyl, $C_1$-$C_4$-halogenoalkyl having 1 to 5 halogen atoms, wherein a compound according to the formula

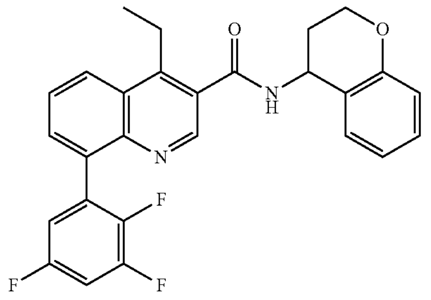 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further embodiment of the first aspect, the present invention covers compounds of formula (I), supra, in which:

$R^5$ is selected from the group consisting of hydrogen, chlorine, fluorine, —OH, cyano, methyl, methoxy and trifluoromethyl, wherein a compound according to the formula

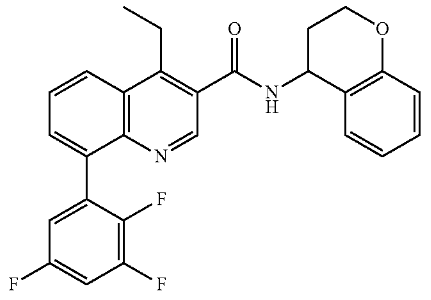 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further embodiment of the first aspect, the present invention covers compounds of formula (I), supra, in which:

$R^6$ is selected from the group consisting of hydrogen, halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, wherein a compound according to the formula

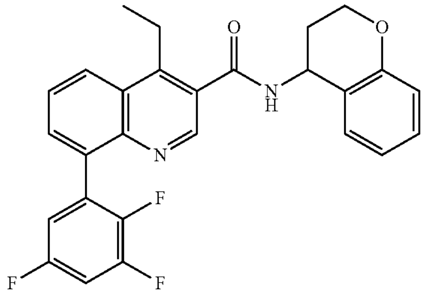 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further embodiment of the first aspect, the present invention covers compounds of formula (I), supra, in which:

$R^5$ is selected from the group consisting of hydrogen, fluorine, chlorine, —OH, cyano, methyl and methoxy, wherein a compound according to the formula

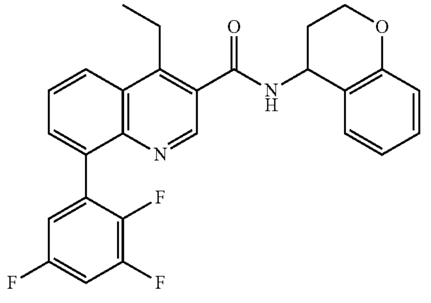 [SMILES: CCc1c(C(=O)NC2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further embodiment of the first aspect, the present invention covers compounds of formula (I), supra, in which:

$R^2$ is tetrahydro-2H-pyran-4-yl,

Q is 2,3,5-trifluorophenyl, and stereoisomers, tautomers. N-oxides, hydrates, solvates, and salts thereof, and mixtures of same.

In a further embodiment of the first aspect, the present invention covers compounds of formula (I), supra, in which:

$R^2$ is 3,6-dihydro-2H-pyran-4-yl,

Q is 2,3,5-trifluorophenyl, and stereoisomers, tautomers, N-oxides, hydrates, solvates, and salts thereof, and mixtures of same.

In a further embodiment of the first aspect, the present invention covers compounds of formula (I), supra, in which:

$R^2$ is ethyl, $R^4$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, preferably hydrogen, halogen and $C_1$-$C_4$-alkoxy, more preferably fluorine, chlorine, methoxy and isopropoxy, Q is 2,3,5-trifluorophenyl, with the proviso that $R^4$ is not hydrogen, when A is

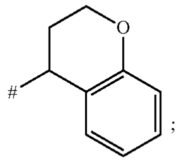

and stereoisomers, tautomers, N-oxides, hydrates, solvates, and salts thereof, and mixtures of same.

In a further embodiment of the first aspect, the present invention covers compounds of formula (I), supra, in which:

$R^2$ is 3-fluoroazetidin-1-yl,

Q is 2,3,5-trifluorophenyl, and stereoisomers, tautomers, N-oxides, hydrates, solvates, and salts thereof, and mixtures of same.

In a further embodiment of the first aspect, the present invention covers compounds of formula (I), supra, in which A is A3 or A4

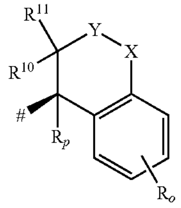

A3

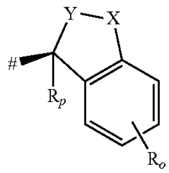

A4

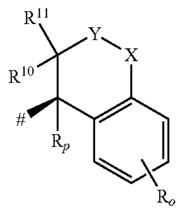

A3

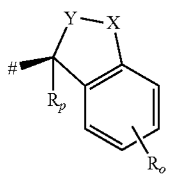

A4 wherein $R_p$ is selected from the group consisting of hydrogen, $C_1$-$C_4$-alkyl; preferably hydrogen, wherein a compound according to the formula

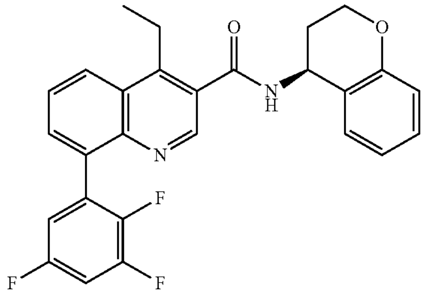 [SMILES: CCc1c(C(=O)N[C@H]2CCOc3ccccc32)cnc2c(-c3cc(F)cc(F)c3F)cccc12]

is excluded;

and stereoisomers, tautomers, N-oxides, hydrates, solvates, and salts thereof, and mixtures of same.

In a further aspect of the present invention in any or all of the embodiments described anywhere herein in the definition of X and/or Y "$NR^9$" as defined supra is excluded.

In a further aspect the present invention covers the compounds of formula (I), as defined in any of the embodiments herein, in which:

$R^4$ has the meaning as defined anywhere herein, with the proviso that $R^4$ is not hydrogen when $R^2$ is ethyl and when A is

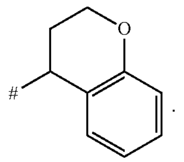

Further, a compound according to the formula

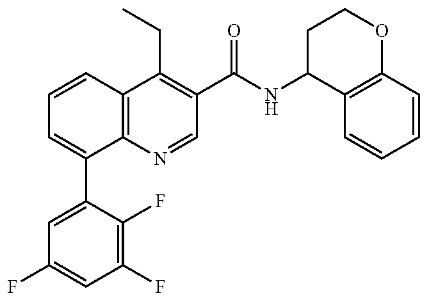 [SMILES: CCc1c(C(=O)NC2CCOc3ccccc32)cnc2c(-c3cc(F)cc(F)c3F)cccc12]

is excluded from the present invention.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers the compounds of general formula (I) which are disclosed in the Example Section of this text, infra.

The compounds according to the invention of general formula (I) can be prepared according to the schemes 1-5 as shown in the Experimental Section to the present invention (General Procedures). The schemes and procedures described illustrate synthetic routes to the compounds of general formula (I) of the invention and are not intended to be limiting. It is clear to the person skilled in the art that the order of transformations as exemplified in schemes 1-5 can be modified in various ways. The order of transformations exemplified in these schemes is therefore not intended to be limiting. In addition, interconversion of any of the substituents, Q, A, $R^1$, $R^2$, $R^3$, $R^4$, $R^5$ or $R^6$ can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis,* 3rd edition, Wiley 1999). Specific examples are described in the subsequent paragraphs.

In accordance with a second aspect, the present invention covers methods of preparing compounds of general formula (I) as defined supra, said methods comprising the step of allowing an intermediate compound of general formula 1N:

1N

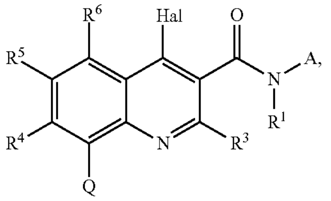

in which A, $R^1$, $R^3$, $R^4$, $R^5$, $R^6$, and Q are as defined for the compound of general formula (I) as defined supra, and Hal is halogen, particularly chlorine and bromine, to react with a compound of general formula 1F:

$R^2H$ 1F, in which $R^2$ is 3-fluoroazetidine, thereby giving a compound of general formula (I)

(I)

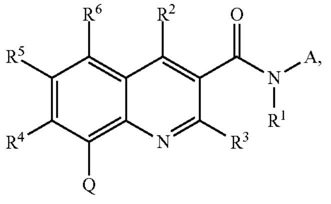

in which A, $R^1$, $R^3$, $R^4$, $R^5$, $R^6$, and Q are as defined supra and $R^2$ is 3-fluoroazetidine, then optionally converting said compound into solvates, salts and/or solvates of such salts using the corresponding (i) solvents and/or (ii) bases or acids.

In accordance with an alternative embodiment of the second aspect, the present invention covers methods of preparing compounds of general formula (I) as defined supra, said methods comprising the step of allowing an intermediate compound of general formula 1T:

1T

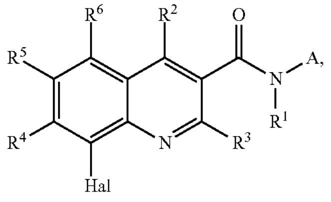

in which A, $R^1$, $R^2$, $R^3$, $R^4$, $R^5$ and $R^6$ are as defined for the compound of general formula (I) as defined supra, and in which Hal is halogen, particularly chlorine, bromine or iodine, with the proviso that $R^4$ is not hydrogen when $R^2$ is ethyl and when A is

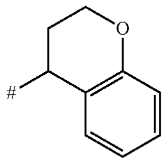
;

to react with a compound of general formula 1H:

$Q\text{-}B(OR)_2$ 1H, in which Q is 2,3,5-trifluorophenyl, and each R may be individually H or Me or both R are pinacolate, thereby giving a compound of general formula (I):

(I)

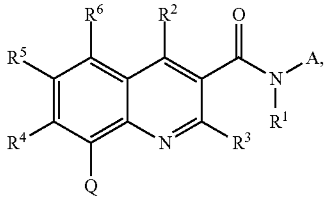

in which A, $R^1$, $R^2$, $R^1$, $R^4$, $R^5$ and $R^6$ are as defined supra and Q is 2,3,5-trifluorophenyl, with the proviso that $R^4$ is not hydrogen when $R^2$ is ethyl and when A is

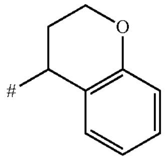
, then optionally converting said compound into solvates, salts and/or solvates of such salts using the corresponding (i) solvents and/or (ii) bases or acids.

In accordance with an alternative embodiment of the second aspect, the present invention covers methods of preparing compounds of general formula (I) as defined supra, said methods comprising the step of allowing an intermediate compound of general formula 1W:

1W

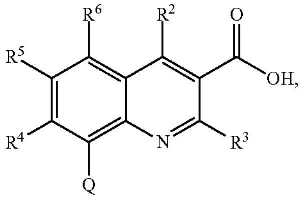

in which Q, $R^2$, $R^3$, $R^4$, $R^5$ and $R^6$ are as defined for the compound of general formula (I) as defined supra, with the proviso that $R^4$ is not hydrogen when $R^2$ is ethyl and when A is

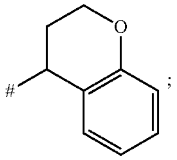

to react with a compound of general formula 1M:

1M

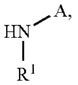

in which $R^1$ and A are as defined for the compound of general formula (I) as defined supra, thereby giving a compound of general formula (I):

(I)

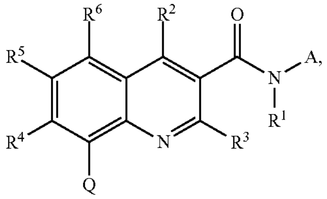

in which A, $R^1$, $R^2$, $R^3$, $R^4$, $R^5$, $R^6$, and Q are as defined supra, with the proviso that $R^4$ is not hydrogen when $R^2$ is ethyl and when A is

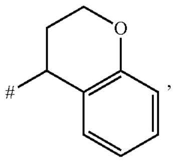

then optionally converting said compound into solvates, salts and/or solvates of such salts using the corresponding (i) solvents and/or (ii) bases or acids.

In accordance with an alternative embodiment of the second aspect, the present invention covers methods of preparing compounds of general formula (I) as defined supra, said methods comprising the step of allowing an intermediate compound of general formula 1N:

1N

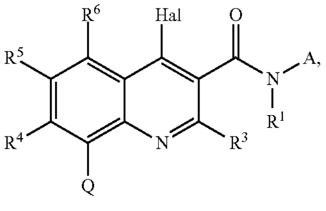

in which Q, A, $R^1$, $R^3$, $R^4$, $R^5$ and $R^6$ are as defined for the compound of general formula (I) as defined supra, and Hal is halogen, particularly chlorine and bromine, to react with a compound of general formula 2A:

$R^2$Met-X 2A, in which $R^2$ is ethyl or 3,6-dihydro-2H-pyran-4-yl, Met is magnesium or zinc, and X is chlorine, bromine or iodine, with the proviso that $R^4$ is not hydrogen when $R^2$ is ethyl and when A is

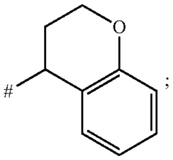

thereby giving a compound of general formula (I):

(I)

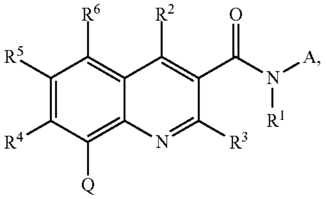

in which A, $R^1$, $R^3$, $R^4$, $R^5$, $R^6$, and Q are as defined supra and $R^2$ is ethyl or 3,6-dihydro-2H-pyran-4-yl, with the proviso that $R^4$ is not hydrogen when $R^2$ is ethyl and when A is

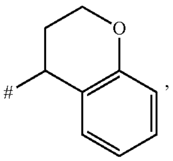

then optionally convening said compound into solvates, salts and/or solvates of such salts using the corresponding (i) solvents and/or (ii) bases or acids.

In accordance with an alternative embodiment of the second aspect, the present invention covers methods of preparing compounds of general formula (I) as defined supra, said methods comprising the step of allowing an intermediate compound of general formula 1N:

1N

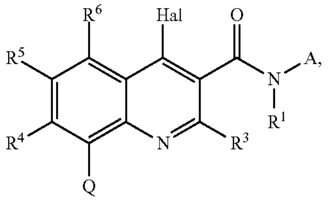

in which Q, A, $R^1$, $R^3$, $R^4$, $R^5$ and $R^6$ are as defined for the compound of general formula (I) as defined supra, and Hal is halogen, particularly chlorine and bromine, to react with a compound of general formula 2P:

2P

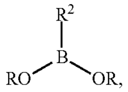

in which $R^2$ is ethyl or 3,6-dihydro-2H-pyran-4-yl, and each R may be individually H or Me or both R are pinacolate, with the proviso that $R^4$ is not hydrogen when $R^2$ is ethyl and when A is

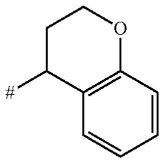

;

thereby giving a compound of general formula (I):

(I)

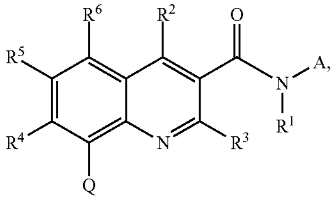

in which A, $R^1$, $R^3$, $R^4$, $R^5$, $R^6$, and Q are as defined supra and $R^2$ is ethyl or 3,6-dihydro-2H-pyran-4-yl, with the proviso that $R^4$ is not hydrogen when $R^2$ is ethyl and when A is

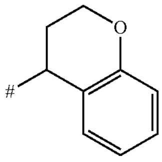

, then optionally converting said compound into solvates, salts and/or solvates of such salts using the corresponding (i) solvents and/or (ii) bases or acids.

In accordance with an alternative embodiment of the second aspect, the present invention covers methods of preparing compounds of general formula (I) as defined supra, said methods comprising the step of allowing an intermediate compound of general formula 1-b1:

I-b1

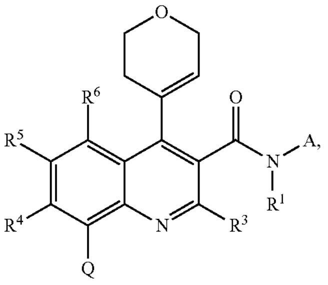

in which Q, A, $R^1$, $R^3$, $R^4$, $R^5$ and $R^6$ are as defined for the compound of general formula (I) as defined supra, to react with hydrogen ($H_2$) in the presence of catalysts, likewise palladium on charcoal, thereby giving a compound of general formula (I):

(I)

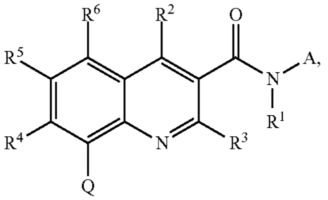

in which A, $R^1$, $R^3$, $R^4$, $R^5$, $R^6$, and Q are as defined supra and $R^2$ is tetrahydropyran-4-yl, then optionally convening said compound into solvates, salts and/or solvates of such salts using the corresponding (i) solvents and/or (ii) bases or acids.

In accordance with a third aspect, the present invention covers intermediate compounds which are useful for the preparation of the compounds of general formula (I), supra.

Particularly, the inventions covers the intermediate compounds of general formula (II):

(II)

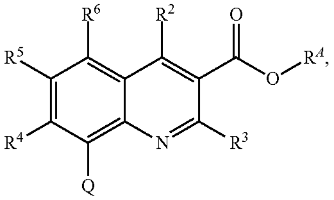

in which $R^2$ is —OH or as defined for the compound of general formula (I) supra, $R^3$, $R^4$, $R^5$, $R^6$, and Q are as defined for the compound of general formula (I) supra, and $R^A$ is H or $C_1$-$C_4$-alkyl, and stereoisomers, tautomers, N-oxides, hydrates, solvates, and salts thereof, and mixtures of same.

In accordance with a fourth aspect, the present invention covers the use of said intermediate compounds for the preparation of a compound of general formula (I) as defined supra.

Particularly, the inventions covers the use of intermediate compounds of general formula (II):

(II)

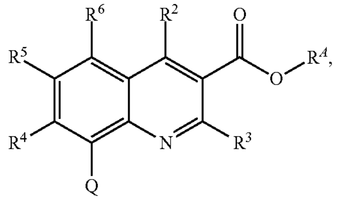

in which $R^2$ is —OH or as defined for the compound of general formula (I) supra, $R^3$, $R^4$, $R^5$, $R^6$, and Q are as defined for the compound of general formula (I) supra, and $R^A$ is H or $C_1$-$C_4$-alkyl, for the preparation of a compound of general formula (I) as defined supra.

The present invention covers the intermediate compounds which are disclosed in the Example Section of this text, infra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action, which could not have been predicted. Compounds of the present invention have surprisingly been found to effectively interact with Slo-1 and it is possible therefore that said compounds be used for the treatment or prevention of diseases, preferably helminthic infections, particularly of gastro-intestinal and extra-intestinal helminth infections, more particularly of gastro-intestinal and extra-intestinal infections with nematodes in humans and animals.

Compounds of the present invention can be utilized to control, treat and/or prevent helminth infections, in particular gastro-intestinal and extra-intestinal helminth infections. This method comprises administering to a mammal in need thereof an amount of a compound of this invention, or a pharmaceutically acceptable salt, isomer, polymorph, metabolite, hydrate, solvate or ester thereof; which is effective to treat the disorder.

In an alternative aspect, this method comprises administering to birds, namely cage birds or in particular poultry, in need thereof an amount of a compound of this invention, or a pharmaceutically acceptable salt, isomer, polymorph, metabolite, hydrate, solvate or ester thereof; which is effective to treat the disorder.

Specifically in the field of veterinary medicine, compounds of the present invention are suitable, with favourable toxicity in warm blooded animals, for controlling parasites, in particular helminths, which occur in animal breeding and animal husbandry in livestock, breeding, zoo, laboratory, experimental and domestic animals. They are active against all or specific stages of development of the parasites, in particular of the helminths.

Agricultural livestock include, for example, mammals, such as, sheep, goats, horses, donkeys, camels, buffaloes, rabbits, reindeers, fallow deers, and in particular cattle and pigs; or poultry, such as turkeys, ducks, geese, and in particular chickens; or fish or crustaceans, e.g. in aquaculture.

Domestic animals include, for example, mammals, such as hamsters, guinea pigs, rats, mice, chinchillas, ferrets or in particular dogs, cats; cage birds; reptiles; amphibians or aquarium fish.

The present invention also provides methods of treating helminth infections, particularly gastro-intestinal and extra-intestinal helminth infections, more particularly gastro-intestinal and extra-intestinal infections with nematodes.

These disorders have been well characterized in animals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as a nematode infection. In particular, and particularly in the animal health or veterinary field, the term "treating" or "treatment" includes prophylactic, metaphylactic or therapeutical treatment Helminths pathogenic for humans or animals include, for example, acanthocephala, nematodes, pentastoma and platyhelmintha (e.g. monogenea, cestodes and trematodes).

Exemplary helminths include, without any limitation:

Monogenea: e.g.: *Dactylogyrus* spp., *Gyrodactylus* spp., *Microbothrium* spp., *Polystoma* spp., *Troglocephalus* spp.

Cestodes: from the order of the Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

from the order of the Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of the Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of the Trichinellida, for example: *Capillaria* spp., *Eucoleus* spp., *Paracapillaria* spp., *Trichinella* spp., *Trichomosoides* spp., *Trichuris* spp.

from the order of the Tylenchida, for example: *Micronema* spp., *Parastrongyloides* spp., *Strongyloides* spp.

from the order of the Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

from the order of the Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acantocephala: from the order of the Oligacanthorhynchida, for example: *Macracanthorhynchus* spp., *Prosthenorchis* spp.; from the order of the Moniliformida, for example: *Moniliformis* spp.

from the order of the Polymorphida, for example: *Filicollis* spp.; from the order of the Echinorhynchida, for example: *Acanthocephalus* spp., *Echinorhynchus* spp., *Leptorhynchoides* spp.

Pentastoma: from the order of the Porocephalida, for example: *Linguatula* spp.

The compounds of the present invention can be used in particular in therapy and prevention, i.e. prophylaxis, of helminth infections, particularly gastro-intestinal and extra-intestinal helminth infections, more particularly gastro-intestinal and extra-intestinal infections with nematodes.

By using the compounds of the present invention to control animal parasites, in particular helminths, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling", as used herein with regard to the animal health field, means that the compounds of the present invention are effective in reducing the incidence of the respective parasite in an animal infected with such parasites to innocuous levels. More specifically, "controlling", as used herein, means that the compounds of the present invention are effective in killing the respective parasite, inhibiting its growth, or inhibiting its proliferation.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prevention of diseases, in particular of helminth infections, particularly of gastro-intestinal and extra-intestinal helminth infections, more particularly of gastro-intestinal and extra-intestinal infections with nematodes.

The pharmaceutical activity of the compounds according to the invention can be explained by their interaction with the Slo-1 ion channel.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prevention of diseases, in particular of helminth infections, particularly of gastro-intestinal and extra-intestinal helminth infections, more particularly of gastro-intestinal and extra-intestinal infections with nematodes.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prevention of diseases, in particular of helminth infections, particularly of gastro-intestinal and extra-intestinal helminth infections, more particularly of gastro-intestinal and extra-intestinal infections with nematodes.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prevention or treatment of diseases, in particular of helminth infections, particularly of gastro-intestinal and extra-intestinal helminth infections, more particularly of gastro-intestinal and extra-intestinal infections with nematodes.

In accordance with a further aspect, the present invention covers a method of treatment or prevention of diseases, in particular of helminth infections, particularly of gastro-intestinal and extra-intestinal helminth infections, more particularly of gastro-intestinal and extra-intestinal infections with nematodes, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use as an antiendoparasitical agent.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use as a anthelmintic agent, in particular for use as a nematicidal agent, a platyhelminthicidal agent, an acanthocephalicidal agent, or a pentastomicidal agent.

In accordance with a further aspect, the present invention covers pharmaceutical compositions, in particular a veterinary formulation, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

In accordance with a further aspect, the present invention covers a method for preparing a pharmaceutical composition, in particular a veterinary formulation, comprising the step of mixing a compound of general formula (I), as described supra, or a stereoisomer, a tautomer, an N-oxide, a hydrate, a solvate, a salt thereof, particularly a pharmaceutically acceptable salt, or a mixture of same, with one or more excipients), in particular one or more pharmaceutically acceptable excipient(s).

In accordance with a further aspect, the present invention covers a method of treatment or prevention of diseases, in particular of helminth infections, particularly of gastro-intestinal and extra-intestinal helminth infections, more particularly of gastro-intestinal and extra-intestinal infections with nematodes, using a pharmaceutical composition, in particular a veterinary formulation, comprising an effective amount of a compound of general formula (I), as described supra, or stereoisomers, tautomers, N-oxides, hydrates, solvates, and salts thereof, particularly pharmaceutically acceptable salts thereof, or mixtures of same.

The present invention furthermore covers pharmaceutical compositions, in particular veterinary formulations, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent. Such administration can be carried out prophylactically, methaphylactically or therapeutically.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, chewables (for example soft chewables), powders, emulsions, suspensions, aerosols or solutions.

It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, spot-ons, dusting powders, implants or stents.

The compounds according to the invention can be incorporated into the stated administration forms. This can be effected in a manner known per se by mixing with pharmaceutically suitable excipients.

Pharmaceutically suitable excipients include, inter alia,

- fillers and carriers (for example cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, isopropanol, glycerol, propylene glycol, medium chain-length triglycerides fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®),
- buffers, acids and bases (for example phosphates, carbonates, citric acid, acetic acid, hydrochloric acid, sodium hydroxide solution, ammonium carbonate, trometamol, triethanolamine),
- isotonicity agents (for example glucose, sodium chloride),
- adsorbents (for example highly-disperse silicas),
- viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine),
- disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)),
- flow regulators, lubricants, glidants and mould release agents (for example magnesium stearate, stearic acid, talc, highly-disperse silicas (such as, for example, Aerosil®)),
- coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)),
- capsule materials (for example gelatine, hydroxypropylmethylcellulose),
- synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers),
- plasticizers (for example polyethylene glycols, propylene glycol, glycerol, triacetine, triacetyl citrate, dibutyl phthalate),
- penetration enhancers,
- stabilisers (for example antioxidants such as, for example, ascorbic acid, ascorbyl palmitate, sodium ascorbate, butylhydroxyanisole, butylhydroxytoluene, propyl gallate),
- preservatives (for example parabens, sorbic acid, thiomersal, benzalkonium chloride, chlorhexidine acetate, sodium benzoate),
- colourants (for example inorganic pigments such as, for example, iron oxides, titanium dioxide),
- flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prevention of an endo- and/or ectoparasiticidal infection.

The term "endoparasite" in the present invention is used as known to persons skilled in the art, and refers in particular to helminths. The term "ectoparasite" in the present invention is used as known to persons skilled in the art, and refers in particular to arthropods, particularly insects or acarids.

Particularly, the present invention covers a pharmaceutical combination, in particular a veterinary combination, which comprises:
- one or more first active ingredients, in particular compounds of general formula (I) as defined supra, and
- one or more further active ingredients, in particular one or more endo- and/or ectoparasiticides.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known ectoparasiticides and/or endoparasiticides.

The other or further active ingredients specified herein by their common names are known and described, for example, in the Pesticide Manual ("The Pesticide Manual" 16th Ed., British Crop Protection Council 2012) or can be searched in the internet (e.g. http://www.alanwood.net/pesticides). The classification is based on the current IRAC Mode of Action Classification Scheme at the time of filing of this patent application.

Examples of ectoparasiticides and/or endoparasiticides are insecticides, acaricides and nematicides, and include in particular:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCI) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(9) Modulators of Chordotonal Organs, such as, for example pymetrozine or flonicamid.

(10) Mite growth inhibitors, such as, for example clofentezine, hexythiazox and diflovidazin or etoxazole.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, noviflumuiron, teflubenzuron and triflumuron.

(16) Inhibitors of chitin biosynthesis, type I, for example buprofezin.

(17) Moulting disruptor (in particular for Diptera, i.e. dipterans), such as, for example, cyromazine.

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(25) Mitochondrial complex II electron transport inhibitors, such as, for example, beta-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide, further active ingredients such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide. Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tioxazafen, Thiofluoximate, Triflumezopyrim and iodomethane; furthermore preparations based on *Bacillus firmus* (I-1582, BioNeem, Votivo), and also the following compounds: 1-(2-fluoro-4-methyl-5-[(2,2,2-trifluoroethyl)sulphinyl]phenyl)-3-(trifluoromethyl)-1H-1,2,4-triazole-5-amine (known from WO2006/043635) (CAS 885026-50-6), 1'-[(2E)-3-(4-chlorophenyl)prop-2-en-1-yl]-5-fluorospiro[indol-3,4'-piperidin]-1(2H)-yl)(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl) phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl) benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]-propanamide, (+)-N-[3-chloro-1-(3-pyridinyl)-1H-pyrazol-4-yl]-N-ethyl-3-[(3,3,3-trifluoropropyl)sulfinyl]-propanamide and (−)-N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl) phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino) thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3, 4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl) phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A)(CAS 1542271-46-4); (4aS)-7-chloro-2,5-dihydro-2-[[(methoxycarbonyl)[4-[(trifluoromethyl)thio] phenyl]amino]carbonyl]-indeno[1,2-e][1,3,4]oxadiazine-4a (3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy) phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-aza-bicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO2007040282 A1) (CAS 934001-66-8). N-[3-chloro-1-(3-pyridinyl)-1H-pyrazol-4-yl]-N-ethyl-3-[(3,3,3-trifluoropropyl)thio]-propanamide (known from WO 2015/058021 A1. WO 2015/058028 A1) (CAS 1477919-27-9), N-[4-(aminothioxomethyl)-2-methyl-6-[(methylamino) carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]-pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1,8-diazaspiro[4.5]dec-3-en-4-yl-carbonic acid ethyl ester (known from WO 2010/066780 A1, WO 2011151146 A1) (CAS 1229023-00-0), N-[1-[(6-chloro-3-pyridinyl)methyl]-2(1H)-pyridinylidene]-2,2,2-trifluoro-acetamide (known from DE 3639877 A1, WO 2012029672 A1) (CAS 1363400-41-2), [N(E)]-N-[1-[(6-chloro-3-pyridinyl)methyl]-2(1H)-pyridinylidene]-2,2,2-trifluoro-acetamide, (known from WO 2016005276 A1) (CAS 1689566-03-7), [N(Z)]—N-[1-[(6-chloro-3-pyridinyl)methyl]-2(1H)-pyridinylidene]-2,2,2-trifluoro-acetamide, (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1] nonane (known from WO 2011/105506 A1, WO2016/133011 A1) (CAS 1332838-17-1).

Active ingredients with unknown or non-specific mode of action, e.g., fentrifanil, fenoxacrim, cycloprene, chlorobenzilate, chlordimeform, flubenzimine, dicyclanil, amidoflumet, quinomethionate, triarathene, clothiazoben, tetrasul, potassium oleate, petroleum, metoxadiazone, gossyplure, flutenzin, bromopropylate, cryolite;

Active ingredients from other classes, e.g. butacarb, dimetilan, cloethocarb, phosphocarb, pirimiphos (-ethyl), parathion (-ethyl), methacrifos, isopropyl o-salicylate, trichlorfon, sulprofos, propaphos, sebufos, pyridathion, prothoate, dichlofenthion, demeton-S-methylsulphone, isazofos, cyanofenphos, dialifos, carbophenothion, autathiofos, aromfenvinfos (-methyl), azinphos (-ethyl), chlorpyrifos (-ethyl), fosmethilan, iodofenphos, dioxabenzofos, formothion, fonofos, flupyrazofos, fensulfothion, etrimfos;

organochlorines, e.g. camphechlor, lindane, heptachlor; or phenylpyrazoles, e.g. acetoprole, pyrafluprole, pyriprole, vaniiprole, sisapronil; or isoxazolines, e.g. sarolaner, afoxolaner, lotilaner, fluralaner;

pyrethroids, e.g. (cis-, trans-), metofluthrin, profluthrin, flufenprox, flubrocythrinate, fubfenprox, fenfluthrin, protrifenbute, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated carbonhydrogen compounds (HCHs);

neonicotinoids, e.g. nithiazine;

dicloromezotiaz, triflumezopyrim;

macrocyclic lactones, e.g. nemadectin, ivermectin, latidectin, moxidectin, selamectin, eprinomectin, doramectin, emamectin benzoate; milbemycin oxime;

triprene, epofenonane, diofenolan;

Biologicals, hormones or pheromones, for example natural products, e.g. thuringiensin, codlemone or neem components:

dinitrophenols, e.g. dinocap, dinobuton, binapacryl;

benzoylureas, e.g. fluazuron, penfluron;

amidine derivatives, e.g. chlormebuform, cymiazole, demiditraz;

Bee hive varroa acaricides, for example organic acids, e.g. formic acid, oxalic acid.

Non-limiting examples of insecticides and acaricides of particular interest for use in animal health are and include in particular [i.e. Mehlhom et al Encyclpaedic Reference of Parasitology 4$^{th}$ edition (ISBN 978-3-662-43978-4)]:

Effectors at arthropod ligand gated chloride channels: chlordane, heptachlor, endoculfan. Dieldrin, bromocyclen, toxaphene, lindane, fipronil, pyriprole, sisapronil, afoxolaner, fluralaner, sarolaner, lotilaner, fluxametamide, broflanilide, avermectin, doramectin, eprinomectin, ivermectin, milhemycin, moxidectin, selamectin;

Modulators of arthropod octopaminergic receptors: amitraz, BTS27271, cymiazole, demiditraz;

Effectors at arthropod voltage-gated sodium channels: DDT, methoxychlor, metaflumizone, indoxacarb, cinerin I, cinerin II, jasmolin I, jasmolin II, pyrethrin I, pyrethrin II, allethrin, alphacypermethrin, bioallethrin, betacyfluthrin, cyfluthrin, cyhalothrin, cypermethrin, deltamethrin, etofenprox, fenvalerate, flucythrinate, flumethrin, halfenprox, permethrin, phenothrin, resmethrin, tau-fluvalinate, tetramethrin;

Effectors at arthropod nicotinic cholinergic synapses (acetylcholine esterase, acetylcholine receptors): bromoprypylate, bendiocarb, carbaryl, methomyl, promacyl, propoxur, azamethiphos, chlorfenvinphos, chlorpyrifos, coumaphos, cythioate, diazinon, diclorvos, dicrotophos, dimethoate, ethion, famphur, fenitrothion, fenthion, heptenophos, malathion, naled, phosmet, phoxim, phtalofos, propetamphos, temephos, tetrachlorvinphos, trichlorfon, imidacloprid, nitenpyram, dinotefuran, spinosad, spinetoram;

Effectors on arthropod development processes: cyromazine, dicyclanil, diflubenzuron, fluazuron, lufenuron, triflumuron, fenoxycarb, hydroprene, methoprene, pyriproxyfen, fenoxycarb, hydroprene, S-methoprene, pyriproxyfen.

Exemplary active ingredients from the group of endoparasiticides, as a further or other active ingredient in the present invention, include, without limitation, anthelmintically active compounds and antiprotozoal active compounds.

Anthelmintically active compounds, including, without limitation, the following nematicidally, trematicidally and/or cestocidally active compounds:

from the class of macrocyclic lactones, for example: eprinomectin, abamectin, nemadectin, moxidectin, doramectin, selamectin, lepimectin, latidectin, milbemectin, ivermectin, emamectin, milbemycin;

from the class of benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole-sulphoxide, albendazole, flubendazole;

from the class of depsipeptides, preferably cyclic depsipetides, in particular 24-membered cyclic depsipeptides, for example: emodepside, PF1022A;

from the class of tetrahydropyrimidines, for example: morantel, pyrantel, oxantel;

from the class of imidazothiazoles, for example: butamisole, levamisole, tetramisole;

from the class of aminophenylamidines, for example: amidantel, deacylated amidantel (dAMD), tribendimidine;

from the class of aminoacetonitriles, for example: monepantel;

from the class of paraherquamides, for example: paraherquamide, derquantel;

from the class of salicylaniides, for example: tribromsalan, bromoxanide, brotianide, clioxanide, closantel, niclosamide, oxyclozanide, rafoxanide:

from the class of substituted phenols, for example: nitroxynil, bithionol, disophenol, hexachlorophene, niclofolan, meniclopholan;

from the class of organophosphates, for example: trichlorfon, naphthalofos, dichlorvos/DDVP, crufomate, coumaphos, haloxon;

from the class of piperazinones/quinolines, for example: praziquantel, epsiprantel;

from the class of piperazines, for example: piperazine, hydroxyzine;

from the class of tetracyclines, for example: tetracyclin, chlorotetracycline, doxycyclin, oxytetracyclin, rolitetracyclin;

from diverse other classes, for example: bunamidine, niridazole, resorantel, omphalotin, oltipraz, nitroscanate, nitroxynile, oxamniquine, mirasan, miracil, lucanthone, hycanthone, hetolin, emetine, diethylcarbamazine, dichlorophen, diamfenetide, clonazepam, bephenium, amoscanate, clorsulon.

Antiprotozoal active ingredients in the present invention, including, without limitation, the following active ingredients:

from the class of triazines, for example: diclazuril, ponazuril, letrazuril, toltrazuril; from the class of polylether ionophore, for example: monensin, salinomycin, maduramicin, narasin;

from the class of macrocyclic lactones, for example: milbemycin, erythromycin;

from the class of quinolones, for example: enrofloxacin, pradofloxacin;

from the class of quinines, for example: chloroquine;

from the class of pyrimidines, for example: pyrimethamine;

from the class of sulfonamides, for example: sulfaquinoxaline, trimethoprim, sulfaclozin;

from the class of thiamines, for example: amprolium;

from the class of lincosamides, for example: clindamycin;

from the class of carbanilides, for example: imidocarb;

from the class of nitrofuranes, for example: nifurtimox;

from the class of quinazolinone alkaloids, for example: halofuginon;

from diverse other classes, for example: oxamniquin, paromomycin;

from the class of vaccines or antigenes from microorganisms, for example: *Babesia canis* rossi, *Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All named other or further active ingredients in the present invention can, if their functional groups enable this, optionally form salts with suitable bases or acids.

Based upon standard laboratory techniques known to evaluate compounds useful for the treatment of helminth infections, by standard toxicity tests and by standard pharmacological assays for the determination of treatment of the conditions identified above in animals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the subject treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a subject is not dosed with a drug for a certain period of time, to be beneficial to the overall balance between pharmacological effect and tolerability. Furthermore, it is possible to have long-acting treatments, wherein the subject gets treated once for more than four weeks. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each subject will vary according to the nature and severity of the condition as determined by the attending diagnostician, the activity of the specific compound employed, the age and general condition of the subject, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

Abbreviations and Acronyms aq. aqueous
atm standard atmosphere
DAD diode array detector
DMF dimethylformamide
DMSO dimethyl sulfoxide
ELSD evaporative light scattering detector
ESI electrospray ionization
h hour(s)
LC-MS liquid chromatography-coupled mass spectrometry
min minute(s)
MTBE methyl-t.-butylether
NMR nuclear magnetic resonance spectrometry
p. page(s)
$R_t$ retention time
THF tetrahydrofuran
TLC thin layer chromatography The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or dichloromethane/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Analytical and Chromatography Methods

Analytical and Preparative Liquid Chromatography

Analytical (UP)LC-MS was performed by means of different equipments as described below. The masses (m/z) are reported from the positive mode electrospray ionisation unless the negative mode is indicated (ESI−).

LC-MS Method 0:

Measurement of log P values was performed according to EEC directive 79/831 Annex V.A8 by HPLC (High Performance Liquid Chromatography) on reversed phase columns with the following methods, instrument(s): Agilent 1100 LC system, Agilent MSD system, HTS PAL; Waters IClass Acquity UPLC, SQD2 (MS), PDA (LV).

[a] log P value is determined by measurement of LC-UV, in an acidic range, with 0.1% formic acid in water and acetonitrile as eluent (linear gradient from 10% acetonitrile to 95% acetonitrile).

[b] log P value is determined by measurement of LC-UV, in a neutral range, with 0.001 molar ammonium acetate solution in water and acetonitrile as eluent (linear gradient from 10% acetonitrile to 95% acetonitrile).

Calibration was done with straight-chain alkan-2-ones (with 3 to 16 carbon atoms) with known log P values (measurement of log P values using retention times with linear interpolation between successive alkanones).

Lambda-max-values were determined using UV-spectra from 200 nm to 400 nm and the peak values of the chromatographic signals.

M+1 (or M+H) means the molecular ion peak, plus or minus 1 a.m.u. (atomic mass unit) respectively, as observed in mass spectroscopy by electrospray ionization (ESI+ or −).

LC-MS Method 1:

MS instrument type: Agilent Technologies 6130 Quadrupole LC-MS; HPLC instrument type: Agilent Technologies 1260 Infinity; column: Waters XSelect (C18, 30×2.1 mm, 3.5μ); flow: 1 mL/min; column temp: 35° C.; eluent A: 0.1% formic acid in acetonitrile; eluent B: 0.1% formic acid in water; lin. gradient: t=0 min 5% A, t=1.6 min 98% A, t=3 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

LC-MS Method 2:

Instrument type: Waters ACQUITY SQD UPLC system; column: Waters Acquity UPLC HSS T3 1.8μ 50×1 mm; eluent A: 1 l water+0.25 ml formic acid, eluent B: 1 l acetonitrile+0.25 ml formic acid; gradient: 0.0 min 90% A→1.2 min 5% A→2.0 min 5% A oven: 50° C.; flow: 0.40 mil/min; UV-detection: 210 nm.

LC-MS Method 3:

MS instrument type: Agilent Technologies LC/MSD SL; HPLC instrument type: Agilent Technologies 1100 Series; column: Waters XSelect (C18, 30×2.1 mm, 3.5μ); flow: 1 mL/min; column temp: 25° C., eluent A: 95% acetonitrile+5% 10 mM ammoniumbicarbonate in water, eluent B: 10 mM ammoniumbicarbonate in water pH=9.0; lin. gradient: t=0 min 5% A, t=1.6 min 98% A, t=3 min 98% A; detection: DAD (220-320 nm); detection: MSD (ESI pos/neg) mass range: 100-800.

LC-MS Method 4:

Instrument type: Waters ACQUITY SQD UPLC System; column: Waters Acquity UPLC HSS T3 1.8μ 50×1 mm; eluent A: 1 l water+0.25 ml 99% ige formic acid, Eluent B: 1 l acetonitrile+0.25 ml 99% ige formic acid; gradient: 0.0 min 95% A→6.0 min 5% A→7.5 min 5% A oven: 50° C.; flow: 0.35 ml/min; UV-detection: 210 nm.

LC-MS LC-MS Method 5:

Instrument type: UPLC with SQD2 and Sample Manager from Waters, column: Zorbax Eclipse Plus C18, 50 mm×2.1 mm, 1.8 μm, eluent A: 1 l acetonitrile+1 ml formic acid, eluent B: 1 l water+0.9 ml formic acid; gradient 0.0 min 90% B→1.7 min 5% B→2.4 min 5% B DAD A: 210±4 nm, reference 360±50 nm, DAD A: 270±2 nm, reference 550±50 nm (only ketones), MSD, 100-1000 Amu, ES-ionisation, positive or negative.

$^1$H-NMR Data $^1$H-NMR data were determined with a Bruker Avance 400 (equipped with a flow cell (60 μl volume), or with a Bruker AVIII 400 equipped with 1.7 mm cryo CPTCI probe head, or with a Bruker AVIII 400 (400.13 MHz) equipped with a 5 mm probe head, or with a Bruker AVII 600 (600.13 MHz) equipped with a 5 mm cryo TCI probe head, or with a Bruker AVIII 600 (601.6 MHz) equipped with a 5 mm cryo CPMNP probe head, or with a Bruker AVIII 500 (500.13 MHz) equipped with a 5 mm broadband head or a 5 mm Prodigy™ probe head, or a Bruker Avance NEO 600 MHz (5 mm TC cryo probe head), with tetramethylsilane as reference (0.0) and the solvents $CD_3CN$, $CDCl_3$ or $D_6$-DMSO. Alternative $^1$H- and $^{13}$C-NMR instrument types: Bruker DMX300 ($^1$H-NMR: 300 MHz; $^{13}$C NMR: 75 MHz), Bruker Avance III 400 ($^1$H-NMR: 400 MHz; $^{13}$C NMR: 100 MHz) or Bruker 400 Ultrashield ($^1$H-NMR: 400 MHz; $^{13}$C NMR: 100 MHz).

Chemical shifts (δ) are displayed in parts per million [ppm]; the following abbreviations are used: s=singlet, d=doublet, t=triplet, q=quartet, m=multiplet, hr.=broad; coupling constants are displayed in Hertz [Hz].

Experimental Section—General Procedures

The synthesis of the compounds of the formula (I) can be performed according to or in analogy to the following schemes (Scheme 1, Scheme 2, Scheme 3, Scheme 4 and Scheme 5).

Scheme 1

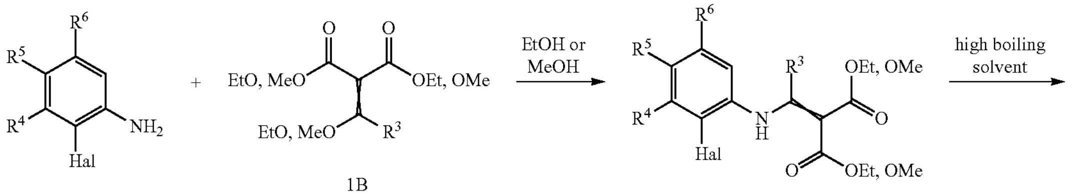

1A 1B 1C

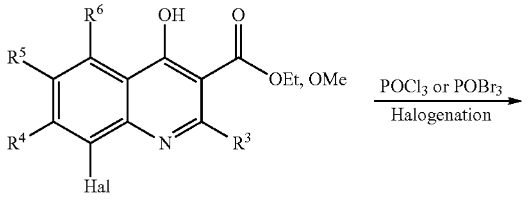

1D

-continued

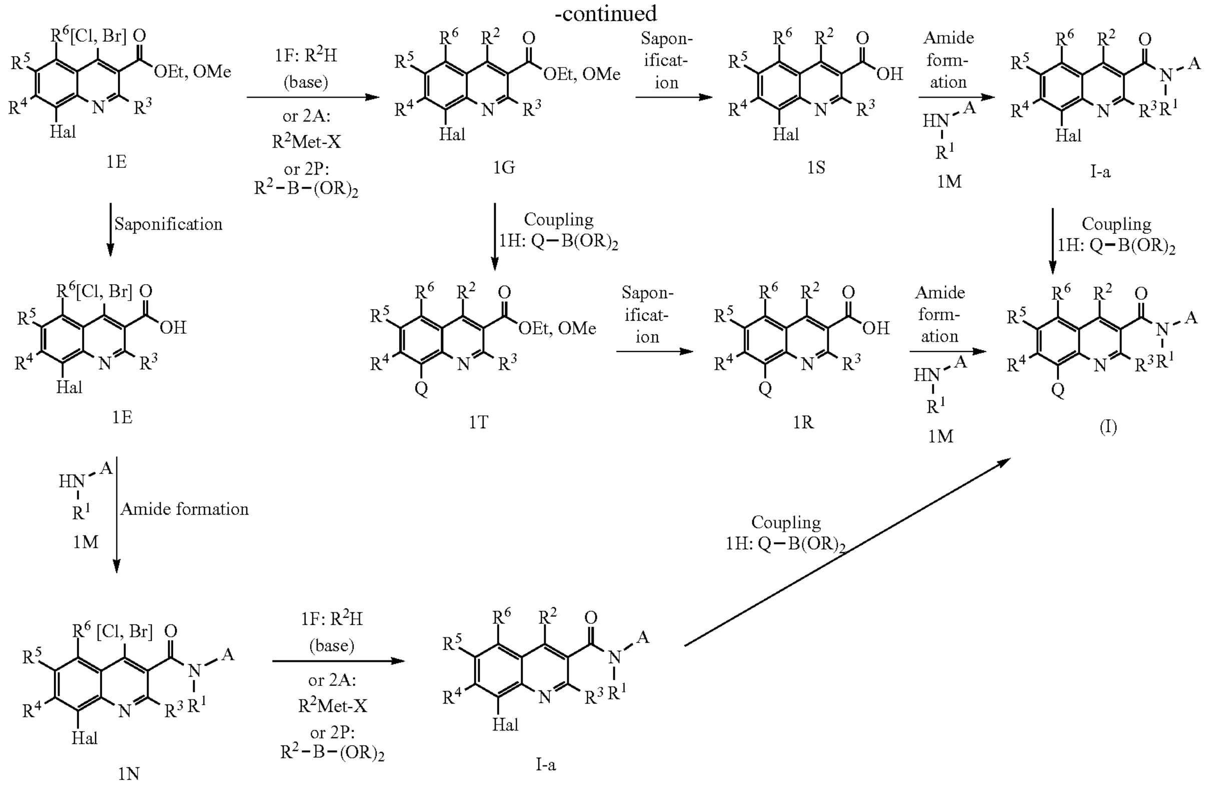

2-Halogen-substituted anilines 1A (Hal=iodine, bromine, chlorine) are commercially available and can be readily converted with (alkoxymethylen)malonates 1B dissolved the corresponding alcohol solvent, preferably under boiling conditions into (anitinomethylene)malonates 1C as described in Monatshefte fuer Chemie, 2015, 146(2), 291-302 or without any solvent as described in WO 2002004444. The ring closure is performed in high boiling solvents, preferably in diphenylether or xylol, to achieve hydroxy quinolines 1D as described in WO 2013118071. The hydroxy quinolines 1D can be easily converted into the corresponding chlorine compounds 1E with a chlorination reagent, preferably refluxing $POCl_3$ as described in WO 2013118071.

Dependend on the nature of the nucleophile $R^2H$ 1F, the chloro quinolines 1E reacts with 1F in the presence of a base, e.g. sodium ethylate, sodium methylate, potassium t-butylate, triethylamine N,N-diisopropyl ethylamine, diazabicycloundectin, sodium hydride, lithium hydroxide, sodium hydroxide, potassium hydroxide, potassium carbonate, cesium carbonate, or the like to obtain ester intermediates 1G. Dependend on the metal-organic reagent 2A and the halogen, the halogenoquinolines 1E react with zinc reagents, if necessary in the presence of a catalyst, e.g. cobalt salts as described in Tetrahedron Letters 39 (1998), p. 6163-6166, or Grignard reagents or boronic acids or their esters 2P (R═H; R=Me or R,R=pinacolate) in the presence of a palladium catalysts as described in Angew. Chem., 2014, vol. 126, p. 12975-12978 or European Journal of Medicinal Chemistry; vol. 147; (2018); p. 238-252 to afford intermediates 1G.

The ester intermediates 1G can be easily hydrolyzed to the corresponding acids 1S with e.g. aqueous sodium hydroxide or lithium hydroxide in appropriate solvents such as alcohols or cyclic ethers. The acids 1S can be reacted with commercial available amines 1M via an amide formation and dehydration reagents, e.g. N-(3-dimethylaminoisopropyl)-N'-ethylcarbodiimide-hydrochloride (EDC) or 2,4,6-tripropyl-1,3,5,2,4,6-trioxatriphosphinane 2,4,6-trioxide to give amides I-a. Similar syntheses are described in Journal of Medicinal Chemistry 2012, 55, p. 3563-3567 or Chem. Commun. 1999, p. 1847-1848 for example.

A Suzuki cross coupling reaction of intermediate carboxamides I-a with boronic acids or boronic esters 1H Q-B$(OR)_2$ (R═H; R=Me or R,R=pinacolate) as described in Chem. Soc. Rev. 2014, 43, p. 412-443 or in Tetrahedron 2002, 58 (48), p. 9633-9695 leads to the final products of formula (I).

The acids 1R can be reacted with commercially available amines 1M via an amide formation and dehydration reagents, e.g. N-(3-dimethylaminoisopropyl)-N'-ethylcarbodiimide-hydrochloride (EDC) or 2,4,6-tripropyl-1,3,5,2,4,6-trioxatriphosphinane 2,4,6-trioxide to give amides 1N. Similar syntheses are described in Journal of Medicinal Chemistry 2012, 55, p. 3563-3567 or Chem. Commun. 1999, p. 1847-1848, for example. The halogeno intermediates 1N can be coupled with olefinic boronic esters 2P (R=Me or R,R=pinacolate) in presence of a palladium catalyst, as e.g. reported in WO 200537826. The olefinic residues can be hydrogenated under standard conditions e.g. with hydrogen over palladium on charcoal to (I). If further reductions occur on the quinoline core, such reductions products e.g. dihydoquinoline intermediates can be reoxidised to the quinolone by, eg. cerium-(IV)-salts in appropriate solvents e.g. mixtures of DMSO and water or acetonitrile and water to furnish (I).

A Suzuki cross coupling reaction of ester intermediates 1G with boronic acids or boronic esters 1H Q-B$(OR)_2$ (R═H; R=Me or R,R=pinacolate) as described in Chem.

Soc. Rev. 2014, 43, p. 412-443 or in Tetrahedron 2002, 58 (48), p. 9633-9695, leads to the ester intermediates 1T, which can be subsequently hydrolyzed to the corresponding acids 1R with e.g. aqueous sodium hydroxide or lithium hydroxide in appropriate solvents such as alcohols or cyclic ethers.

amide formation and dehydration reagents, e.g. N-(3-dimethylaminoisopropyl)-N'-ethylcarbodiimide-hydrochloride (EDC) or 2,4,6-tripropyl-1,3,5,2,4,6-trioxatriphosphinane 2,4,6-trioxide to give amides 1N. Similar syntheses are described in Journal of Medicinal Chemistry 2012, 55, p. 3563-3567 or Chem. Commun. 1999, p. 1847-1848 for Scheme 2

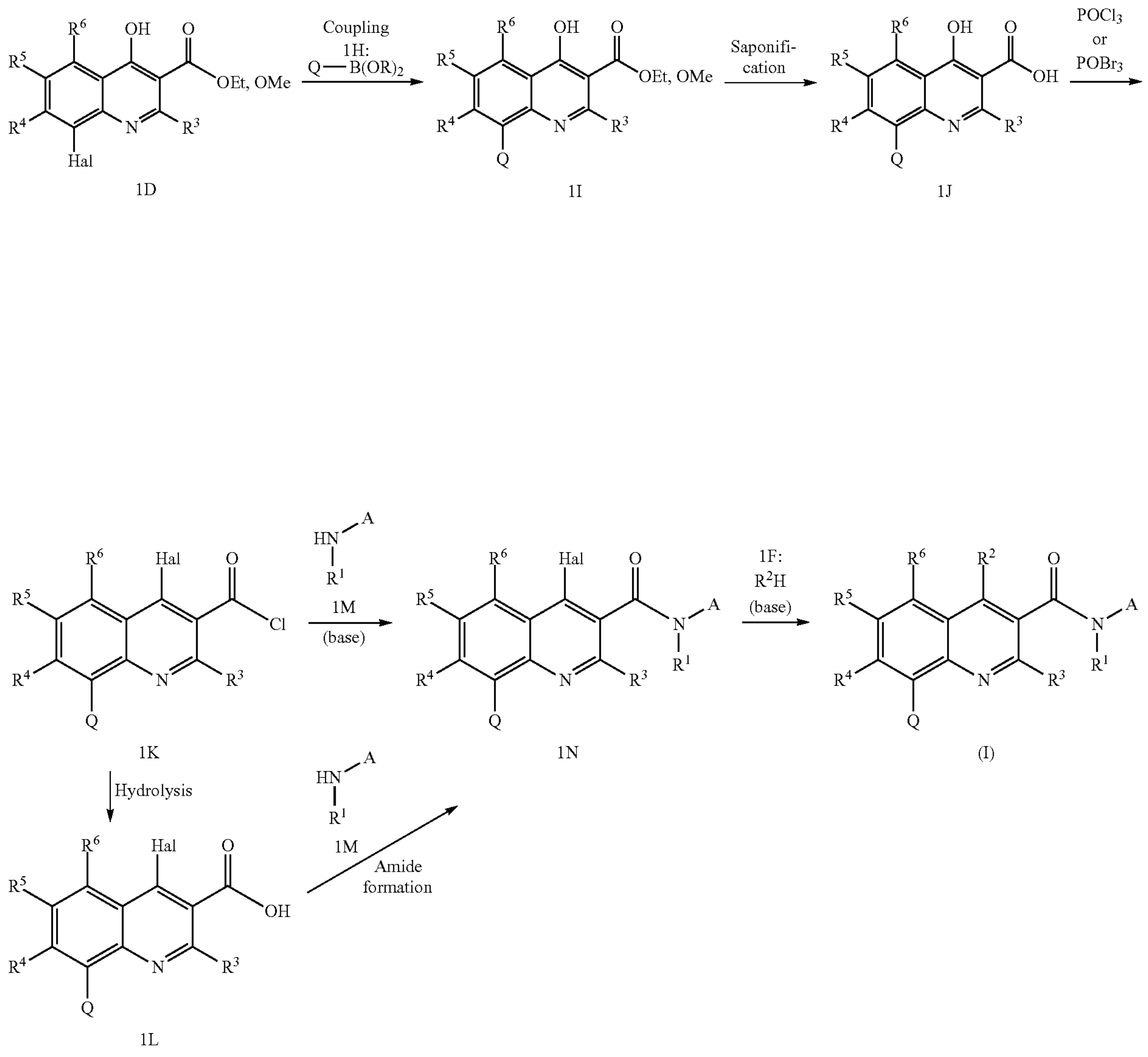

Alternatively, a Suzuki cross coupling reaction of intermediates 1D with boronic acids or boronic esters 1H Q-B (OR). (R═H; R=Me or R,R=pinacolate) as described in Chem. Soc. Rev. 2014, 43, p. 412-443 or in Tetrahedron 2002, 58 (48), p. 9633-9695 to ester intermediates 1I. Subsequently, the ester intermediates 1I can be smoothly saponified e.g. with sodium hydroxide or lithium hydroxide resulting in the corresponding carboxylic acids 1J, which can be easily converted into the corresponding chloro carboxylic chlorides 1K with a halogenation reagent, e.g. $POCl_3$ or $POBr_3$, preferably refluxing $POCl_3$ as described in WO 2013096151. Intermediates 1K react under hydrolytic conditions to yield quinoline carboxylic acids 1L, which are combined with commercial available amines 1M via an example. Intermediates 1K can directly form the amides 1N as the carboxylic acid chlorides 1K are combined with amines 1M under basic conditions, e.g. pyridine, triethylamine or N,N-diisopropyl ethylamine as described in Chemical Biology & Drug Design 2015, 85(5), p. 549-564.

Dependend on the nature of the nucleophile $R^2H$ 1F, the chloro quinolines 1N reacts with 1F in the presence of a base, e.g. sodium ethylate, sodium methylate, potassium t-butylate, triethylamine N,N-diisopropyl ethylamine, diazabicycloundecan, sodium hydride, lithium hydroxide, sodium hydroxide, potassium hydroxide, potassium carbonate, cesium carbonate, or the like to obtain the target compounds of formula (I).

Scheme 3

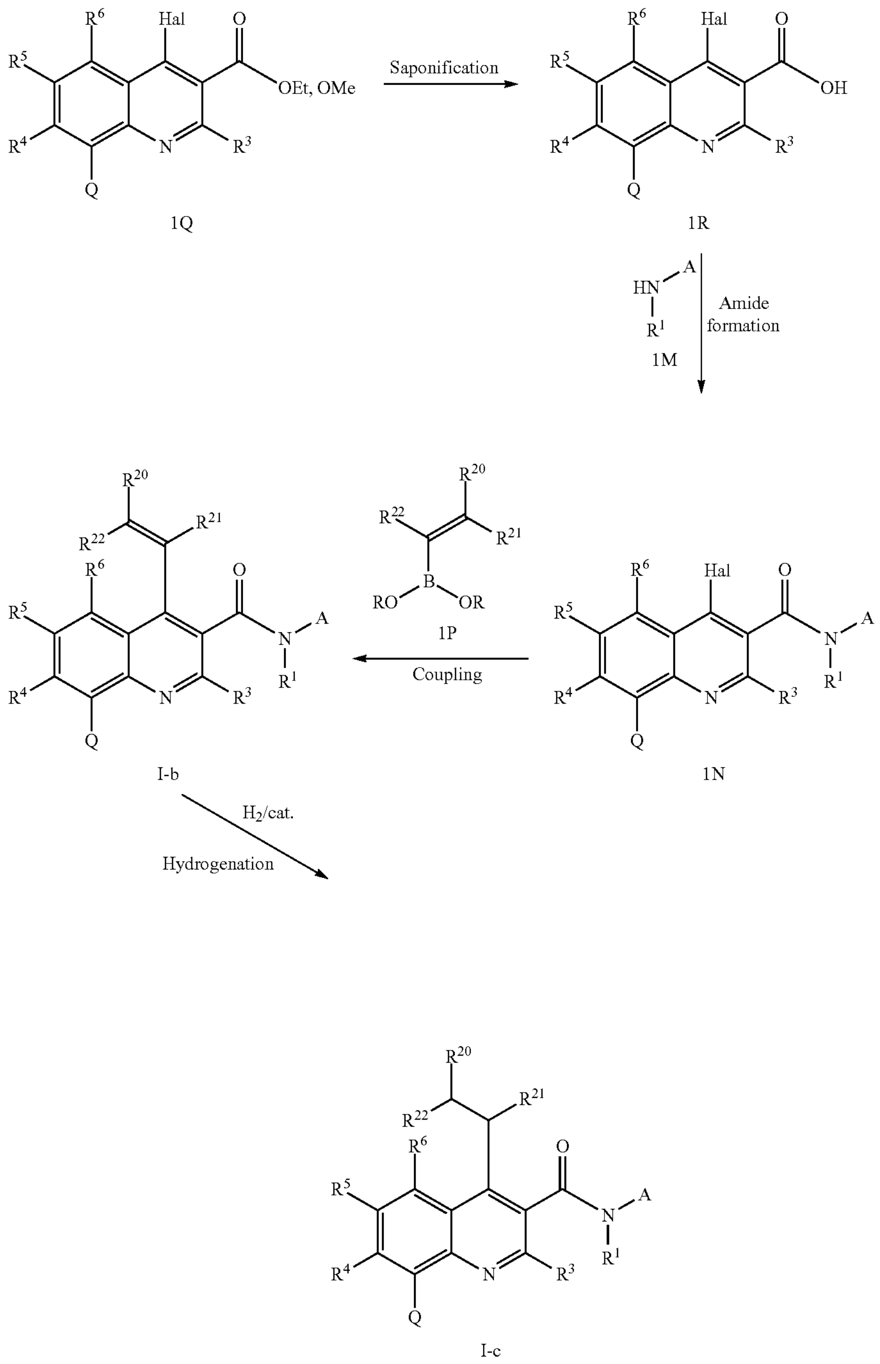

1Q 1R 1M 1P I-b 1N I-c

Ester intermediates 1Q can be easily hydrolyzed to the corresponding acids tR with e.g. aqueous sodium hydroxide or lithium hydroxide in appropriate solvents such as alcohols or cyclic ethers. The acids 1R can be reacted with commercially available amines 1M via an amide formation and dehydration reagents, e.g. N-(3-dimethylaminoisopropyl)-N'-ethylcarbodiimide-hydrochloride (EDC) or 2,4,6-tripropyl-1,3,5,2,4,6-trioxatriphosphinane 2,4,6-trioxide to give amides 1N. Similar syntheses are described in Journal of Medicinal Chemistry 2012, 55, p. 3563-3567 or Chem. Commun. 1999, p. 1847-1848, for example. The halogen intermediates 1N can be coupled with olefinic boronic esters 1P (R=Me or R,R=pinacolate; $R^{21}$, $R^{22}$, $R^{23}$ are $C_1$-$C_3$alkyl or form a dihydropyranyl ring) in presence of a palladium catalyst, as e.g. reported in WO 200537826. The olefinic residues can be hydrogenated under standard conditions e.g. with hydrogen over palladium on charcoal to (I). If further reductions occur on the quinoline core, such reductions products e.g. dihydoquinoline intermediates can be reoxidised to the quinolone by, eg. cerium-(IV)-salts in appropriate solvents e.g. mixtures of DMSO and water or acetonitrile and water to furnish (I).

Scheme 4

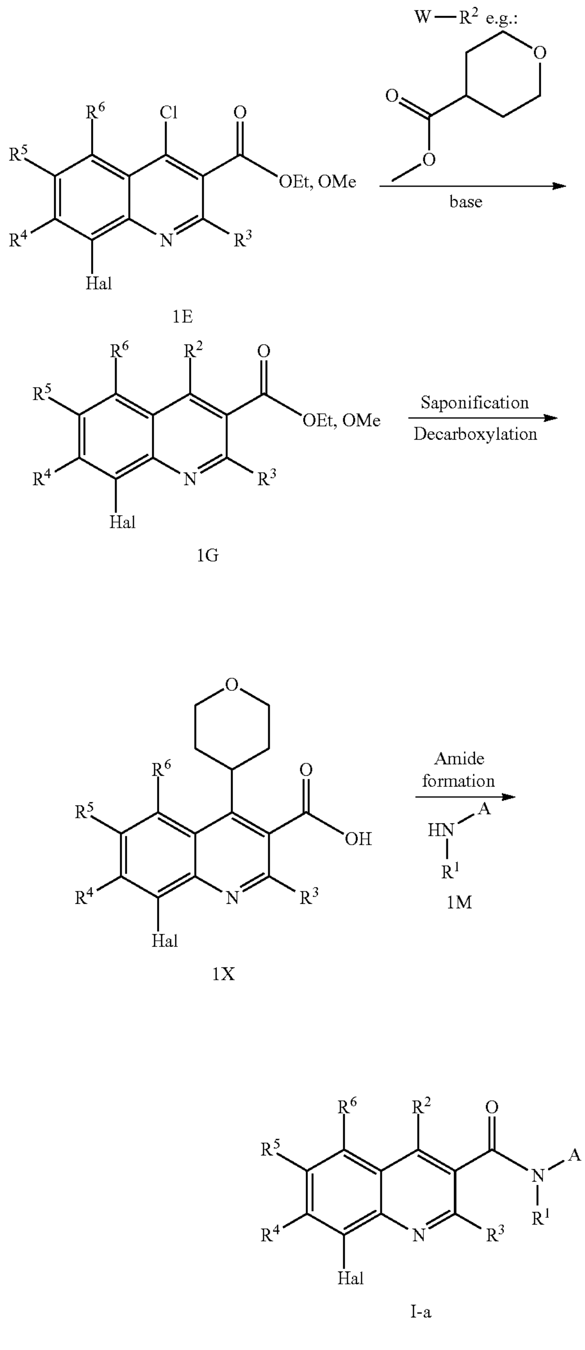

Alternatively, chloroquinolines 1E can be substituted in the presence of a base, e.g. lithium hexamethylsilazane, sodium hydride or potassium tert.-butylate with groups, W—$R^2$, if $R^2$ bears at least one hydrogen atom and W is an CH-activating group e.g. an ester or a cyano group leading to 1G. Analogous reactions are described for instance in Org. Proc. Res, and Dev. 2001, 5, p. 28-36 or in WO 2013174780. During saponification of esters 1G the group W can be split off by a saponification and decarboxylation sequence leading to acids 1X. From the acids 1X the amide intermediates I-a can be easily obtained by amide formation reactions as described above.

Scheme 5

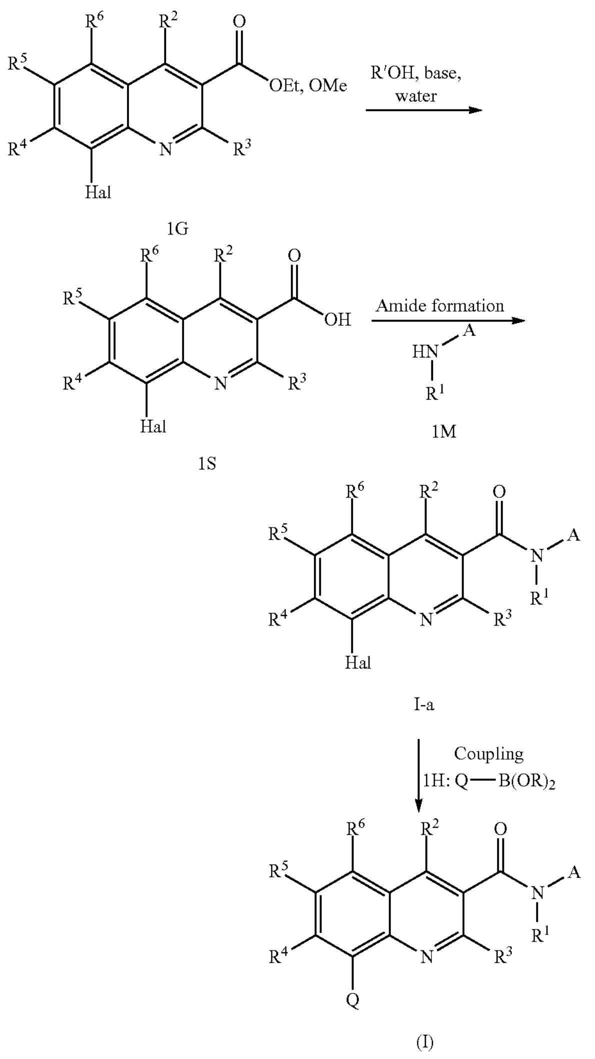

Alternatively, 7-fluoroquinolines 1G ($R^4$=F) can be converted to 7-alkoxy-quinoline carboxylic acids 1S ($R^4$=$C_1$-$C_4$-alkoxy) by treatment with an alcohol, base and some water at elevated temperatures.

The final products (I) can be synthesized by the same reactions as described above.

In the schemes 1 to 5 described above Q, A, $R^1$, $R^2$, $R^3$, $R^4$, $R^5$ and $R^6$ have the meaning as defined supra, unless explicitly described otherwise.

NMR Peak Lists

NMR peak forms are stated as they appear in the spectra, possible higher order effects have not been considered.

$^1$H-NMR data of selected examples are written in form of $^1$H-NMR peak lists. To each signal peak are listed the δ-value in ppm and the signal intensity in round brackets. Between the δ-value—signal intensity pairs are semicolons or commas as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$) or $\delta_1$ (intensity$_1$), $\delta_2$ (intensity$_2$), . . . ; $\delta_i$ (intensity$_i$), . . . , $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}H$ spectra, we use tetramethylsilane and/or the chemical shift of the solvent used, especially in the case of spectra measured in DMSO. Therefore in NMR peak lists, tetramethylsilane peak can occur but not necessarily.

The $^{1}H$-NMR peak lists are similar to classical $^{1}H$-NMR prints and contains therefore usually all peaks, which are listed at classical NMR-interpretation.

Additionally they can show like classical $^{1}H$-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}H$-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}H$-NMR interpretation.

Further details of NMR-data description with peak lists you find in the publication "Citation of NMR Peaklist Data within Patent Applications" of the Research Disclosure Database Number 564025.

Intermediates

Intermediate 1A

4-Hydroxy-8-(2,3,5-trifluorophenyl)quinoline-3-carboxylic acid

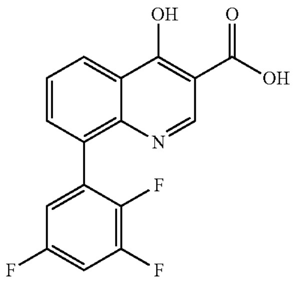 [SMILES: O=C(O)c1cnc2c(-c3cc(F)cc(F)c3F)cccc2c1O]

A mixture of ethyl 8-bromo-4-hydroxyquinoline-3-carboxylate (5.00 g, 16.89 mmol) (Zask, al. Bioorganic and Medicinal Chemistry Letters, 2003, 1487-1490; Gharat, al. WO/2013/118071), (2,3,5-trifluorophenyl)boronic acid (3.56 g, 20.26 mmol) and potassium fluoride (2.94 g, 50.70 mmol) in tetrahydrofuran (50 mL) and water (5 mL) was sparged with nitrogen for 10 min. After the addition of tris(dibenzylideneacetone)dipalladium(0) (0.77 g, 0.84 mmol) and tri-tert-butylphosphine tetrafluoroborate (0.49 g, 1.69 mmol), the reaction mixture was sparged with nitrogen for 10 min and was stirred at 75° C. for 18 h. Then water (25 mL) and lithium hydroxide monohydrate (3.54 g, 84 mmol) were added and the reaction mixture was stirred at 90° C. for 4 h. After the addition of water (35 mL) and lithium hydroxide monohydrate (3.54 g, 84 mmol), stirring at 90° C. was continued for 18 h. The reaction mixture was allowed to cool to room temperature. Activated charcoal (2 g) was added and the mixture was stirred for 1 h. Solids were filtered off over a pad of kieselguhr. The filter cake was washed with aqueous sodium hydroxide (1 M; 3×30 ml) and tetrahydrofuran (3×30 mL). The filtrate was slowly added to hydrochloric acid (1 M; 300 mL). The resulting suspension was stirred for 30 min. The precipitate was filtered off, washed with water and diethyl ether and was dried on air. 5.33 g (99% of theory) of the title compound were obtained.

LC-MS (Method 1): $R_t$=1.92 min; m/z=320 $(M+H)^+$ $^{1}H$-NMR (400 MHz, DMSO-d6) δ 15.11 (s, 1H), 12.35 (s, 1H), 8.58 (s, 1H), 8.46 (dd, 1H), 7.91 (dd, 1H), 7.86-7.77 (m, 1H), 7.73 (t, 1H), 7.44-7.36 (m, 1H).

Intermediate 2A

4-Chloro-8-(2,3,5-trifluorophenyl)quinoline-3-carbonyl chloride

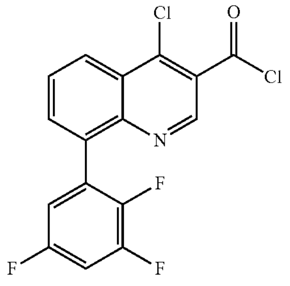 [SMILES: O=C(Cl)c1cnc2c(-c3cc(F)cc(F)c3F)cccc2c1Cl]

Under nitrogen atmosphere 4-hydroxy-8-(2,3,5-trifluorophenyl)quinoline-3-carboxylic acid (5.33 g, 17 mmol) was added to phosphorus oxychloride (8.0 mL, 86 mmol) at room temperature. The suspension was stirred at 110° C. for 2.5 h. The reaction mixture was allowed to cool to room temperature. Volatiles were removed in vacuo at 40° C. The residual black oil was stored under argon and was used as such.

LC-MS (Method 1): $R_t$=2.24 min; m/z=352 $(M+H)^+$ [for corresponding methyl ester]

Intermediate 3A

4-Chloro-N-[(4S)-3,4-dihydro-2H-chromen-4-yl]-8-(2,3,5-trifluorophenyl)quinoline-3-carboxamide

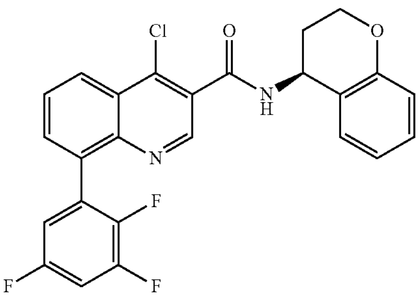 [SMILES: O=C(N[C@H]1CCOc2ccccc21)c1cnc2c(-c3cc(F)cc(F)c3F)cccc2c1Cl]

Under argon atmosphere at 0° C., to a solution of crude 4-chloro-8-(2,3,5-trifluorophenyl)quinoline-3-carbonyl chloride (17 mmol) in dry tetrahydrofuran (30 mL) was added N,N-diisopropylethylamine (15 mL, 84 mmol). The mixture was stirred for 10 min and (S)-chroman-4-amine hydrochloride (3.13 g, 17 mmol) was added in portions. The reaction mixture was allowed to warm to room temperature and was stirred for 74 h. Activated charcoal (2 g) was added and the mixture was stirred for 30 min. Solids were filtered off over a pad of kieselgur. The filter cake was washed with tetrahydrofuran (3×30 mL). At 0° C., the filtrate was slowly added to hydrochloric acid (1 M; 150 mL). The resulting suspension was stirred for 30 min. Solids were filtered off, washed with water, diisopropyl ether and methyl-tert-butyl ether and were dried on air. 5.41 g (69% of theory) of the title compound were obtained.

LC-MS (Method 3): $R_t$=2.21 min; m/z=469/471 $(M+H)^+$

1H NMR (400 MHz, DMSO-d6) δ 9.29 (d, 1H), 8.93 (s, 1H), 8.45 (dd, 1H), 8.02-7.91 (m, 2H), 7.74-7.56 (m, 1H), 7.38 (dd, 1H), 7.34-7.26 (m, 1H), 7.18 (td, 1H), 6.93 (td, 1H), 6.80 (dd, 1H), 5.28 (dt, 1H), 4.33-4.20 (m, 2H), 2.27-2.17 (m, 1H), 2.12-2.02 (m, 1H).

Intermediate 4A

Ethyl 8-bromo-4-[4-(methoxycarbonyl)tetrahydro-2H-pyran-4-yl]quinoline-3-carboxylate

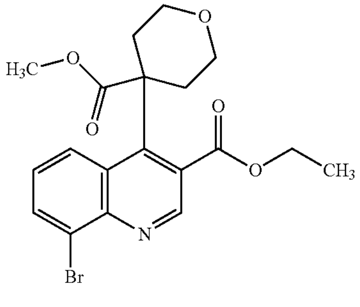 [SMILES: CCOC(=O)c1cnc2c(Br)cccc2c1C1(C(=O)OC)CCOCC1]

Under argon a solution of methyl tetrahydro-2H-pyran-4-carboxylate (3.2 ml, 24 mmol) in THF (32 ml) was treated at −5° C. with bis-(trimethylsilyl)-lithiumamide (29 ml, 1.0 M solution in THF, 29 mmol) and stirred at −5 to 0° C. for 10 min. Then solid ethyl 8-bromo-4-chloroquinoline-3-carboxylate (5.0 g, 15.9 mmol) (Zask, al. Bioorganic and Medicinal Chemistry Letters, 2003, 1487-1490; Gharat, al. WO/2013/118071) was added in portions at this temperature and stirring continued at −5° C. for 30 min. The reaction mixture was allowed to warm to room temperature. After 45 min the mixture was added in portions to a stirred mixture of water (250 ml) and acetic acid (3.3 ml, 58 mmol). The THF was removed by evaporation under diminished pressure and the aqueous mixture extracted with ethylacetate. The organic phase was dried and evaporated. The residue was purified by flash chromatography on silica (100 g) with cyclohexane/ethylacetate (12-17%).

Yield: 5.44 g (98% pure, 79% of theory)

LC-MS (Method 2): $R_t$=1.07 min; MS (ESIpos): m/z=422 $[M+H]^+$ $^1$H-NMR (400 MHz, DMSO-d6) δ [ppm]: 1.357 (6.88), 1.375 (14.95), 1.393 (7.58), 1.397 (4.39), 2.179 (0.88), 2.200 (1.86), 2.213 (1.51), 2.220 (1.36), 2.233 (2.39), 2.254 (1.26), 2.414 (3.29), 2.447 (2.46), 3.310 (16.00), 3.820 (6.73), 3.838 (6.62), 3.966 (0.97), 4.110 (1.06), 4.431 (2.21), 4.449 (6.96), 4.467 (6.93), 4.485 (2.15), 5.755 (2.36), 7.591 (2.17), 7.610 (2.77), 7.613 (2.73), 7.632 (2.40), 8.184 (3.11), 8.205 (2.76), 8.206 (2.77), 8.224 (3.20), 8.242 (3.07), 8.911 (7.68).

Intermediate 5A

8-Bromo-4-(tetrahydro-2H-pyran-4-yl)quinoline-3-carboxylic acid

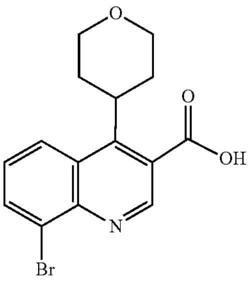 [SMILES: O=C(O)c1cnc2c(Br)cccc2c1C1CCOCC1]

Ethyl 8-bromo-4-[4-(methoxycarbonyl)tetrahydro-2H-pyran-4-yl]quinoline-3-carboxylate (845 mg, 2.0 mmol) was refluxed 2 d in isopropanol (8 ml) containing aqueous sodium hydroxide (2.4 ml, 5 M, 12 mmol). Water (15 ml) was added and hydrochloric acid (3 ml, 5 M, 15 mmol) dropwise at 50° C. The suspension formed was stirred 3 h at ambient temperature, the precipitate filtered off, washed with water/isopropanol (2:1) and dried in vacuo.

Yield: 691 mg (>100% of theory, crude material)

LC-MS (Method 4): $R_t$=1.88 min; MS (ESIpos): m/z=336 $[M+H]^+$ $^1$H-NMR (500 MHz, DMSO-d6) δ [ppm]: −0.007 (1.50), 0.006 (1.00), 1.034 (1.53), 1.046 (1.51), 1.678 (4.44), 1.699 (4.80), 2.348 (1.15), 2.357 (1.43), 2.373 (3.28), 2.381 (3.40), 2.398 (3.41), 2.406 (3.20), 2.423 (1.35), 2.431 (1.19), 3.526 (3.52), 3.547 (6.66), 3.570 (3.67), 3.906 (0.86), 3.913 (1.53), 3.920 (1.03), 3.931 (1.74), 3.938 (2.90), 3.945 (1.68), 3.955 (1.01), 3.962 (1.46), 3.970 (0.81), 3.998 (4.92), 4.006 (5.13), 4.021 (4.63), 4.029 (4.38), 7.606 (4.83), 7.621 (6.26), 7.623 (5.84), 7.638 (5.05), 8.223 (7.00), 8.225 (6.80), 8.238 (7.01), 8.525 (5.52), 8.542 (5.36), 8.685 (0.47), 8.987 (16.00), 13.845 (0.91).

Intermediate 6A

8-Bromo-N-[(4S)-3,4-dihydro-2H-chromen-4-yl]-4-(tetrahydro-2H-pyran-4-yl)quinoline-3-carboxamide

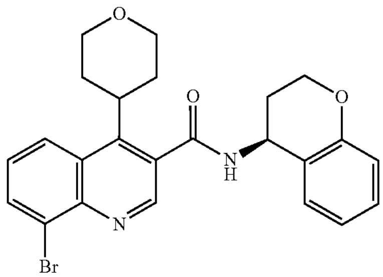 [SMILES: O=C(N[C@H]1CCOc2ccccc21)c1cnc2c(Br)cccc2c1C1CCOCC1]

A solution of 8-bromo-4-(tetrahydro-2H-pyran-4-yl)quinoline-3-carboxylic acid (690 mg, 2.05 mmol) in DMF/THF (1:3 mixture, 14 ml) was placed in an oil bath of 55° C., and treated with (4S)-chroman-4-amine hydrochloride (457 mg, 2.46 mmol) and N,N-diisopropylethylamine (1.4 ml, 8.2 mmol). The heating was removed and a solution of 2,4,6-tripropyl-1,3,5,2,4,6-trioxatriphosphinane 2,4,6-trioxide in ethylacetate (1.9 ml, 50% content, 3.3 mmol) was added dropwise and the mixture stirred over night at ambient temperature. The reaction mixture was warmed again to 55° C., (4S)-chroman-4-amine hydrochloride (152 mg, 0.82 mmol), N,N-diisopropylethylamine (0.5 ml, 2.87 mmol) was added and after removal of the heating a solution of 2,4,6-tripropyl-1,3,5,2,4,6-trioxatriphosphinane 2,4,6-trioxide in ethylacetate (0.6 ml, 50% content, 1.03 mmol) and stirring continued at ambient temperature for 3.5 h. Then water (80 ml) was added and the mixture stirred at 60° for 20 min. The THF was removed under reduced pressure and the mixture cooled to RT. The precipitate was filtered off, washed with water and dried in vacuo.

Yield: 748 mg (78% of theory)

LC-MS (Method 2): $R_t$=0.97 min; MS (ESIneg): m/z=465 $[M]^-$ $^1$H-NMR (500 MHz, DMSO-d6) δ [ppm]: 1.351 (0.58), 1.644 (3.27), 1.670 (3.71), 1.686 (3.38), 1.713 (3.35), 1.755 (1.16), 1.988 (0.44), 2.060 (2.11), 2.070 (2.36), 2.084 (2.76), 2.229 (2.51), 2.240 (2.55), 2.246 (2.47), 2.257 (1.85), 2.377 (4.33), 2.401 (4.40), 2.632 (0.47), 3.296 (0.44), 3.393 (1.42), 3.440 (1.96), 3.461 (3.53), 3.495 (2.87), 3.519 (4.15), 3.541 (2.36), 3.598 (1.27), 3.697 (2.22), 3.988 (5.45), 4.000 (6.33), 4.011 (5.09), 4.212 (1.89), 4.229 (4.40), 4.247 (3.20), 4.290 (3.49), 4.297 (3.31), 4.303 (3.60), 5.299 (1.82), 5.310 (4.00), 5.325 (3.85), 5.336 (1.78), 6.793 (7.02), 6.810 (7.60), 6.933 (3.49), 6.948 (7.16), 6.963 (4.07), 7.168 (3.75), 7.184 (6.29), 7.199 (3.09), 7.414 (6.47), 7.429 (6.04), 7.577 (4.11), 7.593 (7.05), 7.609 (4.36), 8.185 (7.96), 8.200 (7.64), 8.465 (6.55), 8.482 (6.18), 8.856 (16.00), 9.192 (5.85), 9.208 (5.71).

Intermediate 7A

Ethyl 8-bromo-7-fluoro-4-hydroxyquinoline-3-carboxylate

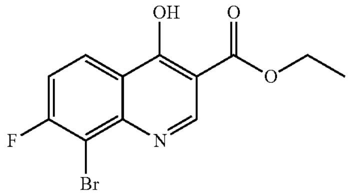 [SMILES: CCOC(=O)c1cnc2c(Br)c(F)ccc2c1O]

A mixture of 2-bromo-3-fluoroaniline (24.89 g, 131 mmol) and diethyl ethoxymethylenemalonate (28.33 g, 131 mmol, 26 mL) was stirred at room temperature for 16 h. Stirring was continued at 250° C. under vacuo (60 mbar) for 6 h. The reaction mixture was allowed to cool to room temperature. The solid residue was stirred in refluxing ethyl acetate (400 mL). The precipitate was filtered off and washed with ethyl acetate. The solid was stirred in a refluxing mixture of ethanol (400 mL) and methanol (40 mL). The hot suspension was filtered off. The solid was washed with ethanol and dried on air.

Yield: 28.60 g (83 mmol, 63% of th.)

LC-MS (Method 1): $R_t$=1.73 min, m/z=314/316 $(M+H)^+$ $^1$H-NMR (400 MHz, DMSO-d6) δ 11.78 (s, 1H), 8.45 (s, 1H), 8.22 (m, 1H), 7.50-7.39 (m, 1H), 4.23 (d, J=7.1 Hz, 2H), 1.28 (t, J=7.1 Hz, 3H).

Intermediate 8A

Ethyl 8-bromo-4-chloro-7-fluoroquinoline-3-carboxylate

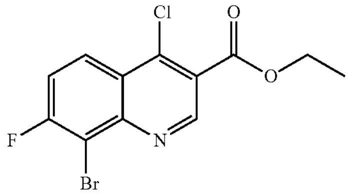

To stirring phosphorus oxychloride (38.4 g, 250 mmol, 23 mL) was added ethyl 8-bromo-7-fluoro-4-hydroxyquinoline-3-carboxylate (step 1) (23.6 g, 75 mmol). The resulting suspension was stirred at 80° C. for 1 h. The mixture was allowed to cool to room temperature and was poured out into vigorously stirred ice-water (100 mL). The resulting mixture was left standing for two days at room temperature. The precipitate was collected by filtration and was washed with water until the filtrate was neutral. Solids were triturated in a mixture of diethyl ether and diisopropyl ether (1:1; 1 L). Solids were filtered off. The filtrate was concentrated in vacuo at 25° C. After co-evaporation of the residue with toluene 21.3 g (64 mmol, 85% of theory) of the title compound were obtained.

Yield: 21.3 g (64 mmol, 85% of th.)

LC-MS (Method 1): $R_t$=2.18 min, m/z=332/334 $(M+H)^+$

Intermediate 9A

Ethyl 4,8-dibromo-7-fluoroquinoline-3-carboxylate

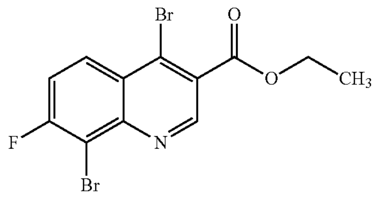 [SMILES: CCOC(=O)c1cnc2c(Br)c(F)ccc2c1Br]

To a stirred solution of ethyl 8-bromo-7-fluoro-4-hydroxyquinoline-3-carboxylate (Example 3, step 2) (60.0 g, 181.2 mmol) in dry dichloromethane (1500 ml) was added at 0° C. DMF (6.0 ml, catalytic amount) followed by phosphoryl bromide (77.9 g, 271.8 mmol) portion wise and stirring continued at 0° C. to ambient temperature for 5 h. The reaction mass was poured onto ice cold water and neutralized with solid sodium bicarbonate to pH 7. The mixture was stirred for 30 min and the organic phase separated. The aqueous phase was extracted with DCM. The combined organic phase was concentrated under reduced pressure. The crude was purified by silica gel column chromatography (eluent: petrolether/ethylacetate, 10:1) to yield 53.32 g (77% of theory) of the product.

LC-MS (Method 2): $R_t$=1.19 min; MS (ESIpos): m/z=376 $[M+H]^+$ $^1$H-NMR (400 MHz, DMSO-d6) δ [ppm]: 1.375 (7.47), 1.393 (16.00), 1.411 (7.67), 2.524 (0.74), 4.426 (2.42), 4.444 (7.47), 4.461 (7.34), 4.479 (2.33), 7.897 (1.80), 7.920 (2.69), 7.941 (2.06), 8.443 (1.83), 8.457 (1.91), 8.466 (1.82), 8.481 (1.75), 9.179 (4.99).

Intermediate 10A

Ethyl 8-bromo-4-ethyl-7-fluoroquinoline-3-carboxylate

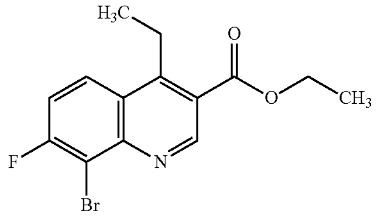 [SMILES: CCOC(=O)c1cnc2c(Br)c(F)ccc2c1CC]

Under argon to a solution of ethyl 4,8-dibromo-7-fluoroquinoline-3-carboxylate (step 1, 30.0 g, 79.6 mmol) in degassed dioxan (300 ml) was added ethylboronic acid (10.6 g, 143 mmol), 1,1'-bis(diphenylphosphino)ferrocene-palladium(II)dichloride dichloromethane complex (4.22 g, 5.17 mmol) and cesium fluoride (26.0 g, 171 mmol) and the mixture stirred at 70° C. bath temperature over night. Water and ethylacetate were added to dissolve the reaction mixture and the organic solvents were evaporated under diminished pressure. The aqueous phase was extracted with DCM several times, the combined organic phases were dried and evaporated. The residue (28 g) was purified in several portions by flash chromatography on silica with cyclohexane/ethylacetate (4-18%) yielding a pure (17.56 g) and a mixed fraction (4.79 g). The mixed fraction was chromatographed under the same conditions to yield pure material (1.44 g) and a mixed fraction 1.99 g). The latter was purified by preparative HPLC (RP 18, gradient with 0.1% aqueous formic acid and acetonitrile) to yield more pure material (1.33 g).

Total yield. 20.33 g (78% of theory)

LC-MS (Method 4): $R_t$=3.55 min; MS (ESIpos): m/z=326 $[M+H]^+$ $^1$H-NMR (600 MHz, DMSO-d6) δ [ppm]: 1.275 (4.81), 1.288 (10.56), 1.300 (4.53), 1.376 (7.45), 1.388 (16.00), 1.395 (0.68), 1.400 (7.58), 3.389 (1.35), 3.402 (4.01), 3.414 (3.89), 3.427 (1.17), 4.405 (2.31), 4.417 (7.12), 4.428 (7.00), 4.440 (2.15), 7.776 (1.85), 7.790 (2.36), 7.791 (2.28), 7.805 (1.87), 8.451 (1.74), 8.461 (1.80), 8.467 (1.72), 8.476 (1.60), 9.219 (7.16).

Intermediate 11A

8-Bromo-4-ethyl-7-fluoroquinoline-3-carboxylic acid

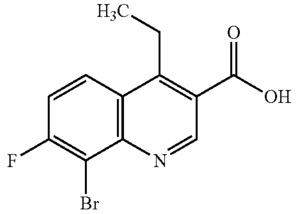 [SMILES: CCc1c(C(=O)O)cnc2c(Br)c(F)ccc12]

A mixture of ethyl 8-bromo-4-ethyl-7-fluoroquinoline-3-carboxylate (19.0 g, 58.3 mmol) in Ethanol (80 ml) and THF (80 ml) was treated dropwise with aqueous sodium hydroxide (35 ml, 5.0 M, 175 mmol) and stirred 30 min at 80° C. The reaction mixture was slowly added at 40° under stirring to water (200 ml) and formic acid (13.2 ml). To complete precipitation the organic solvents were largely evaporated and hydrochloric acid (15 ml, 5.0 M) added (pH 2). The precipitate was filtered off washed with several portions of water and dried in vacuo.

Yield: 17.27 g (95% purity, 95% of theory)

LC-MS (Method 2): $R_t$=0.87 min; MS (ESIpos): m/z=298 $[M+H]^+$ $^1$H-NMR (600 MHz, DMSO-d6) δ [ppm]: 1.267 (7.94), 1.279 (16.00), 1.291 (7.47), 1.447 (0.45), 3.447 (2.52), 3.459 (6.78), 3.472 (6.52), 3.484 (2.11), 7.759 (2.54), 7.774 (4.56), 7.788 (2.55), 8.439 (2.58), 8.449 (2.82), 8.454 (2.85), 8.464 (2.37), 9.244 (10.71), 13.665 (1.91).

Intermediate 12A

8-Bromo-N-[(4S)-3,4-dihydro-2H-chromen-4-yl]-4-ethyl-7-fluoroquinoline-3-carboxamide

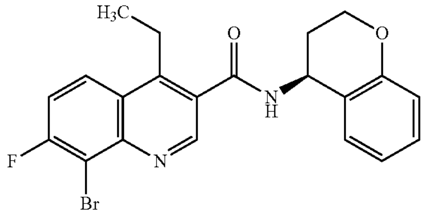 [SMILES: CCc1c(C(=O)N[C@H]2CCOc3ccccc32)cnc2c(Br)c(F)ccc12]

A suspension of 8-bromo-4-ethyl-7-fluoroquinoline-3-carboxylic acid (17.3 g, 57.9 mmol) in THF (300 ml) was heated to 60° C., and treated with (4S)-chroman-4-amine hydrochloride (14.0 g, 75.3 mmol), N,N-diisopropylethylamine (40 ml, 230 mmol). Under stirring a solution of 2,4,6-tripropyl-1,3,5,2,4,6-trioxatriphosphinane 2,4,6-trioxide in ethylacetate (55 ml, 50% content, 93 mmol) was added dropwise, the heating temporarily removed to keep the temperature between 60 and 65° C. After completed addition the mixture was stirred at 60 C for 1 h. Water (300 ml) was added, the THF largely removed under diminished pressure and the mixture stirred at 60° C. for 45 min. The precipitate was filtered, washed with water and dried in vacuo at 50° C.

Yield: 24.0 g (97% of theory)

LC-MS (Method 4): $R_t$=3.37 min; MS (ESIpos): m/z=429 $[M+H]^+$ $^1$H-NMR (600 MHz, DMSO-d6) δ [ppm]: 1.265 (7.90), 1.278 (16.00), 1.290 (7.22), 2.050 (1.41), 2.055 (1.44), 2.062 (1.53), 2.067 (1.48), 2.073 (1.72), 2.084 (0.99), 2.215 (1.72), 2.223 (1.65), 2.229 (1.65), 2.238 (1.21), 2.386 (0.41), 2.425 (0.80), 2.653 (0.58), 3.223 (2.36), 3.235 (6.25), 3.248 (6.02), 3.260 (2.17), 4.231 (1.22), 4.245 (2.98), 4.250 (2.22), 4.258 (2.47), 4.263 (2.12), 4.271 (2.13), 4.276 (2.43), 4.282 (2.20), 4.288 (2.44), 4.295 (1.01), 4.301 (1.01), 5.297 (1.25), 5.306 (2.53), 5.320 (2.44), 5.330 (1.08), 6.794 (4.46), 6.807 (4.69), 6.928 (2.32), 6.939 (4.56), 6.951 (2.53), 7.166 (2.29), 7.177 (3.74), 7.189 (1.85), 7.357 (4.02), 7.370 (3.65), 7.736 (3.06), 7.751 (4.60), 7.766 (3.06), 8.364 (2.91), 8.374 (3.11), 8.380 (3.01), 8.390 (2.77), 8.939 (12.93), 9.149 (3.67), 9.163 (3.55).

Intermediate 13A

8-Bromo-4-chloro-7-fluoroquinoline-3-carboxylic acid

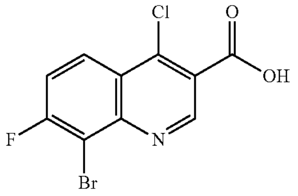 [SMILES: O=C(O)c1cnc2c(Br)c(F)ccc2c1Cl]

A mixture of ethyl 8-bromo-4-chloro-7-fluoroquinoline-3-carboxylate (Expl. 8A) (11.9 g, 35.7 mmol) in THF (82 ml) was treated dropwise with aqueous sodium hydroxide (14 mL 45% sodium hydroxide diluted in 0.8 mL water) at room temperature followed by dilution with 15 mL water. The occurred precipitate was filtered off and was slowly added to water (200 mL, T=40° C.) under stirring. The resulting mixture was treated with formic acid (59 mL) at 60° C. The precipitate was filtered off, washed with several portions of water and dried on air.

Yield: 9.4 g (88% purity, 76% of theory)

LC-MS (Method 5): $R_t$=0.774 min; m/z=305.9 $(M+H)^+$ $^1$H-NMR (400 MHz, DMSO-d6) δ 14.14 (bs), 9.29 (s, 1H), 8.51-8.47 (dd, 1H), 7.93-7.88 (t, 1H).

Intermediate 14A

8-Bromo-4-chloro-N-[(4S)-3,4-dihydro-2H-chromen-4-yl]-7-fluoroquinoline-3-carboxamide

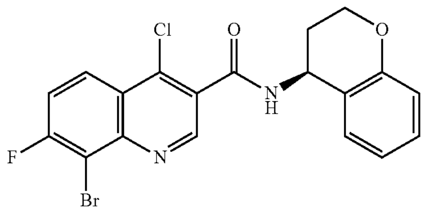 [SMILES: O=C(N[C@H]1CCOc2ccccc21)c1cnc2c(Br)c(F)ccc2c1Cl]

To a suspension of 8-bromo-4-chloro-7-fluoroquinoline-3-carboxylic acid (8.56 g, 24.41 mmol) in dry toluene (180 mL) was added 3 drops of DMF. Then thionyl chloride (4.35 g, 36.62 mmol) was added dropwise within 10 minutes. After stirring for 2 h at 90° C. the mixture was cooled to room temperature and solvents were removed under reduced pressure. The residue was dissolved in dry tetrahydrofuran (200 mL) and after adding (4S)-chroman-4-amine hydrochloride (4.53 g, 24.41 mmol) and N,N-diisopropylethylamine (24.47 g, 189 mmol) stirring was continued for 18 h at room temperature. Solvents were removed under reduced pressure and the residue was partitioned between water (150 mL) and dichloromethane (150 mL). The precipitate was filtered off, washed with several portions of water and dried on air.

Yield: 10.16 g (96% of theory)

LC-MS (Method 5): $R_t$=1.26 min; m/z=435 $(M+H)^+$ log P (HCOOH) (Method 0)=3.18

$^1$H-NMR (400 MHz, DMSO-d6) δ 9.30-9.28 (m, 1H), 9.08 (s, 1H), 8.43-8.39 (m, 1H), 7.92-7.88 (m, 1H), 7.40-7.38 (m, 1H), 7.21-7.16 (m, 1H), 6.96-6.92 (m, 1H), 6.82-6.79 (m, 1H), 5.29 (m, 1H), 4.30-4.21 (m, 2H), 2.25-2.20 (m, 1H), 2.11-2.07 (m, 1H).

Intermediate 15A

8-Bromo-N-[(4S)-3,4-dihydro-2H-chromen-4-yl]-7-fluoro-4-(3-fluoroazetidin-1-yl)quinoline-3-carboxamide

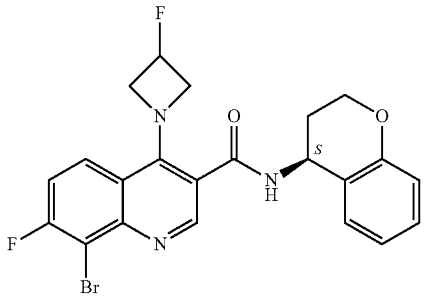

A mixture of 8-bromo-4-chloro-N-[(4S)-3,4-dihydro-2H-chromen-4-yl]-7-fluoroquinoline-3-carboxamide (Expl. 14A) (295 mg, 0.677 mmol), 3-fluoroazetidine hydrochloride (155 mg, 1.39 mmol) and 1,4-diazabicyclo[2.2.2]octane (310 mg, 2.764 mmol) in tetrahydrofuran (10 mL) was stirred at 60° C. for 18 h. The mixture was cooled to room temperature, water was added and the aqueous layer was extracted with dichloromethane (3×10 mL). Solvents were dried and removed under reduced pressure, leaving 297 mg (93% of theory) of the title compound.

LC-MS (Method 5): $R_t$=0.67 min; m/z=475.9 $(M+H)^+$ log P (HCOOH) (Method 0)=1.29

$^1$H-NMR (400 MHz, DMSO-d6) δ 9.10-9.08 (m, 1H), 8.56 (s, 1H), 8.12-8.08 (m, 1H), 7.44-7.39 (m, 1H), 7.34-7.32 (m, 1H), 7.21-7.16 (m, 1H), 6.95-6.91 (m, 1H), 6.82-6.80 (m, 1H), 5.56-5.38 (m, 1H), 5.22-5.20 (m, 1H), 4.73-4.53 (m, 4H), 4.28-4.26 (m, 2H), 2.19-2.16 (m, 1H), 2.09-2.00 (m, 1H).

Intermediate 16A

Ethyl 8-bromo-7-fluoro-4-[4-(methoxycarbonyl) tetrahydro-2H-pyran-4-yl]quinoline-3-carboxylate

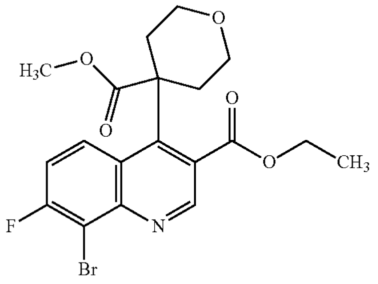 [SMILES: CCOC(=O)c1cnc2c(Br)c(F)ccc2c1C1(C(=O)OC)CCOCC1]

The title compound was prepared from ethyl 8-bromo-4-chloro-7-fluoroquinoline-3-carboxylate (Example 8A) according to the procedure given for example 4A.

Yield: 82% of theory

LC-MS (Method 4): Rt=3.28 min; MS (ESIpos): m/z=440 [M+H]+

$^1$H-NMR (600 MHz, DMSO-d6) δ [ppm]: 1.362 (4.09), 1.374 (8.34), 1.385 (4.08), 2.197 (0.71), 2.207 (0.89), 2.219 (1.15), 2.224 (1.09), 2.229 (1.08), 2.236 (0.93), 2.247 (0.82), 2.411 (2.32), 2.433 (1.85), 3.566 (16.00), 3.795 (0.53), 3.812 (2.47), 3.824 (2.83), 3.831 (4.67), 3.982 (0.61), 4.439 (1.34), 4.450 (3.95), 4.462 (3.85), 4.474 (1.23), 7.787 (1.17), 7.800 (1.50), 7.816 (1.22), 8.248 (1.21), 8.258 (1.28), 8.265 (1.21), 8.274 (1.11), 8.956 (4.93).

Intermediate 17A

8-Bromo-7-methoxy-4-(tetrahydro-2H-pyran-4-yl) quinoline-3-carboxylic acid

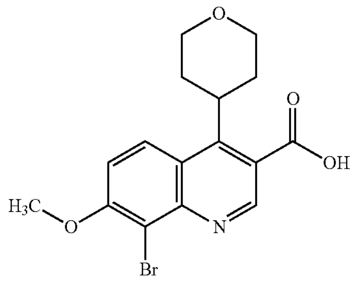 [SMILES: COc1ccc2c(C3CCOCC3)c(C(=O)O)cnc2c1Br]

Ethyl 8-bromo-7-fluoro-4-[4-(methoxycarbonyl)tetrahydro-2H-pyran-4-yl]quinoline-3-carboxylate (Intermediate 16A) (3.00 g, 6.81 mmol), methanol (15 ml) and aqueous sodium hydroxide (8.2 ml, 5 M, 41 mmol) were stirred over night at 75° bath temperature. More aqueous sodium hydroxide (2.7 ml, 5 M, 13.5 mmol) was added and the mixture refluxed over night. Water (30 ml) was added and the warm solution was acidified with conc. hydrochloric acid to pH 2. The precipitate was filtered off, washed with water and dried in vacuo.

Yield: 2.3 g (96% purity, 88% of theory

LC-MS (Method 4): Rt=1.63 min; MS (ESIpos): m/z=366 [M+H]+

$^1$H-NMR (600 MHz, DMSO-d6) 5 [ppm]: 1.664 (2.08), 1.685 (2.17), 2.373 (0.64), 2.387 (1.49), 2.393 (1.56), 2.407 (1.48), 2.414 (1.41), 2.429 (0.74), 3.169 (0.43), 3.521 (1.42), 3.539 (2.67), 3.558 (1.51), 3.951 (0.63), 3.972 (1.14), 4.006 (2.13), 4.012 (2.27), 4.024 (2.09), 4.031 (1.96), 4.068 (16.00), 7.671 (2.40), 7.687 (2.47), 8.544 (2.28), 8.559 (2.17), 8.947 (3.71), 13.709 (0.47).

Intermediate 18A

8-Bromo-N-[(4S)-3,4-dihydro-2H-chromen-4-yl]-7-methoxy-4-(tetrahydro-2H-pyran-4-yl)quinoline-3-carboxamide

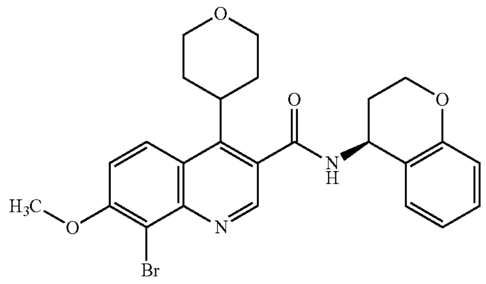 [SMILES: COc1ccc2c(C3CCOCC3)c(C(=O)N[C@H]3CCOc4ccccc43)cnc2c1Br]

To a suspension of 8-bromo-7-methoxy-4-(tetrahydro-2H-pyran-4-yl)quinoline-3-carboxylic acid (intermediate 17A) (300 mg, 0.82 mmol) in THF (5 ml) was added N,N-diisopropylethylamine (0.71 ml, 4.1 mmol) and HATU (289 mg, 1.02 mmol) and the solution stirred 30 min at rt. Then (4S)-chroman-4-amine hydrochloride (380 mg, 2.05 mmol) were added and stirring continued over night. Most of the THF was evaporated under diminished pressure, the residue added to a (2:1) mixture of water/ethanol (50 ml) and acidified with acetic acid to pH 4.5. The mixture was stirred at 50° for 30 min, cooled, the precipitate filtered off, washed with water/ethanol (2:1) and dried in vacuo.

Yield: 311 mg (76% of theory)

LC-MS (Method 4): Rt=2.72 min; MS (ESIneg): m/z=495 [M−H]−

$^1$H-NMR (400 MHz, DMSO-d6) δ [ppm]: 1.638 (1.03), 1.675 (1.81), 1.711 (1.11), 2.054 (0.67), 2.081 (0.92), 2.219 (0.83), 2.232 (0.86), 2.240 (0.81), 2.378 (1.49), 2.409 (1.45), 3.436 (0.70), 3.464 (1.27), 3.492 (1.41), 3.519 (1.39), 3.547 (0.74), 3.692 (0.83), 3.992 (2.02), 4.005 (1.93), 4.019 (2.23), 4.050 (16.00), 4.216 (0.51), 4.236 (1.33), 4.257 (1.17), 4.282 (1.27), 4.297 (1.23), 5.300 (1.27), 5.320 (1.31), 6.787 (2.26), 6.807 (2.54), 6.925 (1.10), 6.943 (2.32), 6.962 (1.36), 7.161 (1.24), 7.180 (1.98), 7.199 (0.96), 7.403 (2.05), 7.421

(1.92), 7.636 (2.48), 7.660 (2.61), 8.463 (2.36), 8.487 (2.24), 8.781 (5.86), 9.114 (1.89), 9.135 (1.90).

EXAMPLES

Example 1

N-[(4S)-3,4-Dihydro-2H-chromen-4-yl]-4-(3,6-dihydro-2H-pyran-4-yl)-8-(2,3,5-trifluorophenyl)quinoline-3-carboxamide

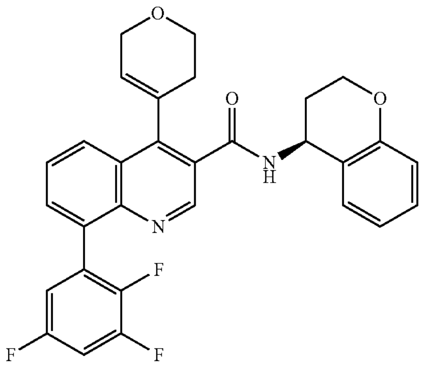 [SMILES: O=C(N[C@H]1CCOc2ccccc21)c1cnc2c(-c3cc(F)cc(F)c3F)cccc2c1C1=CCOCC1]

Under argon a thick-walled vessel was charged with 4-chloro-N-[(4S)-3,4-dihydro-2H-chromene-4-yl]-8-(2,3,5-trifluorophenyl)quinoline-3-carboxamide (Expl. 3A) (500 mg, 1.07 mmol), 4-(4,4,5,5-Tetramethyl-1,3,2-dioxaborolan-2-yl)-3,6-dihydro-2H-pyran (246 mg, 1.17 mmol), potassium carbonate (295 mg, 2.13 mmol), 1,1'-bis(diphenylphosphino)ferrocene-palladium(II)dichloride dichloromethane complex (43.5 mg, 53 μmol) and a degassed 5:1 mixture of dioxane/water (4 ml). The vessel was capped and heated under stirring at 80° C. over night. The mixture was filtered over celite and washed with ethylacetate. The filtrate was diluted with water and extracted with ethylacetate. The combined organic phases were dried and evaporated. The residue (650 mg) was purified by flash chromatography on silica (50 g) with cyclohexane/ethylacetate (8-40%).

Yield: 500 mg (91% of theory)

LC-MS (Method 2): $R_t$=1.14 min; MS (ESIpos): m/z=517 [M+H]+

$^1$H-NMR (400 MHz, DMSO-d6) δ [ppm]: −0.149 (0.50), 0.146 (0.54), 1.992 (1.11), 2.001 (1.30), 2.008 (1.31), 2.019 (1.65), 2.026 (1.38), 2.162 (1.42), 2.174 (1.44), 2.182 (1.34), 2.327 (0.54), 2.366 (0.64), 2.430 (2.29), 2.669 (0.53), 2.709 (0.50), 3.901 (1.68), 4.219 (2.74), 4.245 (4.37), 4.253 (4.09), 4.261 (3.62), 4.270 (3.71), 4.289 (1.96), 5.225 (0.89), 5.239 (2.03), 5.256 (2.03), 5.861 (2.53), 6.768 (4.46), 6.788 (4.87), 6.891 (2.01), 6.908 (4.36), 6.926 (2.57), 7.139 (2.23), 7.142 (2.32), 7.160 (3.78), 7.178 (1.85), 7.181 (1.79), 7.242 (1.88), 7.254 (1.90), 7.264 (1.94), 7.342 (3.24), 7.360 (3.01), 7.588 (0.68), 7.596 (0.82), 7.611 (1.51), 7.624 (1.54), 7.637 (1.54), 7.644 (0.96), 7.652 (0.83), 7.660 (0.76), 7.772 (2.74), 7.790 (4.75), 7.811 (4.54), 7.862 (5.09), 7.865 (5.41), 7.880 (3.55), 7.883 (3.29), 8.093 (4.73), 8.096 (4.68), 8.114 (4.19), 8.117 (3.89), 8.892 (16.00), 8.938 (3.57), 8.959 (3.47).

Example 2

N-[(4S)-3,4-Dihydro-2H-chromen-4-yl]-4-(tetrahydro-2H-pyran-4-yl)-8-(2,3,5-trifluorophenyl)quinoline-3-carboxamide

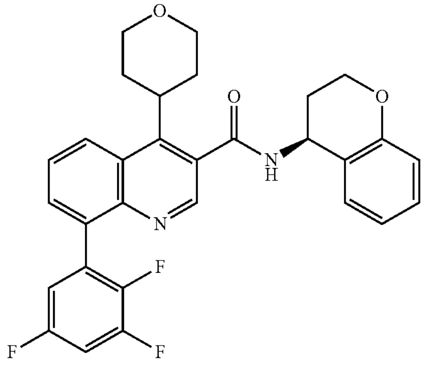 [SMILES: O=C(N[C@H]1CCOc2ccccc21)c1cnc2c(-c3cc(F)cc(F)c3F)cccc2c1C1CCOCC1]

Procedure 1

Under argon N-[(4S)-3,4-dihydro-2H-chromen-4-yl]-4-(3,6-dihydro-2H-pyran-4-yl)-8-(2,3,5-trifluorophenyl)quinoline-3-carboxamide (Expl. 1) (500 mg, 0.97 mmol) was dissolved in ethyl acetate/ethanol (2:1, 15 ml). The catalyst, 10% palladium on charcoal (125 mg), was added, argon replaced by hydrogen and the mixture stirred under atmospheric pressure of hydrogen for 18 h. The reaction mixture was filtered over celite, rinsed with ethyl acetate and concentrated in vacuo. The residue (560 mg, a crude mixture of different reduction products) was dissolved in DMSO (4.5 ml) and treated with ammonium cerium-nitrate (2 M solution in water, 1.9 ml, 3.8 mmol) resulting in a brownish suspension, with was stirred over night at ambient temperature. The mixture was dissolved by addition of more DMSO, acetonitrile and some 5 M formic acid and directly purified via prep. HPLC (C18, gradient: 0.1% aq. formic acid/acetonitrile). Yield: 175 mg (31% of th.) A mixed fraction (75 mg) was repurified by flash chromatography on silica with cyclohexane/ethylacetate (5-50%) yielding a second crop of 37 mg (7% of theory).

LC-MS (Method 4): $R_t$=3.80 min; MS (ESIpos): m/z=519 $[M+H]^+$ $^1$H-NMR (400 MHz, DMSO-d6) δ [ppm]: −0.008 (2.70), 0.008 (2.80), 1.687 (1.87), 1.724 (3.01), 1.763 (2.03), 2.030 (0.72), 2.038 (1.16), 2.045 (1.24), 2.057 (1.32), 2.073 (1.91), 2.080 (1.57), 2.088 (1.14), 2.192 (0.71), 2.201 (1.15), 2.214 (1.69), 2.226 (1.65), 2.235 (1.62), 2.248 (1.14), 2.256 (0.82), 2.269 (0.56), 2.395 (0.93), 2.425 (2.48), 2.454 (2.48), 2.523 (1.11), 3.457 (1.19), 3.486 (2.26), 3.515 (2.39), 3.545 (2.55), 3.572 (1.42), 3.730 (1.41), 4.000 (2.13), 4.010 (3.59), 4.024 (3.66), 4.038 (3.27), 4.204 (0.82), 4.211 (1.03), 4.232 (2.75), 4.239 (2.11), 4.252 (2.47), 4.262 (2.60), 4.273 (2.58), 4.280 (2.20), 4.289 (2.31), 4.301 (0.90), 4.308 (1.00), 4.317 (0.71), 5.286 (1.08), 5.301 (2.49), 5.320 (2.53), 5.335 (1.12), 6.778 (4.25), 6.781 (4.67), 6.799 (4.92), 6.801 (5.15), 6.910 (2.31), 6.913 (2.42), 6.929 (4.82), 6.931 (4.87), 6.947 (2.96), 6.950 (2.90), 7.150 (2.40), 7.154 (2.57), 7.171 (3.98), 7.189 (2.06), 7.193 (2.33), 7.204 (1.61), 7.208 (2.00), 7.220 (1.97), 7.230 (2.00), 7.242 (1.03), 7.398 (4.14), 7.416 (3.86), 7.571 (0.69), 7.578 (0.85), 7.586 (0.98), 7.593 (1.57), 7.598 (1.47), 7.606 (1.60), 7.614 (1.53), 7.620 (1.61), 7.627 (1.01), 7.634 (0.92), 7.642 (0.84), 7.774 (2.56), 7.792 (4.98), 7.813 (5.12), 7.832 (5.89), 7.835 (6.55), 7.850 (3.13), 7.853 (2.79), 8.561 (3.72), 8.564 (3.88), 8.582 (3.67), 8.585 (3.55), 8.738 (16.00), 9.160 (4.40), 9.180 (4.33).

Procedure 2

Under argon a flask was charged with 8-bromo-N-[(4S)-3,4-dihydro-2H-chromen-4-yl]-4-(tetrahydro-2H-pyran-4-yl)quinoline-3-carboxamide (Expl. 6A) (850 mg, 1.82 mmol), 2,3,5-trifluorobenzene boronic acid (160 mg, 0.91 mmol), potassium carbonate (503 mg, 3.64 mmol), 1,1'-bis(diphenylphosphino)ferrocene-palladium(II)dichloride dichloromethane complex (44.6 mg, 54.6 μmol) and (2'-aminobiphenyl-2-yl)(chloro)palladium-dicyclohexyl(2',4',6'-triisopropylbiphenyl-2-yl)phosphine (1:1) (42.9 mg, 54.6 μmol) and a degassed 5:1 mixture of dioxane/water (5.1 ml). The mixture was stirred in a preheated bath of 70° C. for 45 min. Then another portion of 2,3,5-trifluorobenzene boronic acid (160 mg, 0.91 mmol) was added and stirred at the same temperature for 45 min. The latter process was repeated once more. After consumption of the starting material, water and ethylacetate were added at RT stirred and the phases separated. The aqueous phase was extracted several times with etylacetate, the combined organic phases dried and evaporated under diminished pressure. The residue (1.15 g) war purified by flash chromatography on silica (100 g) with cyclohexane/ethylacetate (32-40%).

Yield: 833 mg (88% of theory)

LC-MS (Method 2): $R_t$=1.13 min; MS (ESIpos): m/z=519 $[M+H]^+$ $^1$H-NMR (500 MHz, DMSO-d6) δ [ppm]: 1.691 (1.98), 1.716 (2.17), 1.736 (1.98), 1.761 (2.04), 2.038 (0.81), 2.045 (1.25), 2.050 (1.33), 2.060 (1.42), 2.073 (1.82), 2.078 (1.55), 2.085 (1.09), 2.200 (0.78), 2.207 (1.17), 2.217 (1.73), 2.227 (1.71), 2.234 (1.72), 2.245 (1.25), 2.252 (0.84), 2.262 (0.56), 2.405 (1.02), 2.429 (2.67), 2.453 (2.70), 3.464 (1.17), 3.485 (2.16), 3.508 (1.29), 3.523 (1.50), 3.544 (2.52), 3.567 (1.39), 3.730 (1.32), 4.003 (2.20), 4.013 (3.04), 4.025 (4.09), 4.036 (2.77), 4.046 (1.82), 4.212 (0.98), 4.218 (1.16), 4.234 (3.00), 4.240 (2.08), 4.251 (2.37), 4.257 (1.90), 4.268 (1.90), 4.275 (2.44), 4.281 (2.12), 4.288 (2.38), 4.298 (1.00), 4.304 (1.09), 4.310 (0.80), 5.292 (1.22), 5.304 (2.66), 5.320 (2.56), 5.331 (1.16), 5.752 (1.91), 6.783 (5.04), 6.798 (5.49), 6.915 (2.50), 6.930 (5.20), 6.945 (2.93), 7.154 (2.55), 7.157 (2.49), 7.171 (4.18), 7.185 (2.13), 7.188 (1.98), 7.208 (2.12), 7.217 (2.09), 7.225 (2.06), 7.399 (4.31), 7.415 (4.06), 7.574 (0.76), 7.580 (0.94), 7.586 (1.07), 7.592 (1.68), 7.602 (1.71), 7.609 (1.64), 7.613 (1.64), 7.619 (0.99), 7.624 (0.89), 7.631 (0.78), 7.778 (2.81), 7.793 (5.08), 7.810 (4.86), 7.833 (6.27), 7.835 (6.27), 7.847 (3.60), 8.563 (4.14), 8.580 (3.96), 8.738 (16.00), 9.159 (4.57), 9.176 (4.42).

Example 3

N-[(4S)-3,4-Dihydro-2H-chromen-4-yl]-7-fluoro-4-(tetrahydro-2H-pyran-4-yl)-8-(2,3,5-trifluorophenyl)quinoline-3-carboxamide

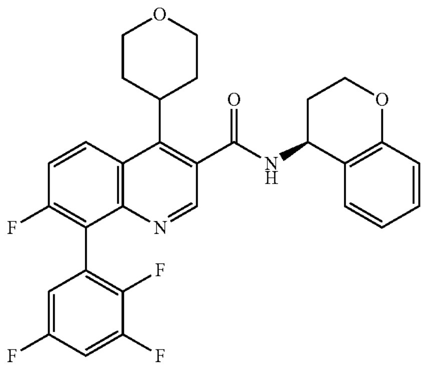 [SMILES: O=C(N[C@H]1CCOc2ccccc21)c1cnc2c(-c3cc(F)cc(F)c3F)c(F)ccc2c1C1CCOCC1]

The title compound was prepared from ethyl 8-bromo-4-chloro-7-fluoroquinoline-3-carboxylate (Expl. 8A) in a similar manner as in the methods described for example 4A, 5A, 6A and example 2, procedure LC-MS (Method 2): $R_t$=1.14 min; MS (ESIpos): m/z=537 [M+H]+

$^1$H-NMR (400 MHz, DMSO-d6) δ [ppm]: 1.679 (4.00), 1.713 (6.39), 1.737 (3.34), 2.033 (2.47), 2.052 (2.85), 2.067 (3.55), 2.211 (2.97), 2.220 (3.09), 2.229 (2.93), 2.243 (2.14), 2.328 (0.95), 2.367 (2.64), 2.388 (4.62), 2.401 (5.48), 2.420 (5.36), 2.432 (5.24), 2.449 (2.76), 2.464 (2.06), 2.670 (0.95), 2.710 (0.91), 3.444 (1.32), 3.471 (3.63), 3.499 (4.04), 3.523 (3.09), 3.543 (4.29), 3.574 (2.23), 3.737 (3.01), 4.016 (7.26), 4.036 (6.06), 4.197 (2.06), 4.219 (4.21), 4.225 (4.91), 4.246 (4.41), 4.270 (4.74), 4.286 (4.16), 5.275 (2.27), 5.288 (5.07), 5.307 (5.11), 5.322 (2.19), 6.778 (9.73), 6.799 (10.85), 6.904 (4.87), 6.923 (10.35), 6.942 (6.10), 7.152 (5.03), 7.170 (8.37), 7.188 (4.00), 7.278 (3.96), 7.286 (4.00), 7.389 (8.87), 7.407 (8.29), 7.642 (1.57), 7.650 (1.90), 7.665 (3.42), 7.678 (3.34), 7.686 (3.34), 7.692 (3.38), 7.698 (2.10), 7.706 (1.86), 7.714 (1.73), 7.761 (5.44), 7.784 (10.27), 7.807 (5.61), 8.664 (5.11), 8.679 (5.65), 8.688 (5.53), 8.703 (4.95), 8.758 (15.75), 8.770 (16.00), 9.155 (6.72), 9.173 (6.47).

Example 4

N-[(4S)-3,4-Dihydro-2H-chromen-4-yl]-4-ethyl-7-fluoro-8-(2,3,5-trifluorophenyl)quinoline-3-carboxamide

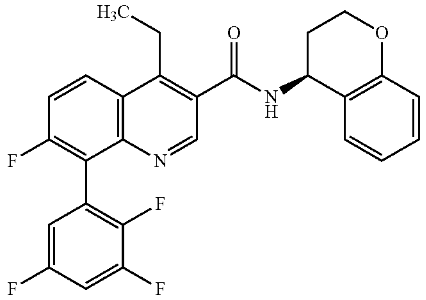 [SMILES: CCc1c(C(=O)N[C@H]2CCOc3ccccc32)cnc2c(-c3cc(F)cc(F)c3F)c(F)ccc12]

Under argon a flask was charged with 8-bromo-N-[(4S)-3,4-dihydro-2H-chromen-4-yl]-4-ethyl-7-fluoroquinoline-3-carboxamide (Expl. 12A) (13.0 g, 30.3 mmol), 2,3,5-trifluorobenzene boronic acid (2.67 g, 15.2 mmol), potassium carbonate (8.37 g, 60.6 mmol) and (2'-aminobiphenyl-2-yl)(chloro)palladium-dicyclohexyl(2',4',6'-triisopropylbiphenyl-2-yl)phosphine (1:1) (477 mg, 606 μmol). A degassed 5:1 mixture of dioxan/water (140 ml) was added and the mixture stirred at 70° C. for 45 min. Two more portions of 2,3,5-trifluorobenzene boronic acid (2.67 g, 15.2 mmol) were added within 1.5 h and stirring continued for 1.5 h after the last dosage. Then more 2,3,5-trifluorobenzene boronic acid (5.33 g, 30.3 mmol) and (2'-aminobiphenyl-2-yl)(chloro)palladium-dicyclohexyl(2',4',6'-triisopropylbiphenyl-2-yl)phosphine (1:1) (238 mg, 303 μmol) were added and stirred at the same temperature for 1 h. Water and ethylacetate were added at RT stirred and the phases separated. The aqueous phase was extracted two times with ethylacetate, the combined organic phases dried and evaporated under diminished pressure. The residue (24 g) was purified by flash chromatography on silica with DCM and methanol (0-2%) and then in a second silica chromatography with cyclohexane-ethylacetate (10-25%) yielding 7.63 g. Remaining mixed fractions were purified by preparative HPLC (RP 18, gradient with 0.1% aqueous formic acid and acetonitrile) to yield more pure material (0.75 g).

Total yield: 8.38 g (58% of theory)

LC-MS (Method 4): $R_t$=3.99 min; MS (ESIpos): m/z=481 $[M+H]^+$ $^1$H-NMR (600 MHz, DMSO-d6) δ [ppm]: 0.005 (0.62), 1.305 (8.10), 1.317 (16.00), 1.318 (15.96), 1.329 (7.70), 1.397 (8.26), 2.020 (0.99), 2.026 (1.42), 2.031 (1.82), 2.037 (1.85), 2.042 (1.90), 2.049 (1.91), 2.054 (2.16), 2.060 (1.62), 2.065 (1.16), 2.181 (0.98), 2.187 (1.48), 2.195 (2.06), 2.203 (1.94), 2.209 (2.04), 2.218 (1.46), 2.223 (1.05), 2.232 (0.71), 2.516 (0.89), 2.520 (0.95), 2.523 (0.96), 3.227 (0.71), 3.236 (1.35), 3.249 (3.27), 3.257 (3.63), 3.261 (4.26), 3.270 (4.39), 3.282 (3.24), 3.294 (1.47), 3.304 (1.17), 4.214 (0.72), 4.219 (1.14), 4.226 (1.21), 4.233 (2.56), 4.239 (3.13), 4.245 (2.80), 4.252 (3.53), 4.255 (3.49), 4.261 (3.70), 4.266 (2.73), 4.272 (3.23), 4.280 (1.06), 4.285 (1.15), 4.291 (0.88), 5.280 (1.26), 5.291 (2.88), 5.301 (2.73), 5.312 (1.11), 6.781 (6.23), 6.783 (6.34), 6.795 (6.65), 6.796 (6.62), 6.907 (3.27), 6.919 (6.32), 6.932 (3.61), 7.153 (2.85), 7.164 (4.85), 7.176 (2.33), 7.295 (2.49), 7.302 (2.41), 7.334 (2.71), 7.345 (4.69), 7.356 (2.50), 7.660 (0.92), 7.665 (1.13), 7.670 (1.32), 7.675 (2.00), 7.678 (1.91), 7.683 (2.01), 7.689 (1.92), 7.692 (1.90), 7.697 (1.20), 7.702 (1.05), 7.707 (0.93), 7.780 (3.82), 7.795 (7.06), 7.811 (3.81), 8.484 (4.02), 8.494 (4.24), 8.500 (4.25), 8.510 (3.87), 8.812 (11.05), 8.818 (10.77), 9.124 (4.07), 9.137 (3.96).

Example 5

N-[(4S)-3,4-Dihydro-2H-chromen-4-yl]-7-fluoro-4-(3-fluoroazetidin-1-yl)-8-(2,3,5-trifluorophenyl)quinoline-3-carboxamide

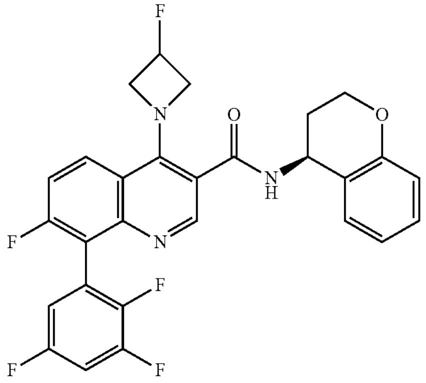 [SMILES: O=C(N[C@H]1CCOc2ccccc21)c1cnc2c(-c3cc(F)cc(F)c3F)c(F)ccc2c1N1CC(F)C1]

A mixture of 8-bromo-N-[(4S)-3,4-dihydro-2H-chromen-4-yl]-7-fluoro-4-(3-fluoroazetidin-1-yl)quinoline-3-carboxamide (Expl. 15A) (1500 mg, 3.163 mmol) and bis(triphenylphosphine)dichloropalladium(II) (255 mg, 0.363 mmol) in 1,4-dioxane (50 mL) was stirred at room temperature for 2 h. After the addition of (2,3,5-trifluorophenyl)boronic acid (2200 mg, 12.51 mmol), sodium carbonate (5000 mg, 47.175 mmol) and water (6.20 mL) stirring was continued for 18 h at 90° C. The mixture was cooled to room temperature, water was added and the aqueous layer was extracted with dichloromethane (3×100 mL). Solvents were dried and removed under reduced pressure. Purification by preparative HPLC (water/acetonitrile 80:20→5:95/afforded 675 mg (40.6% of theory) of the title compound.

LC-MS (Method 5): $R_t$=0.88 min; m/z=526 $(M+H)^+$ log P (HCOOH) (Method 0)=1.93

$^1$H-NMR (400 MHz, DMSO-d6) δ 1.99-2.08 (m, 1H), 2.14-2.19 (m, 1H), 4.25 (t. J=3.5 Hz, 2H), 4.57-4.74 (m, 4H), 5.17-5.22 (m, 1H), 5.42-5.60 (m, 1H), 6.78-6.80 (m, 1H), 6.88-6.92 (m, 1H), 7.14-7.23 (m, 2H), 7.30-7.32 (m, 1H), 7.44-7.49 (m, 1H), 7.55-7.65 (m, 1H), 8.20-8.24 (m, 1H), 8.43 (s, 1H), 9.03-9.06 (m, 1H).

Example 6

N-[(4S)-3,4-dihydro-2H-chromen-4-yl]-4-(3,6-dihydro-2H-pyran-4-yl)-7-fluoro-8-(2,3,5-trifluorophenyl)quinoline-3-carboxamide

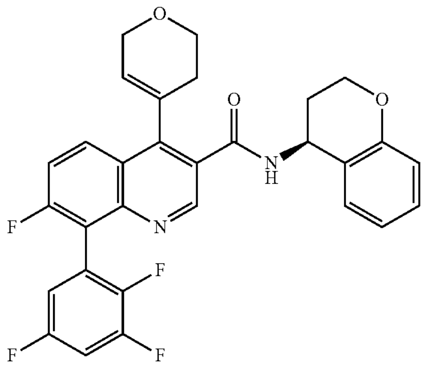 [SMILES: O=C(N[C@H]1CCOc2ccccc21)c1cnc2c(-c3cc(F)cc(F)c3F)c(F)ccc2c1C1=CCOCC1]

The title compound has been synthesized in analogy to Example 1.

LC-MS (Method 2): $R_t$=1.15 min; MS (ESIpos): m/z=535 $[M+H]^+$ $^1$H-NMR (400 MHz, DMSO-d6) δ [ppm]: 1.235 (0.66), 1.981 (2.08), 1.989 (2.69), 1.998 (2.43), 2.007 (2.94), 2.016 (2.83), 2.024 (2.32), 2.158 (2.87), 2.170 (2.86), 2.179 (2.72), 2.192 (1.96), 2.328 (0.57), 2.366 (1.31), 2.415 (3.83), 2.710 (0.44), 3.900 (3.04), 4.186 (2.08), 4.214 (5.03), 4.242 (7.22), 4.250 (7.35), 4.259 (6.65), 4.267 (6.99), 4.287 (3.94), 5.230 (3.88), 5.246 (3.82), 5.865 (5.17), 6.765 (8.88), 6.767 (9.12), 6.786 (10.18), 6.788 (10.05), 6.885 (4.24), 6.904 (9.03), 6.923 (5.30), 7.138 (4.63), 7.142 (4.76), 7.159 (7.78), 7.177 (3.82), 7.180 (3.67), 7.332 (8.89), 7.352 (6.35), 7.659 (1.33), 7.667 (1.60), 7.674 (1.88), 7.682 (3.03), 7.686 (2.92), 7.695 (3.04), 7.703 (3.02), 7.708 (3.04), 7.715 (1.97), 7.723 (1.71), 7.731 (1.56), 7.767 (6.31), 7.790 (12.55), 7.813 (6.93), 8.177 (6.63), 8.192 (7.10), 8.201 (6.80), 8.216 (6.23), 8.914 (15.39), 8.924 (16.00), 8.940 (6.05), 8.961 (5.60).

Example 7

N-[(4S)-3,4-dihydro-2H-chromen-4-yl]-7-methoxy-4-(tetrahydro-2H-pyran-4-yl)-8-(2,3,5-trifluorophenyl)quinoline-3-carboxamide

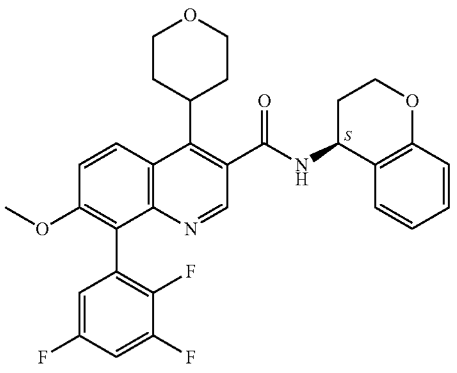

Under argon a vessel was charged with 8-bromo-N-[(4S)-3,4-dihydro-2H-chromen-4-yl]-7-methoxy-4-(tetrahydro-2H-pyran-4-yl)quinoline-3-carboxamide (Intermediate 18A), (200 mg, 0.4 mmol), 2,3,5-trifluorobenzene boronic acid (141 mg, 0.80 mmol), cesium fluoride (182 mg, 1.21 mmol), (2-dicyclohexylphosphino-2',6'-dimethoxybiphenyl) [2-(2'-amino-1,1'-biphenyl)]palladium(II) methanesulfonate (31.4 mg, 40.2 μmol) and a degassed 5:1 mixture of dioxane/water (2 ml), capped and stirred at 60° C. over night. The mixture was treated with aqueous formic acid (0.48 ml, 2.4 mmol) and DMSO and purified by preparative HPLC (RP 18, gradient with 0.1% aqueous formic acid and acetonitrile). The product was suspended in ethanol/water (3:1, 4 ml), stirred over night, filtered off washed with ethanol/water (3:1) and dried in vacuo.

Yield: 138 mg (63% of theory)

LC-MS (Method 2): Rt=1.08 min; MS (ESIpos): m/z=549 [M+H]+

$^1$H-NMR (400 MHz, DMSO-d6) δ [ppm]: 1.669 (0.85), 1.701 (1.34), 1.730 (0.71), 2.036 (0.61), 2.049 (0.74), 2.194 (0.69), 2.205 (0.66), 2.217 (0.67), 2.230 (0.47), 2.365 (0.50), 2.384 (0.44), 2.414 (1.11), 2.433 (1.06), 2.445 (1.10), 2.461 (0.67), 3.462 (0.75), 3.488 (0.82), 3.506 (0.71), 3.534 (1.04), 3.564 (0.54), 3.698 (0.67), 3.931 (16.00), 4.011 (1.49), 4.020 (1.56), 4.037 (1.35), 4.226 (1.03), 4.249 (1.41), 4.258 (1.28), 4.275 (0.99), 5.264 (0.50), 5.279 (1.10), 5.299 (1.12), 5.313 (0.51), 5.753 (0.81), 6.770 (1.91), 6.790 (2.17), 6.898 (1.05), 6.916 (2.21), 6.935 (1.29), 7.049 (0.79), 7.143 (1.04), 7.162 (1.77), 7.180 (0.85), 7.375 (1.84), 7.393 (1.72), 7.521 (0.68), 7.533 (0.71), 7.541 (0.70), 7.716 (2.41), 7.740 (2.55), 8.575 (2.30), 8.599 (2.15), 8.623 (3.23), 8.631 (3.13), 9.082 (1.39), 9.099 (1.37).

TABLE 1

Examples

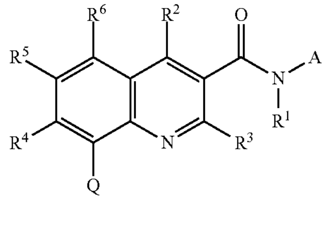

(I)

| Number | R1 | R2 | R3 | R4 | R5 | R6 | Q | A |
|---|---|---|---|---|---|---|---|---|
| 1 | H | 3,6-dihydro-2H-pyran-4-yl | H | H | H | H | 2,3,5-trifluorophenyl | (4S)-3,4-dihydro-2H-chromen-4-yl |
| 2 | H | tetrahydro-2H-pyran-4-yl | H | H | H | H | 2,3,5-trifluorophenyl | (4S)-3,4-dihydro-2H-chromen-4-yl |
| 3 | H | tetrahydro-2H-pyran-4-yl | H | F | H | H | 2,3,5-trifluorophenyl | (4S)-3,4-dihydro-2H-chromen-4-yl |
| 4 | H | ethyl | H | F | H | H | 2,3,5-trifluorophenyl | (4S)-3,4-dihydro-2H-chromen-4-yl |
| 5 | H | 3-fluoroazetidin-1-yl | H | F | H | H | 2,3,5-trifluorophenyl | (4S)-3,4-dihydro-2H-chromen-4-yl |

TABLE 1-continued

Examples

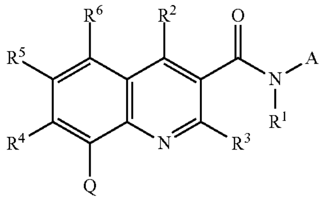

(I)

| Number | R1 | R2 | R3 | R4 | R5 | R6 | Q | A |
|---|---|---|---|---|---|---|---|---|
| 6 | H | 3,6-dihydro-2H-pyran-4-yl | H | F | H | H | 2,3,5-trifluorophenyl | (4S)-3,4-dihydro-2H-chromen-4-yl |
| 7 | H | tetrahydro-2H-pyran-4-yl | H | O—Me | H | H | 2,3,5-trifluorophenyl | (4S)-3,4-dihydro-2H-chromen-4-yl |
| 8 | H | 3-fluoroazetidin-1-yl | H | F | H | H | 2,3,5-trifluorophenyl | 6-fluoro-3,4-dihydro-2H-thiochromen-4-yl |
| 9 | H | 3-fluoroazetidin-1-yl | H | F | H | H | 2,3,5-trifluorophenyl | (4S)-6-methyl-3,4-dihydro-2H-chromen-4-yl |
| 10 | H | 3-fluoroazetidin-1-yl | H | F | H | H | 2,3,5-trifluorophenyl | (4S)-6-fluoro-3,4-dihydro-2H-chromen-4-yl |
| 11 | H | 3-fluoroazetidin-1-yl | H | F | H | H | 2,3,5-trifluorophenyl | (1S)-1,2,3,4-tetrahydronaphthalen-1-yl |
| 12 | H | 3-fluoroazetidin-1-yl | H | F | H | H | 2,3,5-trifluorophenyl | (1S)-2,3-dihydro-1H-inden-1-yl |
| 13 | H | 3-fluoroazetidin-1-yl | H | F | H | H | 2,3,5-trifluorophenyl | (4S)-2,2-dimethyl-3,4-dihydro-2H-chromen-4-yl]- |
| 14 | H | 3-fluoroazetidin-1-yl | H | F | H | H | 2,3,5-trifluorophenyl | (4S)-6-cyano-3,4-dihydro-2H-chromen-4-yl |
| 15 | H | 3-fluoroazetidin-1-yl | H | H | H | H | 2,3,5-trifluorophenyl | (4S)-3,4-dihydro-2H-chromen-4-yl |
| 16 | H | tetrahydro-2H-pyran-4-yl | H | F | H | H | 2,3,5-trifluorophenyl | (1S)-2,3-dihydro-1H-inden-1-yl]- |
| 17 | H | tetrahydro-2H-pyran-4-yl | H | H | H | H | 2,3,5-trifluorophenyl | (rac)-2,3-dihydro-1-benzofuran-3-yl |
| 18 | H | tetrahydro-2H-pyran-4-yl | H | O—iPr | H | H | 2,3,5-trifluorophenyl | (4S)-3,4-dihydro-2H-chromen-4-yl |
| 19 | H | tetrahydro-2H-pyran-4-yl | H | H | H | H | 2,3,5-trifluorophenyl | (1S)-2,3-dihydro-1H-inden-1-yl]- |
| 20 | H | tetrahydro-2H-pyran-4-yl | H | H | H | H | 2,3,5-trifluorophenyl | (1S)-1,2,3,4-tetrahydronaphthalen-1-yl |
| 21 | H | ethyl | H | Cl | H | H | 2,3,5-trifluorophenyl | (4S)-3,4-dihydro-2H-chromen-4-yl |
| 22 | H | ethyl | H | Cl | H | H | 2,3,5-trifluorophenyl | (1S)-2,3-dihydro-1H-inden-1-yl]- |

O—Me represents a methoxy group
O—iPr represents an isopropoxy/i-propoxy group

TABLE la $^1$H-NMR Data

| Number | $^1$H-NMR [δ ppm]; solvent DMSO-$d_6$ |
|---|---|
| 8 | 9.12-9.08 (m, 1H), 8.44 (m, 1H), 8.24-8.20 (m, 2H), 7.64-6.98 (m, 5H), 5.59-5.40 (m, 1H), 5.20-5.18 (m, 1H), 4.68-4.55 (m, 4H), 3.18-3.05 (m, 2H), 2.25-2.15 (m, 2H) |
| 9 | 9.04-9.01 (m, 1H), 8.44 (s, 1H), 8.24-8.20 (m, 1H), 7.64-7.61 (m, 1H), 7.48-7.44 (m, 1H), 7.24-7.18 (m, 1H), 7.10 (s, 1H), 6.98 (m, 1H), 6.69-6.67 (m, 1H), 5.57-5.43 (m, 1H), 5.16-5.13 (m, 1H), 4.72-4.56 (m, 4H), 4.20-4.19 (m, 2H), 2.21 (s, 3H), 2.19-2.12 (m, 1H), 2.03-1.97 (m, 1H) |

TABLE la-continued $^1$H-NMR Data

| Number | $^1$H-NMR [δ ppm]; solvent DMSO-$d_6$ |
|---|---|
| 10 | 9.08-9.05 (m, 1H), 8.46 (s, 1H), 8.24-8.20 (m, 1H), 7.62 (m, 1H), 7.49-7.44 (m, 1H), 7.21 (m, 1H), 7.15-7.11 (m, 1H), 7.02-7.00 (m, 1H), 6.83-6.80 (m, 1H), 5.59-5.40 (m, 1H), 5.16 (m, 1H), 4.69-4.56 (m, 4H), 4.25-4.22 (m, 2H), 2.15 (m, 1H), 2.01 (m, 1H) |
| 11 | 8.96-8.93 (m, 1H), 8.41 (s, 1H), 8.24-8.20 (m, 1H), 7.66-7.59 (m, 1H), 7.48-7.43 (m, 1H), 7.34-7.30 (m, 1H), 7.23-7.10 (m, 4H), 5.60-5.41 (m, 1H), 5.20-5.12 (m, 1H), 4.72-4.54 (m, 4H), 2.78-2.75 (m, 2H), 2.08-1.76 (m, 4H) |

TABLE la-continued

| $^{1}$H-NMR Data | |
|---|---|
| Number | $^{1}$H-NMR [δ ppm]; solvent DMSO-$d_6$ |
| 12 | 8.91-8.88 (m, 1H), 8.45 (m, 1H), 8.24-8.20 (m, 1H), 7.62 (m, 1H), 7.48-7.44 (m, 1H), 7.36-7.34 (m, 1H), 7.28-7.19 (m, 4H), 5.59-5.42 (m, 1H), 5.49-5.47 (m, 1H), 6.65 (m, 4H), 2.98 (m, 1H), 2.85 (m, 1H), 2.50 (m, 1H), 1.94 (m, 1H) |
| 13 | 8.94-8.90 (m, 1H), 8.49-8.48 (m, 1H), 8.25-8.22 (m, 1H), 7.79-7.13 (m, 5H), 6.91-6.88 (m, 1H), 6.76-6.74 (m, 1H), 5.63-4.94 (m, 1H), 5.32-5.26 (m, 1H), 4.65 (m, 4H), 2.19-2.15 (m, 1H), 1.89-1.81 (m, 1H), 1.41 (s, 3H), 1.30 (s, 3H) |
| 14 | 9.08-9.05 (m, 1H), 8.54 (s, 1H), 8.25-8.21 (m, 1H), 7.83 (m, 1H), 7.65-7.44 (m, 3H), 7.23-7.21 (m, 1H), 6.99-6.96 (m, 1H), 5.57-5.41 (m, 1H), 5.18-5.16 (m, 1H), 4.63 (m, 4H), 4.38-4.32 (m, 2H), 2.21-2.15 (m, 1H), 2.09-2.03 (m, 1H) |
| 15 | 9.06-9.04 (m, 1H), 8.44 (s, 1H), 8.15-8.12 (m, 1H), 7.71-7.70 (m, 1H), 7.60-7.50 (m, 2H), 7.32-7.30 (m, 1H), 7.19-7.15 (m, 2H), 6.92-6.89 (m, 1H), 6.81-6.79 (m, 1H), 5.59-5.40 (m, 1H), 5.20 (m, 1H), 4.65 (m, 4H), 4.27-4.24 (m, 2H), 2.16 (m, 1H), 2.04 (m, 1H) |
| 16 | $^{1}$H-NMR (400 MHz, DMSO-d6) δ [ppm]: −0.008 (1.15), 0.008 (1.60), 1.234 (0.80), 1.261 (0.90), 1.279 (0.70), 1.297 (0.45), 1.336 (0.40), 1.681 (3.75), 1.711 (5.95), 1.750 (2.25), 1.875 (0.75), 1.896 (2.20), 1.915 (3.05), 1.928 (3.10), 1.946 (3.45), 1.964 (2.25), 1.984 (0.90), 2.328 (0.45), 2.367 (1.90), 2.375 (1.85), 2.406 (5.05), 2.436 (5.05), 2.476 (2.10), 2.557 (2.85), 2.567 (1.55), 2.670 (0.50), 2.710 (0.70), 2.823 (1.60), 2.843 (2.95), 2.863 (4.20), 2.882 (5.65), 2.903 (2.55), 2.944 (1.90), 2.953 (3.60), 2.965 (3.65), 2.975 (3.75), 2.985 (2.75), 2.993 (2.30), 3.004 (2.00), 3.014 (1.90), 3.024 (1.05), 3.393 (1.30), 3.421 (2.15), 3.437 (1.90), 3.464 (2.55), 3.496 (2.45), 3.523 (3.35), 3.549 (3.35), 3.575 (1.60), 3.722 (2.25), 3.975 (2.15), 4.002 (7.60), 4.029 (5.40), 5.542 (1.55), 5.556 (4.15), 5.561 (4.35), 5.575 (4.25), 5.581 (4.15), 5.594 (1.55), 5.600 (1.40), 7.226 (7.90), 7.235 (9.55), 7.239 (10.65), 7.248 (15.35), 7.264 (11.85), 7.276 (8.85), 7.286 (6.15), 7.296 (4.00), 7.444 (3.80), 7.451 (6.20), 7.463 (5.40), 7.472 (3.35), 7.643 (1.45), 7.650 (1.75), 7.658 (2.05), 7.665 (3.25), 7.670 (3.15), 7.678 (3.20), 7.687 (3.20), 7.692 (3.25), 7.699 (2.05), 7.707 (1.80), 7.715 (1.80), 7.761 (4.90), 7.784 (9.40), 7.807 (5.10), 8.664 (3.95), 8.679 (4.40), 8.685 (4.35), 8.701 (3.75), 8.756 (15.95), 8.769 (16.00), 9.026 (8.30), 9.047 (8.30). |
| 17 | $^{1}$H-NMR (400 MHz, DMSO-d6) δ [ppm]: 1.673 (3.95), 1.703 (4.33), 2.338 (0.57), 2.351 (0.90), 2.368 (1.83), 2.381 (2.48), 2.398 (2.36), 2.413 (2.51), 2.425 (1.71), 2.443 (0.97), 3.163 (0.55), 3.176 (0.57), 3.390 (1.09), 3.419 (1.99), 3.447 (1.11), 3.501 (1.48), 3.530 (2.79), 3.557 (1.54), 3.689 (1.43), 3.969 (2.16), 3.980 (2.65), 3.998 (4.27), 4.015 (2.36), 4.026 (1.94), 4.390 (3.45), 4.402 (3.59), 4.414 (3.89), 4.427 (3.86), 4.784 (3.39), 4.808 (5.50), 4.830 (3.16), 5.794 (1.35), 5.807 (1.72), 5.814 (2.45), 5.826 (2.43), 5.833 (1.71), 5.846 (1.31), 6.858 (5.14), 6.877 (5.82), 6.933 (2.82), 6.952 (6.04), 6.970 (3.37), 7.205 (2.09), 7.223 (4.58), 7.240 (5.54), 7.261 (2.25), 7.486 (4.92), 7.505 (4.64), 7.568 (0.69), 7.575 (0.85), 7.583 (1.01), 7.590 (1.61), 7.595 (1.56), 7.603 (1.66), 7.611 (1.60), 7.616 (1.65), 7.624 (1.03), 7.631 (0.90), 7.639 (0.81), 7.769 (2.44), 7.787 (4.80), 7.808 (4.74), 7.832 (6.61), 7.848 (3.23), 8.551 (4.14), 8.571 (3.88), 8.704 (16.00), 9.334 (4.98), 9.353 (4.87). |
| 18 | $^{1}$H-NMR (400 MHz, DMSO-d6) δ [ppm]: 0.853 (0.48), 1.198 (13.84), 1.213 (16.00), 1.232 (11.46), 1.234 (11.69), 1.259 (0.90), 1.284 (0.74), 1.298 (0.85), 1.669 (1.36), 1.701 (1.98), 1.730 (1.01), 2.016 (0.76), 2.023 (0.78), 2.041 (1.82), 2.051 (1.13), 2.195 (1.01), 2.206 (1.01), 2.217 (0.99), 2.229 (0.74), 2.366 (0.81), 2.384 (0.64), 2.412 (1.52), 2.444 (1.52), 2.458 (0.97), 2.524 (1.54), 2.710 (0.44), 3.431 (0.44), 3.457 (1.06), 3.485 (1.17), 3.501 (1.01), 3.530 (1.54), 3.558 (0.78), 3.692 (0.97), 4.008 (2.16), 4.018 (2.23), 4.035 (1.93), 4.201 (0.53), 4.227 (1.47), 4.250 (2.07), 4.260 (1.82), 4.276 (1.43), 4.808 (0.76), 4.823 (1.96), 4.838 (2.67), 4.853 (2.00), 4.868 (0.78), 5.266 (0.76), 5.280 (1.63), 5.300 (1.66), 5.314 (0.74), 5.754 (0.64), 6.772 (3.20), 6.792 (3.59), 6.898 (1.66), 6.901 (1.66), 6.917 (3.38), 6.920 (3.27), 6.935 (2.12), 6.938 (1.96), 7.005 (1.20), 7.013 (1.27), 7.142 (1.59), 7.146 (1.68), 7.164 (2.60), 7.180 (1.29), 7.184 (1.27), 7.375 (2.72), 7.394 (2.51), 7.488 (0.51), 7.497 (0.60), 7.504 (0.69), 7.511 (1.11), 7.516 (1.06), 7.524 (1.11), 7.533 (1.06), 7.538 (1.13), 7.545 (0.74), 7.552 (0.67), 7.560 (0.62), 7.700 (3.66), 7.724 (3.94), 8.520 (3.57), 8.545 (3.34), 8.611 (6.40), 8.620 (6.47), 9.069 (2.12), 9.087 (2.07). |
| 19 | $^{1}$H-NMR (500 MHz, DMSO-d6) δ [ppm]: 0.007 (1.68), 1.233 (0.62), 1.687 (2.11), 1.716 (3.74), 1.745 (2.10), 1.901 (0.79), 1.917 (1.98), 1.926 (1.14), 1.933 (2.11), 1.942 (2.20), 1.949 (1.07), 1.958 (2.08), 1.975 (0.84), 2.411 (1.34), 2.426 (2.95), 2.435 (3.12), 2.451 (3.20), 2.459 (3.05), 2.516 (2.87), 2.524 (2.01), 2.834 (1.06), 2.850 (1.95), 2.865 (2.43), 2.881 (3.10), 2.898 (1.39), 2.957 (1.79), 2.965 (1.88), 2.975 (1.91), 2.982 (1.83), 2.989 (1.27), 2.997 (1.17), 3.006 (1.16), 3.014 (0.97), 3.419 (0.99), 3.439 (1.64), 3.462 (0.97), 3.514 (1.31), 3.535 (2.40), 3.559 (1.31), 3.723 (1.22), 3.990 (2.26), 3.998 (2.65), 4.014 (4.01), 4.029 (2.13), 5.557 (1.29), 5.572 (3.67), 5.587 (3.59), 5.603 (1.22), 7.217 (2.47), 7.224 (3.20), 7.232 (7.98), 7.239 (8.00), 7.244 (8.35), 7.250 (10.18), 7.258 (2.94), 7.268 (4.61), 7.276 (3.02), 7.285 (1.66), 7.458 (3.35), 7.465 (3.32), 7.475 (2.78), 7.588 (0.79), 7.594 (0.97), 7.600 (1.16), 7.606 (1.74), 7.616 (1.81), 7.622 (1.73), 7.627 (1.71), 7.632 (1.11), 7.638 (0.91), 7.645 (0.82), 7.780 (2.87), 7.794 (5.08), 7.811 (4.88), 7.836 (6.42), 7.848 (3.62), 8.564 (4.16), 8.581 (4.01), 8.739 (16.00), 9.046 (4.70), 9.063 (4.56). |
| 20 | $^{1}$H-NMR (500 MHz, DMSO-d6) δ [ppm]: 1.685 (2.18), 1.710 (2.36), 1.750 (2.20), 1.776 (3.08), 1.836 (1.45), 1.859 (1.65), 1.865 (1.59), 1.879 (1.79), 1.896 (1.45), 1.926 (1.79), 1.938 (1.56), 1.951 (1.16), 2.056 (1.72), 2.067 (1.81), 2.080 (1.41), 2.362 (0.43), 2.44 1 (3.08), 2.465 (3.29), 2.636 (0.45), 2.711 (0,68), 2.733 (2.33), 2.745 (5.26), 2.755 (4.92), 2.767 (2.06), 2.789 (0.54), 3.472 (1.31), 3.493 (2.40), 3.523 (1.93), 3.549 (2.67), 3.571 (1.50), 3.728 (1.38), 4.021 (3.22), 4.033 (4.44), 5.258 (1.18), 5.271 (2.47), 5.286 (2.45), 5.299 (1.20), 7.102 (3.44), 7.116 (4.96), 7.165 (1.90), 7.176 (4.67), 7.189 (6.35), 7.193 (6.03), 7.204 (5.21), 7.220 (3.63), 7.428 (4.56), 7.442 (4.06), 7.586 (0.86), 7.604 (1.88), 7.614 (1.88), 7.625 (1.86), 7.636 (0.95), 7.643 (0.84), 7.776 (2.97), 7.791 (5.46), 7.808 (5.19), 7.830 (6.96), 7.844 (3.90), 8.563 (4.51), 8.580 (4.33), 8.722 (16.00), 9.060 (4.99), 9.078 (4.80). |
| 21 | $^{1}$H-NMR (400 MHz, DMSO-d6) δ [ppm]: −0.149 (0.49), −0.008 (4.06), 0.008 (4.51), 0.146 (0.51), 1.292 (7.17), 1.311 (16.00), 1.329 (7.45), 1.998 (0.67), 2.006 (1.12), 2.013 (1.21), 2.031 (1.50), 2.041 (1.63), 2.047 (1.84), 2.055 (1.38), 2.062 (1.03), 2.164 (0.78), 2.174 (1.35), 2.185 (1.78), 2.197 (1.68), 2.207 (1.68), 2.220 (1.11), 2.229 (0.93), 2.240 (0.59), 2.327 (0.52), 2.366 (0.59), 2.523 (2.43), 2.670 (0.55), 2.710 (0.60), 3.197 (0.42), 3.230 (2.70), 3.239 (3.57), 3.249 (3.83), 3.258 (3.60), 3.269 (2.77), 3.293 (1.12), 4.200 (0.88), 4.207 (0.72), 4.220 (2.02), 4.227 (2.93), 4.246 (3.99), 4.252 (4.40), 4.268 (2.90), 4.280 (0.77), 4.287 (0.95), 4.296 (0.62), 5.262 (1.14), 5.276 (2.64), 5.295 (2.61), 5.310 (1.16), 6.771 (4.95), 6.774 (5.34), 6.792 (5.65), 6.794 (5.85), 6.892 (2.62), 6.895 (2.66), 6.910 (5.57), 6.913 (5.51), 6.929 (3.39), 6.932 (3.24), 7.139 (2.70), 7.143 (2.92), 7.160 (4.42), 7.178 (2.22), 7.182 (2.23), 7.198 (1.34), 7.203 (1.69), 7.211 |

TABLE 1a-continued

| $^1$H-NMR Data | |
|---|---|
| Number | $^1$H-NMR [δ ppm]; solvent DMSO-$d_6$ |
| | (2.00), 7.217 (1.86), 7.224 (1.96), 7.232 (1.81), 7.237 (1.30), 7.323 (2.51), 7.336 (2.64), 7.351 (2.33), 7.632 (0.78), 7.639 (0.95), 7.647 (1.09), 7.654 (1.73), 7.659 (1.63), 7.667 (1.71), 7.676 (1.73), 7.681 (1.79), 7.688 (1.14), 7.696 (1.03), 7.704 (0.98), 7.895 (8.41), 7.918 (8.95), 8.412 (8.99), 8.435 (8.11), 8.785 (10.53), 8.792 (10.31), 9.121 (4.43), 9.142 (4.35). |
| 22 | $^1$H-NMR (400 MHz, DMSO-d6) δ [ppm]: −0.008 (1.41), 0.008 (1.68), 1.295 (7.38), 1.312 (15.52), 1.314 (15.82), 1.330 (7.53), 1.861 (0.55), 1.873 (0.58), 1.883 (1.57), 1.894 (1.98), 1.904 (2.16), 1.914 (3.22), 1.926 (2.28), 1.935 (2.25), 1.946 (.75), 1.956 (0.76), 1.967 (0.66), 2.323 (0.69), 2.327 (0.97), 2.366 (0.48), 2.523 (4.90), 2.670 (0.90), 2.710 (0.46), 2.815 (1.21), 2.836 (2.16), 2.856 (3.09), 2.875 (4.24), 2.896 (1.95), 2.941 (2.25), 2.962 (2.28), 2.970 (1.83), 2.980 (1.26), 3.002 (1.14), 3.243 (3.84), 3.251 (4.02), 3.261 (3.81), 3.266 (3.97), 5.530 (1.59), 5.550 (4.69), 5.569 (4.69), 5.589 (1.59), 7.204 (3.13), 7.214 (10.08), 7.223 (9.25), 7.230 (10.59), 7.236 (16.00), 7.248 (4.33), 7.257 (6.54), 7.268 (3.67), 7.278 (1.95), 7.369 (2.65), 7.377 (4.26), 7.386 (3.49), 7.633 (1.05), 7.640 (1.24), 7.648 (1.44), 7.656 (2.28), 7.661 (2.14), 7.669 (2.23), 7.677 (2.16), 7.682 (2.28), 7.689 (1.45), 7.697 (1.27), 7.705 (1.24), 7.896 (11.22), 7.919 (11.95), 8.412 (10.23), 8.435 (9.24), 8.786 (13.89), 8.795 (13.66), 8.994 (4.45), 9.013 (4.39). |

TABLE 2a

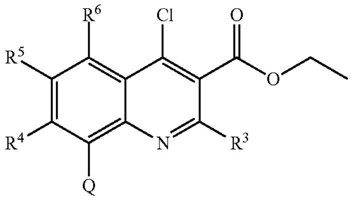

1Q-OEt

| Number | R3 | R4 | R5 | R6 | Q |
|---|---|---|---|---|---|
| 1Q-1 | H | H | H | H | 2,3,5-trifluorophenyl |
| 1Q-2 | H | F | H | H | 2,3,5-trifluorophenyl |
| 1Q-3 | H | Cl | H | H | 2,3,5-trifluorophenyl |

TABLE 2b

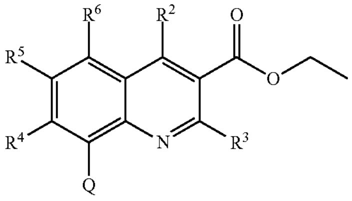

1U-OEt

| Number | R2 | R3 | R4 | R5 | R6 | Q |
|---|---|---|---|---|---|---|
| 1U-1 | tetrahydro-2H-pyran-4-yl | H | F | H | H | 2,3,5-trifluorophenyl |
| 1U-2 | tetrahydro-2H-pyran-4-yl | H | H | H | H | 2,3,5-trifluorophenyl |
| 1U-3 | tetrahydro-2H-pyran-4-yl | H | Cl | H | H | 2,3,5-trifluorophenyl |

TABLE 2b-continued

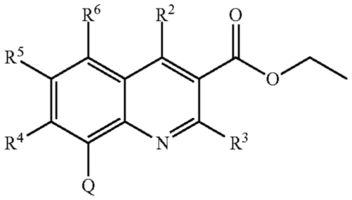

1U-OEt

| Number | R2 | R3 | R4 | R5 | R6 | Q |
|---|---|---|---|---|---|---|
| 1U-4 | 3,6 dihydro-2H-pyran-4-yl | H | F | H | H | 2,3,5-trifluorophenyl |
| 1U-5 | 3,6 dihydro-2H-pyran-4-yl | H | H | H | H | 2,3,5-trifluorophenyl |
| 1U-6 | 3,6 dihydro-2H-pyran-4-yl | H | Cl | H | H | 2,3,5-trifluorophenyl |
| 1U-7 | ethyl | H | F | H | H | 2,3,5-trifluorophenyl |
| 1U-8 | ethyl | H | Cl | H | H | 2,3,5-trifluorophenyl |
| 1U-9 | 3-fluoroazetidin-1-yl | H | F | H | H | 2,3,5-trifluorophenyl |
| 1U-10 | 3-fluoroazetidin-1-yl | H | H | H | H | 2,3,5-trifluorophenyl |
| 1U-11 | 3-fluoroazetidin-1-yl | H | Cl | H | H | 2,3,5-trifluorophenyl |

TABLE 2c

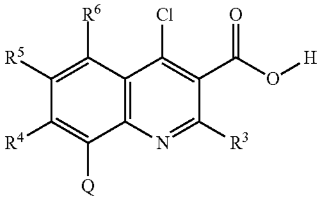

1R

| Number | R3 | R4 | R5 | R6 | Q |
|---|---|---|---|---|---|
| 1R-1 | H | H | H | H | 2,3,5-trifluorophenyl |
| 1R-2 | H | F | H | H | 2,3,5-trifluorophenyl |
| 1R-3 | H | Cl | H | H | 2,3,5-trifluorophenyl |

TABLE 2d

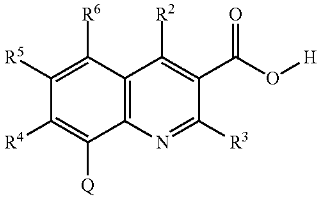

1W

| Number | R2 | R3 | R4 | R5 | R6 | Q |
|---|---|---|---|---|---|---|
| 1W-1 | tetrahydro-2H-pyran-4-yl | H | F | H | H | 2,3,5-trifluorophenyl |
| 1W-2 | tetrahydro-2H-pyran-4-yl | H | H | H | H | 2,3,5-trifluorophenyl |
| 1W-3 | tetrahydro-2H-pyran-4-yl | H | Cl | H | H | 2,3,5-trifluorophenyl |
| 1W-4 | 3,6 dihydro-2H-pyran-4-yl | H | F | H | H | 2,3,5-trifluorophenyl |

TABLE 2d-continued

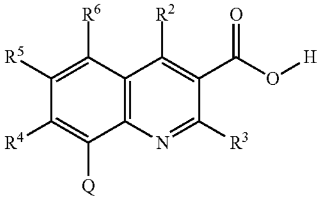

1W

| Number | R2 | R3 | R4 | R5 | R6 | Q |
|---|---|---|---|---|---|---|
| 1W-5 | 3,6 dihydro-2H-pyran-4-yl | H | H | H | H | 2,3,5-trifluorophenyl |
| 1W-6 | 3,6 dihydro-2H-pyran-4-yl | H | Cl | H | H | 2,3,5-trifluorophenyl |
| 1W-7 | ethyl | H | F | H | H | 2,3,5-trifluorophenyl |
| 1W-8 | ethyl | H | Cl | H | H | 2,3,5-trifluorophenyl |
| 1W-9 | 3-fluoroazetidin-1-yl | H | F | H | H | 2,3,5-trifluorophenyl |
| 1W-10 | 3-fluoroazetidin-1-yl | H | H | H | H | 2,3,5-trifluorophenyl |
| 1W-11 | 3-fluoroazetidin-1-yl | H | Cl | H | H | 2,3,5-trifluorophenyl |

TABLE 2f

| $^1$H-NMR Data | |
|---|---|
| Number | $^1$H-NMR [δ ppm]; solvent DMSO-$d_6$ |
| 1T-18 | 9.09-9.07 (m, 1H), 8.55 (s, 1H), 8.05-8.02 (m, 2H), 7.34-7.29 (m, 2H), 7.21-7.16 (m, 1H), 6.95-6.91 (m, 1H), 6.82-6.80 (m, 1H), 5.54-5.40 (m, 1H), 5.24-5.21 (m, 1H), 4.70-4.54 (m, 4H), 4.29-4.26 (m, 2H), 2.21-2.16 (m, TH), 2.07-2.02 (m, 1H) |
| 1T-21 | 8.96-8.94 (m, 1H), 8.58 (s, 1H), 8.11-8.08 (m, 1H), 7.44-7.23 (m, 5H), 5.55-5.40 (m, 2H), 4.69-4.56 (m, 4H), 3.00-2.97 (m, 1H), 2.88-2.84 (m, 1H), 2.50 (m, 1H), 1.98-1.92 (m, 1H) |
| 1T-24 | 9.15-9.13 (m, 1H), 8.57 (s, 1H), 8.12-8.08 (m, 1H), 7.44-7.40 (m, 1H), 7.23-7.16 (m, 2H), 7.10-7.05 (m, 1H), 5.55-5.40 (m, 1H), 5.22-5.21 (m, 1H), 4.68-4.54 (m, 4H), 3.17-3.09 (m, 2H), 2.26-2.15 (m, 2H) |
| 1T-27 | 9.00-8.98 (m, 1H), 8.55 (s, 1H), 8.11-8.08 (m, 1H), 7.44-7.12 (m, 5H), 5.59-5.41 (m, 1H), 5.19 (m, 1H), 4.67-4.56 (m, 4H), 2.80-2.73 (m, 2H), 2.03-1.74 (m, 4H) |
| 1T-29 | 9.12-9.10 (m, 1H), 8.65 (s, 1H), 8.12-8.08 (m, 1H), 7.86 (m, 1H), 7.66-7.63 (m, 1H), 7.44-7.40 (m, 1H), 7.00-6.98 (m, 1H), 5.55-5.39 (m, 1H), 5.22-5.17 (m, 1H), 4.70-4.57 (m, 4H), 4.42-4.33 (m, 2H), 2.22-2.17 (m, 1H), 2.11-2.05 (m, 1H) |

TABLE 2e

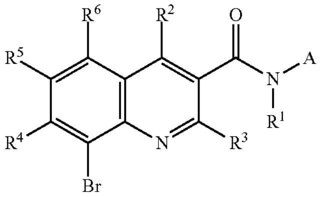

1T-Br

| Number | R1 | R2 | R3 | R4 | R5 | R6 | A |
|---|---|---|---|---|---|---|---|
| 1T-1 | H | tetrahydro-2H-pyran-4-yl | H | H | H | H | (4S)-3,4-dihydro-2H-chromen-4-yl |
| 1T-2 | H | tetrahydro-2H-pyran-4-yl | H | H | H | H | (1S)-2,3-dihydro-1H-inden-1-yl |
| 1T-3 | H | tetrahydro-2H-pyran-4-yl | H | F | H | H | (4S)-3,4-dihydro-2H-chromen-4-yl |
| 1T-4 | H | tetrahydro-2H-pyran-4-yl | H | F | H | H | (1S)-2,3-dihydro-1H-inden-1-yl |
| 1T-5 | H | tetrahydro-2H-pyran-4-yl | H | Cl | H | H | (4S)-3,4-dihydro-2H-chromen-4-yl |
| 1T-6 | H | tetrahydro-2H-pyran-4-yl | H | Cl | H | H | (1S)-2,3-dihydro-1H-inden-1-yl |
| 1T-7 | H | 3,6 dihydro-2H-pyran-4-yl | H | H | H | H | (4S)-3,4-dihydro-2H-chromen-4-yl |
| 1T-8 | H | 3,6 dihydro-2H-pyran-4-yl | H | H | H | H | (1S)-2,3-dihydro-1H-inden-1-yl |
| 1T-9 | H | 3,6 dihydro-2H-pyran-4-yl | H | F | H | H | (4S)-3,4-dihydro-2H-chromen-4-yl |
| 1T-10 | H | 3,6 dihydro-2H-pyran-4-yl | H | F | H | H | (1S)-2,3-dihydro-1H-inden-1-yl |
| 1T-11 | H | 3,6 dihydro-2H-pyran-4-yl | H | Cl | H | H | (4S)-3,4-dihydro-2H-chromen-4-yl |
| 1T-12 | H | 3,6 dihydro-2H-pyran-4-yl | H | Cl | H | H | (1S)-2,3-dihydro-1H-inden-1-yl |
| 1T-13 | H | ethyl | H | H | H | H | (1S)-2,3-dihydro-1H-inden-1-yl |
| 1T-14 | H | ethyl | H | F | H | H | (4S)-3,4-dihydro-2H-chromen-4-yl |
| 1T-15 | H | ethyl | H | F | H | H | (1S)-2,3-dihydro-1H-inden-1-yl |
| 1T-16 | H | ethyl | H | Cl | H | H | (4S)-3,4-dihydro-2H-chromen-4-yl |
| 1T-17 | H | ethyl | H | Cl | H | H | (1S)-2,3-dihydro-1H-inden-1-yl |
| 1T-18 | H | 3-fluoroazetidin-1-yl | H | H | H | H | (4S)-3,4-dihydro-2H-chromen-4-yl |
| 1T-19 | H | 3-fluoroazetidin-1-yl | H | H | H | H | (1S)-2,3-dihydro-1H-inden-1-yl |
| 1T-20 | H | 3-fluoroazetidin-1-yl | H | F | H | H | (4S)-3,4-dihydro-2H-chromen-4-yl |
| 1T-21 | H | 3-fluoroazetidin-1-yl | H | F | H | H | (1S)-2,3-dihydro-1H-inden-1-yl |
| 1T-22 | H | 3-fluoroazetidin-1-yl | H | Cl | H | H | (4S)-3,4-dihydro-2H-chromen-4-yl |
| 1T-23 | H | 3-fluoroazetidin-1-yl | H | Cl | H | H | (1S)-2,3-dihydro-1H-inden-1-yl |
| 1T-24 | H | 3-fluoroazetidin-1-yl | H | F | H | H | 6-fluoro-3,4-dihydro-2H-thiochromen-4-yl |
| 1T-25 | H | 3-fluoroazetidin-1-yl | H | F | H | H | (4S)-6-methyl-3,4-dihydro-2H-chromen-4-yl |
| 1T-26 | H | 3-fluoroazetidin-1-yl | H | F | H | H | (4S)-6-fluoro-3,4-dihydro-2H-chromen-4-yl |
| 1T-27 | H | 3-fluoroazetidin-1-yl | H | F | H | H | (1S)-1,2,3,4-tetrahydronaphthalen-1-yl |
| 1T-28 | H | 3-fluoroazetidin-1-yl | H | F | H | H | (4S)-2,2-dimethyl-3,4-dihydro-2H-chromen-4-yl]- |
| 1T-29 | H | 3-fluoroazetidin-1-yl | H | F | H | H | (4S)-6-cyano-3,4-dihydro-2H-chromen-4-yl |

Experimental Section—Biological Assays

Examples were tested in selected biological assays one or more times. When tested more than once, data are reported as either average values or as median values, wherein

- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

In Vitro Assay 1: *C. elegans* Slo-1a—Action at a Recombinant *C. elegans* Cell Line Generation of a Stable *C. elegans* CHO Cell Line A CHO cell line was obtained from ATCC, code ATCC CRL-9096. For transfection with plasmid DNA to express *C. elegans* Slo-1a (accession number AAL28102) CHO cells were passaged to 40% confluence before adding the transfection solution to the cell culture. The transfection solution included 300 μL OptiMEM (Life Technologies, Nr.: 31985), 2 μL (=6 μg) of plasmid DNA containing the *C. elegans* Slo 1a gene and 9 μL FugeneHD (Promega, Nr.: E2311), and was added to the cells prior to incubation for 48 hours at 37° C., 5% $CO_2$. The transfection medium was exchanged for the selection medium which contains additional G418 (2 mg/ml, Invitrogen, Nr.: 10131) and the cells were seeded into 384 well plates (300 cells/well). After a few weeks, the remaining surviving cells were tested with a voltage sensitive dye (Membrane Potential Assay Kit, Molecular Devices Nr.: R8034) for K+ channel expression. Positive cell clones were purified by the limited dilution technique. For this the clone with the highest and most robust signal in the voltage sensitive dye assay was further subcloned (incubated) in 384 well plates (0.7 cells/well) in order to obtain clonal purity. This generated a final stable CHO cell line expressing the *C. elegans* Slo-1a.

Cell Culture Conditions

Cells were cultured at 37° C., and 5% $CO_2$ in MEMalpha with Glutamax I (Invitrogen, Nr.: 32571), supplemented with 10% (v/v) heat inactivated fetal bovine serum (Invitrogen, Nr.: 10500), G418 (1 mg/ml. Invitrogen. Nr.: 10131). Cells were detached using Accutase (Sigma. Nr.: A6964).

Membrane Potential Measurements

Laboratory compound testing was performed on 384-well microtiter plates (MTPs, Greiner, Nr.: 781092), 8000 cells/well were plated onto 384-well MTPs and cultured for 20 to 24 hours at 37° C., and 5% $CO_2$. After removal of the cell culture medium, the cells were washed once with tyrode (150 mM NaCl, 0.3 mM KCl, 2 mM $CaCl_2$. 1 mM $MgCl_2$. 0.8 mM $NaH_2PO_4$, 5 mM Glucose, 28 mM Hepes, pH 7.4) and then loaded with the voltage sensitive dye of the Membrane Potential Assay Kit diluted in tyrode for 1 h at room temperature.

After starting the measurement of fluorescence using a FLIPR Tetra (Molecular Devices, Exc. 510-545 nm, Emm. 565-625 nm), test compounds were added followed by the addition of KCl tyrode (final assay concentration: 70 mM KCl, 2 mM $CaCl_2$, 1 mM $MgCl_2$, 0.8 mM $NaH_2PO_4$, 5 mM Glucose, 28 mM Hepes, pH 7.4, including the voltage sensitive dye). The measurement was completed after 7 minutes.

Statistics

The data were evaluated by using the ActivityBase XLfit software (IDBS) for curve fitting and calculation of the half-maximal effective concentration ($EC_{50}$) and are reported as negative decadic logarithm ($pE_{50}$).

For the following examples, $pE_{50}$>6.5-7.5 has been found for: 14.

For the following examples, $pE_{50}$>7.5-8.5 has been found for: 5, 13.

For the following examples, $pE_{50}$>8.5 has been found for: 1, 2, 4, 7, 10, 11, 12, 15, 16, 19, 21.

In Vitro Assay 2: *D. immitis* Slo-1—Action at a Recombinant *D. immitis* Cell Line Generation of a Stable *D. immitis*_Slo-1 CHO Cell Line A CHO cell line was obtained from ATCC, code ATCC CRL-9096. For transfection with plasmid DNA to express *D. immitis* Slo-1 (based on Protein sequence JQ730003, codon optimized for hamster) CHO cells were passaged to 40% confluence before adding the transfection solution to the cell culture. The transfection solution included 300 μL OptiMEM (Life Technologies, Nr.: 31985), 2 μL (=6 μg) of plasmid DNA containing the *D. immitis* Slo-1 gene and 9 μL FugeneHD (Promega, Nr.: E2311), and was added to the cells prior to incubation for 48 hours at 37° C., 5% $CO_2$. The transfection medium was exchanged for the selection medium which contains additional G418 (2 mg/ml, Invitrogen, Nr.: 10131) and the cells were seeded into 384 well plates (300 cells/well). After a few weeks, the remaining surviving cells were tested with a voltage sensitive dye (Membrane Potential Assay Kit, Molecular Devices Nr.: R8034) for K+ channel expression. Positive cell clones were purified by the limited dilution technique. For this the clone with the highest and most robust signal in the voltage sensitive dye assay was further subcloned (incubated) in 384 well plates (0.7 cells/well) in order to obtain clonal purity. This generated a final stable CHO cell line expressing the *D. immitis* Slo-1.

Cell Culture Conditions

Cells were cultured at 37° C., and 5% $CO_2$ in MEMalpha with Glutamax I (Invitrogen, Nr.: 32571), supplemented with 10% (v/v) heat inactivated fetal bovine serum (Invitrogen, Nr.: 10500), G418 (I mg/ml, Invitrogen, Nr.: 10131). Cells were detached using Accutase (Sigma, Nr.: A6964).

Membrane Potential Measurements

Laboratory compound testing was performed on 384-well microtiter plates (MTPs, Greiner, Nr.: 781092), 8000 cells/well were plated onto 384-well MTPs and cultured for 20 to 24 hours at 37° C., and 5% $CO_2$. After removal of the cell culture medium, the cells were washed once with tyrode (150 mM NaCl, 0.3 mM KCl, 2 mM $CaCl_2$, 1 mM $MgCl_2$, 0.8 mM $NaH_2PO_4$, 5 mM Glucose, 28 mM Hepes, pH 7.4) and then loaded with the voltage sensitive dye of the Membrane Potential Assay Kit diluted in tyrode for 1 h at room temperature.

After starting the measurement of fluorescence using a FLIPR Tetra (Molecular Devices, Exc. 510-545 nm, Emm. 565-625 nm), test compounds were added followed by the addition of KCl tyrode (final assay concentration: 70 mM KCl, 2 mM $CaCl_2$), 1 mM $MgCl_2$, 0.8 mM $NaH_2PO_4$, 5 mM Glucose, 28 mM Hepes, pH 7.4, including the voltage sensitive dye). The measurement was completed after 7 minutes.

Statistics

The data were evaluated by using the ActivityBase XLfit software (IDBS) for curve fitting and calculation of the half-maximal effective concentration ($EC_{50}$) and are reported as negative decadic logarithm ($pE_{50}$).

For the following examples, $pE_{50}$>5.3-6.5 has been found for: 8, 9, 13, 14, 17, 18, 19.

For the following examples, $pE_{50}$>6.5-7.5 has been found for: 1, 10, 12, 15, 20.

For the following examples, $pE_{50}$>7.5-8.5 has been found for: 2, 3, 4, 5, 6, 7, 16, 22.

In Vitro Assay 3: *Nippostrongylus Brasiliensis* (NIPOBR)

Adult *Nippostrongylus brasiliensis* were washed with saline buffer containing 100 U/ml penicillin, 0.1 mg/ml streptomycin and 2.5 μg/ml amphotericin B. Test compounds were dissolved in DMSO and worms were incubated in medium in a final concentration of 10 μg/ml (10 ppm) respectively 1 μg/ml (1 ppm). An aliquot of the medium was used to determine the acetylcholine esterase activity in comparison to a negative control. The principle of measuring acetylcholine esterase as readout for anthelmintic activity was described in Rapson et al (1986) and Rapson et al (1987).

For the following examples, activity (reduction of AChE compared to negative control) was higher than 80% at 10 μg/ml: 2, 3, 4, 5, 6, 7, 8, 9, 10, 11, 12, 13, 14, 15, 16, 17, 18, 19, 20, 21, 22.

For the following examples, activity (reduction of AChE compared to negative control) was higher than 80% at 1 μg/ml: 1, 2, 3, 4, 5, 6, 7, 9, 10, 11, 12, 15, 16, 17, 18, 19, 20, 21, 22.

In Vitro Assay 4: *Dirofilaria immitis* Microfilariae (DIROIM L1)

≥250 *Dirofilaria immitis* microfilariae, which were freshly purified from blood, were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Efficacy was determined as the reduction of motility in comparison to the negative control. Based on the evaluation of a wide concentration range, concentration-response curves as well as $EC_{50}$-values were calculated.

For the following examples, the EC50 was <0.1 ppm: 1, 2, 3, 4, 5, 6, 7, 8, 9, 10, 11, 12, 13, 14, 15, 16, 17, 18, 19, 20, 21, 22.

In Vitro Assay 5: *Dirofilaria immitis* (DIROIM L4)

10 *Dirofilaria immitis* third-stage larvae, which were freshly isolated from their vector (intermediate host), were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Within these 72 h of incubation the majority of larvae in negative control moult to fourth-stage larvae. Efficacy was determined as the reduction of motility in comparison to the negative control. Based on the evaluation of a wide concentration range, concentration-response curves as well as $EC_{50}$-values were calculated.

For the following examples, the EC50 was <0.1 ppm: 1, 2, 3, 4, 5, 6, 7, 8, 9, 10, 11, 12, 13, 14, 15, 16, 17, 18, 19, 20, 21, 22.

In Vitro Assay 6: *Cooperia curticei* (COOPCU)

Solvent: Dimethyl Sulfoxide

To produce a suitable preparation of active compound, 10 mg of active compound are dissolved in 0.5 ml solvent, and the concentrate is diluted with "Ringer's solution" to the desired concentration.

Approximately 40 nematode larvae (*Cooperia curticei*) are transferred into a test tube containing the compound solution.

After 5 days percentage of larval mortality is recorded. 100% efficacy means all larvae are killed; 0% efficacy means no larvae are killed.

In this test for example, the following compounds from the preparation examples showed good activity of 90% at an application rate of 20 ppm: 1.

In this test for example, the following compounds from the preparation examples showed good activity of 100% at an application rate of 4 ppm: 2.

In this test for example, the following compounds from the preparation examples showed good activity of 90% at an application rate of 4 ppm: 1.

In this test for example, the following compounds from the preparation examples showed good activity of 100% at an application rate of 0.8 ppm: 2.

In this test for example, the following compounds from the preparation examples showed good activity of 90% at an application rate of 0.8 ppm: 1.

In Vitro Assay 7: *Haemonchus contortus* (HAEMCO)

Solvent: Dimethyl Sulfoxide

To produce a suitable preparation of active compound, 10 mg of active compound are dissolved in 0.5 ml solvent, and the concentrate is diluted with "Ringer's solution" to the desired concentration.

Approximately 40 larvae of the red stomach worm (*Haemonchus contortus*) are transferred into a test tube containing compound solution.

After 5 days the percentage of larval mortality is recorded. 100% efficacy means all larvae are killed, 0% efficacy means no larvae are killed.

In this test for example, the following compounds from the preparation examples showed good activity of 90% at an application rate of 20 ppm: 2.

In this test for example, the following compounds from the preparation examples showed good activity of 80% at an application rate of 20 ppm: 1.

In this test for example, the following compounds from the preparation examples showed good activity of 90% at an application rate of 4 ppm: 2.

Formulation Example

Exemplary formulations consisted of the active substance in 10% Transcutol, 10% Cremophor EL and 80% isotonic saline solution. First the active substance was dissolved in Transcutol. After solution in Transcutol, Cremophor and isotonic saline solution were added. These formulations were used as service formulations in the following in vivo assay.

An example for a formulation according to the present invention is the following formulation Example F1. Therein, the active substance was dissolved in Transcutol to form a stock solution A. Then 0.100 mL of this stock solution A were taken and 0.100 mL Cremophor EL and 0.800 mL isotonic saline solution were added. The resulting liquid formulation (formulation example F1) had a volume of 1 mL.

Stock Solution A:

4.0 mg compound of example 2.

0.100 mL Transcutol.

Formulation Example F1

0.100 mL stock solution A, 0.100 mL Cremophor EL, and 0.800 mL isotonic saline solution.

In Vivo Assay

*Haemonchus contortus/Trichostrongylus colubriformis*/Gerbil

Gerbils, experimentally infected with *Haemonchus* and/or *Trichostrongylus*, were treated once during late prepatency. Test compounds were formulated as solutions or suspensions and applied orally or intraperitoneally. For both applications the same service formulation was used. The volume of the application amounted to normally 20 ml/kg at a maximum. By way of example, a gerbil with 40 g body weight was treated with 0.200 mL of the formulation of formulation example F1. This corresponded to a treatment with 20 mg/kg body weight.

Efficacy was determined per group as reduction of worm count in stomach and small intestine, respectively, after necropsy compared to worm count in an infected and placebo-treated control group.

The following examples were tested and had an activity of ≥70% or higher at the given treatment:

| Treatment | *Haemonchus contortus* | *Trichostrongylus colubriformis* |
|---|---|---|
| ≤0.3 mg/kg intraperitoneally | Expl N° 2 | |

The following examples were tested and had an activity of ≥80% or higher at the given treatment:

| Treatment | *Haemonchus contortus* | *Trichostrongylus colubriformis* |
|---|---|---|
| ≤10 mg/kg intraperitoneally | Expl N° 2; 3; 4 | Expl N° 4 |

The invention claimed is:

1. A compound of general formula (I):

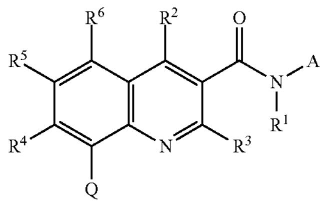

(I)

wherein

A is A1

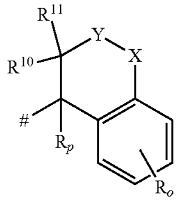

A1 is 0,1, 2, 3, or 4,

R is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R_p$ is selected from the group consisting of hydrogen and $C_1$-$C_4$-alkyl, X is O, Y is $CR^7R^8$, $R^1$ is selected from the group consisting of hydrogen, $C_1$-$C_4$-alkyl, $C_1$-$C_4$-halogenoalkyl having 1 to 5 halogen atoms, $C_3$-$C_6$-cycloalkyl, $C_3$-$C_6$-halogenocycloalkyl having 1 to 5 halogen atoms, —$NH_2$, —NH—$C_1$-$C_4$-alkyl, and —N($C_1$-$C_4$-alkyl)$_2$, $R^2$ is selected from the group consisting of tetrahydro-2H-pyran-4-yl, 3,6 dihydro-2H-pyran-4-yl, and 3-fluoroazetidin-1-yl, $R^3$ is hydrogen or $C_1$-$C_4$-alkyl, $R^4$ is selected from the group consisting of hydrogen, halogen, and $C_1$-$C_4$-alkoxy, $R^5$ is selected from the group consisting of hydrogen, halogen, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^6$ is selected from the group consisting of hydrogen, halogen, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^7$ is selected from the group consisting of hydrogen, fluorine, and $C_1$-$C_4$-alkyl, $R^8$ is selected from the group consisting of hydrogen, fluorine, and $C_1$-$C_4$-alkyl, $R^{10}$ is selected from the group consisting of hydrogen, —OH, $C_1$-$C_4$-alkyl, and $C_1$-$C_4$-alkoxy, $R^{11}$ is selected from the group consisting of hydrogen, $C_1$-$C_4$-alkyl, and $C_1$-$C_4$-alkoxy, Q is 2,3,5-trifluorophenyl, or a stereoisomer, a tautomer, an N-oxide, a hydrate, a solvate, or a salt thereof, or a mixture of same.

2. The compound according to claim 1, wherein:

A is A1

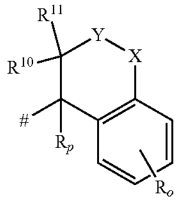

A1 is 0, 1, or 2,

R is selected from the group consisting of hydrogen, halogen, methyl, methoxy, and cyano, $R_p$ is hydrogen, X is O, Y is $CR^7R^8$, $R^1$ is selected from the group consisting of hydrogen, —OH, $C_1$-$C_4$-alkyl, and $C_1$-$C_4$-halogenoalkyl having 1 to 5 halogen atoms, $C_3$-$C_6$-cycloalkyl, $C_3$-$C_6$-halogenocycloalkyl having 1 to 5 halogen atoms, —$NH_2$, —NH—$C_1$-$C_4$-alkyl, and —N($C_1$-$C_4$-alkyl)$_2$, $R^2$ is selected from the group consisting of tetrahydro-2H-pyran-4-yl, 3,6 dihydro-2H-pyran-4-yl, and 3-fluoroazetidin-1-yl, $R^3$ is hydrogen or $C_1$-$C_4$-alkyl, $R^4$ is selected from the group consisting of hydrogen, halogen, and $C_1$-$C_4$-alkoxy, $R^5$ is selected from the group consisting of hydrogen, halogen, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^6$ is selected from the group consisting of hydrogen, halogen, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^7$ is hydrogen, $R^8$ is hydrogen, $R^{10}$ is selected from the group consisting of hydrogen and $C_1$-$C_4$-alkyl, $R^{11}$ is selected from the group consisting of hydrogen and $C_1$-$C_4$-alkyl, Q is 2,3,5-trifluorophenyl, or a stereoisomer, a tautomer, an N-oxide, a hydrate, a solvate, or a salt thereof, or a mixture of same.

3. The compound according to claim 1, wherein:

A is A1

A1

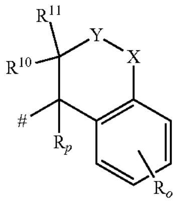

is 0, 1, or 2,

R is selected from the group consisting of hydrogen, fluorine, chlorine, bromine, methyl, methoxy, and cyano, $R_p$ is hydrogen, X is O, Y is $CR^7R^8$, $R^1$ is selected from the group consisting of hydrogen, $C_1$-$C_4$-alkyl, $C_1$-$C_4$-halogenoalkyl having 1 to 5 halogen atoms, $C_3$-$C_6$-cycloalkyl, $C_3$-$C_6$-halogenocycloalkyl having 1 to 5 halogen atoms, —$NH_2$, —NH—$C_1$-$C_4$-alkyl, and —N($C_1$-$C_4$-alkyl)$_2$, $R^2$ is selected from the group consisting of tetrahydro-2H-pyran-4-yl, 3,6 dihydro-2H-pyran-4-yl, and 3-fluoroazetidin-1-yl, $R^3$ is hydrogen or $C_1$-$C_4$-alkyl, $R^4$ is selected from the group consisting of hydrogen, halogen, and $C_1$-$C_4$-alkoxy, $R^5$ is selected from the group consisting of hydrogen, halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^6$ is selected from the group consisting of hydrogen, halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^7$ is hydrogen, $R^8$ is hydrogen, $R^{10}$ is selected from the group consisting of hydrogen and methyl, $R^{11}$ is selected from the group consisting of hydrogen and methyl, Q is 2,3,5-trifluorophenyl, or a stereoisomer, a tautomer, an N-oxide, a hydrate, a solvate, or a salt thereof, or a mixture of same.

4. The compound according to claim 1, wherein:

A is selected from the group consisting of

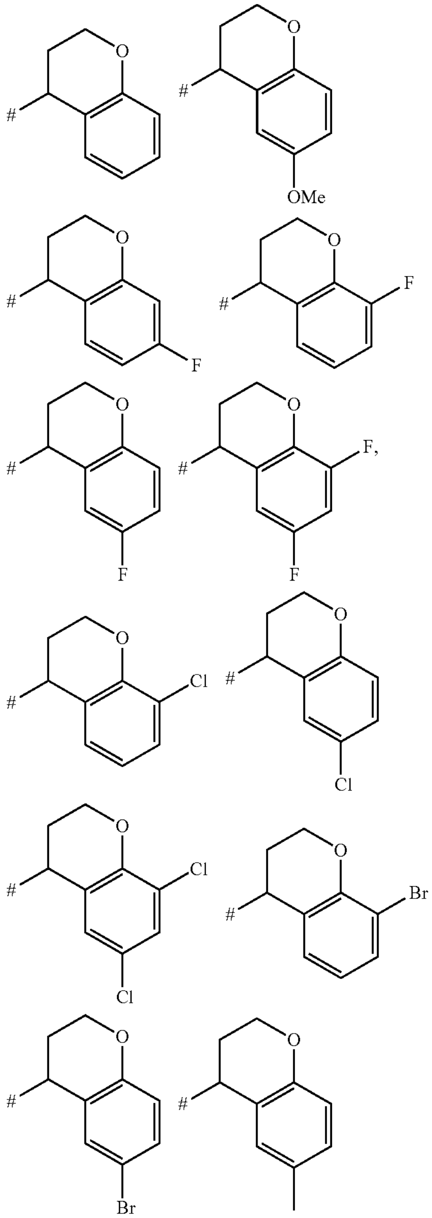

-continued

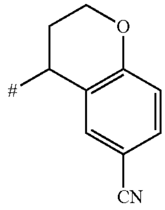,
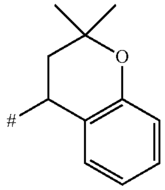
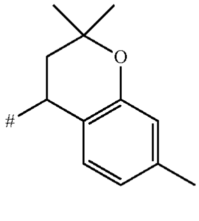
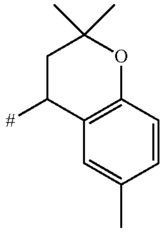
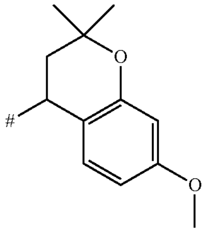
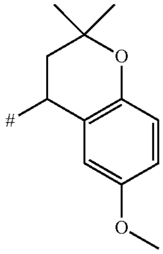,
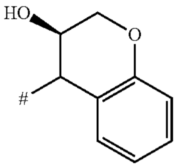
and
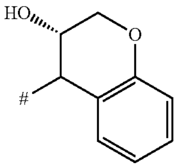, $R^1$ is selected from the group consisting of hydrogen, $C_1$-$C_4$-alkyl, $C_1$-$C_4$-halogenoalkyl having 1 to 5 halogen atoms, $C_3$-$C_6$-cycloalkyl, $C_3$-$C_6$-halogenocycloalkyl having 1 to 5 halogen atoms, —$NH_2$, —NH—$C_1$-$C_4$-alkyl, and —N($C_1$-$C_4$-alkyl)$_2$, $R^2$ is selected from the group consisting of tetrahydro-2H-pyran-4-yl, 3,6 dihydro-2H-pyran-4-yl, and 3-fluoroazetidin-1-yl, $R^3$ is hydrogen or $C_1$-$C_4$-alkyl, $R^4$ is selected from the group consisting of hydrogen, halogen, and $C_1$-$C_4$-alkoxy, $R^5$ is selected from the group consisting of hydrogen, halogen, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^6$ is selected from the group consisting of hydrogen, halogen, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, Q is 2,3,5-trifluorophenyl, or a stereoisomer, a tautomer, an N-oxide, a hydrate, a solvate, or a salt thereof, or a mixture of same.

5. The compound according to claim 1, wherein:

A is selected from the group consisting of

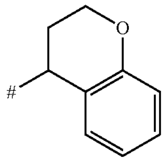
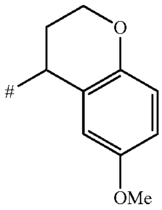
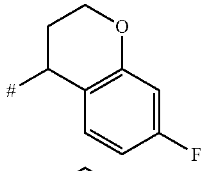
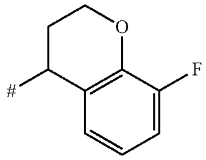
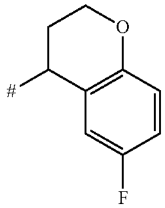
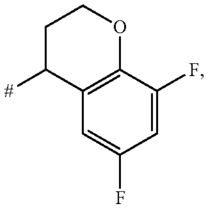
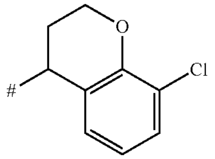
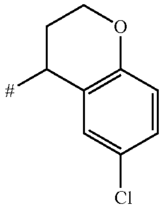
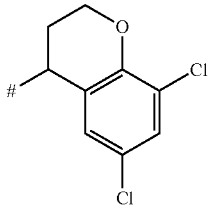
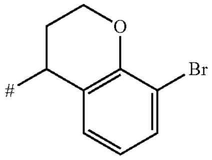
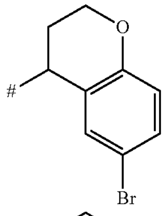
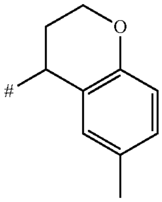
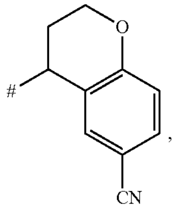,
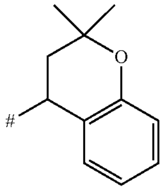
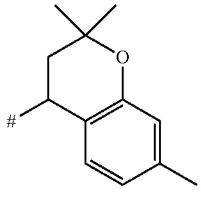
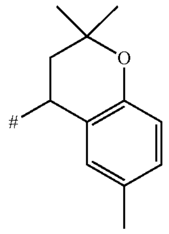

-continued

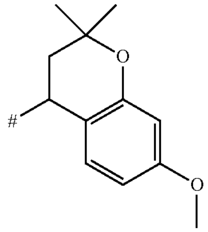

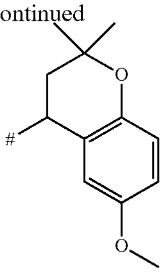

,

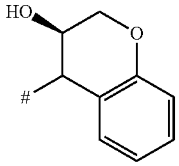

and

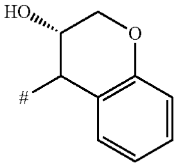

, $R^1$ is selected from the group consisting of hydrogen, $C_1$-$C_4$-alkyl, $C_1$-$C_4$-halogenoalkyl having 1 to 5 halogen atoms, $C_3$-$C_6$-cycloalkyl, $C_3$-$C_6$-halogenocycloalkyl having 1 to 5 halogen atoms, —$NH_2$, —NH—$C_1$-$C_4$-alkyl, and —N($C_1$-$C_4$-alkyl)$_2$, $R^2$ is selected from the group consisting of tetrahydro-2H-pyran-4-yl, 3,6 dihydro-2H-pyran-4-yl, and 3-fluoroazetidin-1-yl, $R^3$ is hydrogen or $C_1$-$C_4$-alkyl, $R^4$ is selected from the group consisting of hydrogen, halogen, and $C_1$-$C_4$-alkoxy, $R^5$ is selected from the group consisting of hydrogen, halogen, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms $R^6$ is selected from the group consisting of hydrogen, halogen, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms Q is 2,3,5-trifluorophenyl, or a stereoisomer, a tautomer, an N-oxide, a hydrate, a solvate, or a salt thereof, or a mixture of same.

6. The compound according to claim 1, wherein:

A1 is

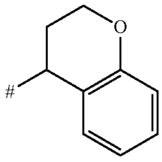

$R^1$ is selected from the group consisting of hydrogen, $C_1$-$C_4$-alkyl, $C_1$-$C_4$-halogenoalkyl having 1 to 5 halogen atoms, $C_3$-$C_6$-cycloalkyl, $C_3$-$C_6$-halogenocycloalkyl having 1 to 5 halogen atoms, —$NH_2$, —NH—$C_1$-$C_4$-alkyl, and —N($C_1$-$C_4$-alkyl)$_2$ $R^2$ is selected from the group consisting of tetrahydro-2H-pyran-4-yl, 3,6 dihydro-2H-pyran-4-yl, and 3-fluoroazetidin-1-yl, $R^3$ is hydrogen or $C_1$-$C_4$-alkyl, $R^4$ is selected from the group consisting of hydrogen, halogen, and $C_1$-$C_4$-alkoxy, $R^5$ is selected from the group consisting of hydrogen, halogen, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^6$ is selected from the group consisting of hydrogen, halogen, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, Q is 2,3,5-trifluorophenyl, or a stereoisomer, a tautomer, an N-oxide, a hydrate, a solvate, or a salt thereof, or a mixture of same.

7. The compound according to claim 1, wherein:

A1 is

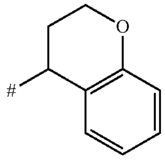

$R^1$ is selected from the group consisting of hydrogen, —OH, methyl, trifluoromethyl, cyclopropyl, —$NH_2$, methylamine, and dimethylamine, $R^2$ is selected from the group consisting of tetrahydro-2H-pyran-4-yl, 3,6 dihydro-2H-pyran-4-yl, and 3-fluoroazetidin-1-yl, $R^3$ is selected from the group consisting of hydrogen, methyl, ethyl, n-propyl, isopropyl, n-butyl, and isobutyl, $R^4$ is selected from the group consisting of hydrogen, fluorine, chlorine, bromine, methoxy, ethoxy, propoxy, and isopropoxy, $R^5$ is selected from the group consisting of hydrogen, fluorine, chlorine, bromine, methyl, ethyl, n-propyl, isopropyl, n-butyl, sec-butyl, trifluoromethyl, 2,2,2-trifluoroethyl, methoxy, ethoxy, propoxy, isopropoxy, trifluoromethoxy, $R^6$ is selected from the group consisting of hydrogen, fluorine, chlorine, bromine, methyl, ethyl, n-propyl, isopropyl, n-butyl, sec-butyl, trifluoromethyl, 2,2,2-trifluoroethyl, methoxy, ethoxy, propoxy, isopropoxy, trifluoromethoxy, Q is 2,3,5-trifluorophenyl, or a stereoisomer, a tautomer, an N-oxide, a hydrate, a solvate, or a salt thereof, or a mixture of same.

8. The compound according to claim 1, wherein:

A1 is

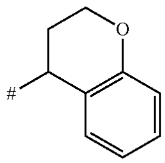

$R^1$ is hydrogen, $R^2$ is selected from the group consisting of tetrahydro-2H-pyran-4-yl, 3,6 dihydro-2H-pyran-4-yl, and 3-fluoroazetidin-1-yl, $R^3$ is hydrogen, $R^4$ is selected from the group consisting of hydrogen, halogen, and $C_1$-$C_4$-alkoxy, $R^5$ is hydrogen, $R^6$ is hydrogen, Q is 2,3,5-trifluorophenyl, or a stereoisomer, a tautomer, an N-oxide, a hydrate, a solvate, or a salt thereof, or a mixture of same.

9. The compound according to claim 1, wherein:

A1 is

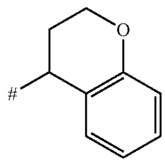

$R^1$ is hydrogen, $R^2$ is selected from the group consisting of tetrahydro-2H-pyran-4-yl, 3,6 dihydro-2H-pyran-4-yl, and 3-fluoroazetidin-1-yl, $R^3$ is hydrogen, $R^4$ is selected from the group consisting of hydrogen, fluorine, chlorine, methoxy, and isopropoxy, $R^5$ is hydrogen, $R^6$ is hydrogen, Q is 2,3,5-trifluorophenyl, or a stereoisomer, a tautomer, an N-oxide, a hydrate, a solvate, or a salt thereof, or a mixture of same.

10. The compound according to claim 1, wherein:

$R^1$ is hydrogen, $R^3$ is hydrogen, $R^4$ is selected from the group consisting of hydrogen, halogen, and $C_1$-$C_4$-alkoxy, $R^5$ is hydrogen, $R^6$ is hydrogen, or a stereoisomer, a tautomer, an N-oxide, a hydrate, a solvate, or a salt thereof, or a mixture of same.

11. The compound according to claim 1, wherein the compound is selected from the group consisting of:

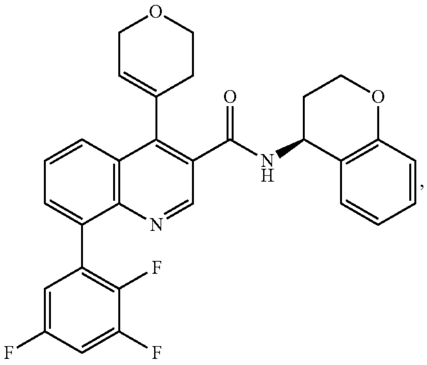,

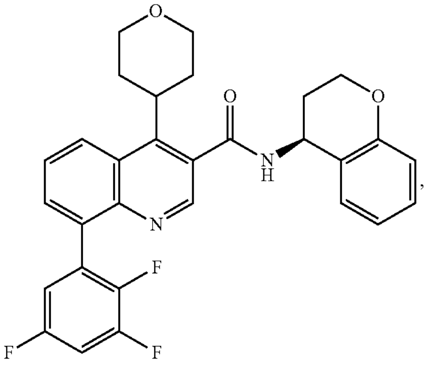,

-continued

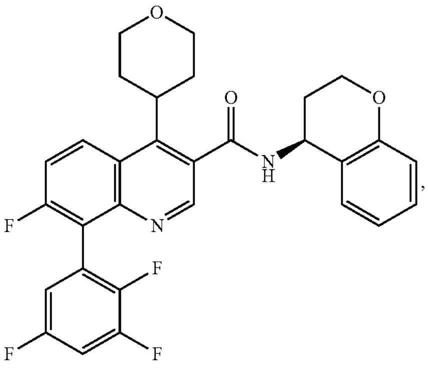,

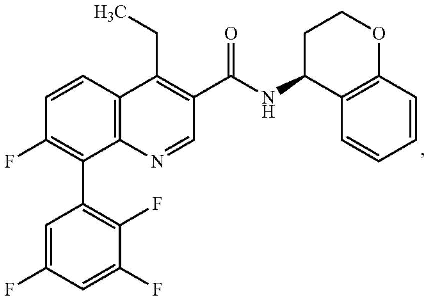,

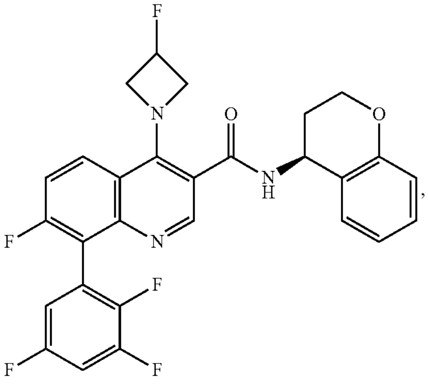,

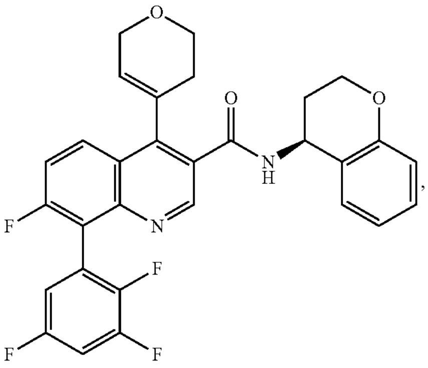, and

-continued

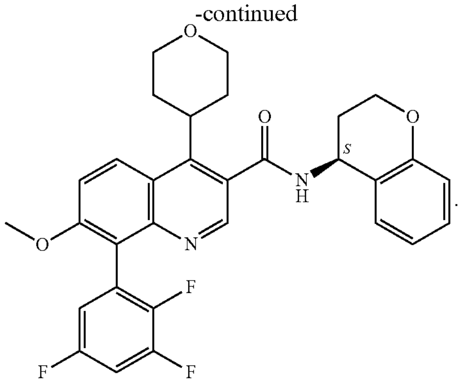

12. A method of preparing a compound of general formula (I) according to claim 1 said method comprising the step of allowing an intermediate compound of general formula 1N

1N

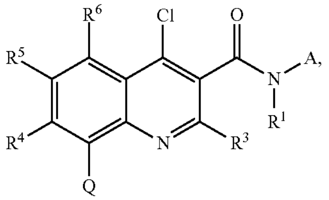

in which A, $R^1$, $R^3$, $R^4$, $R^5$, $R^6$, and Q are as defined for the compound of general formula (I) according to claim 1, to react with a compound of general formula 1F:

$R^2H$ 1F, in which $R^2$ is 3-fluoroazetidine, thereby giving a compound of general formula (I)

(I)

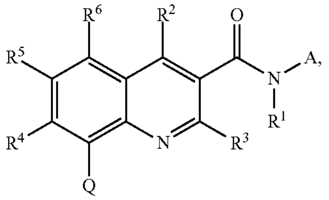

in which A, $R^1$, $R^3$, $R^4$, $R^5$, $R^6$, and Q are as defined for the compound of general formula (I) according to claim 1 and $R^2$ is 3-fluoroazetidine, or the step of allowing an intermediate compound of general formula 1T:

1T

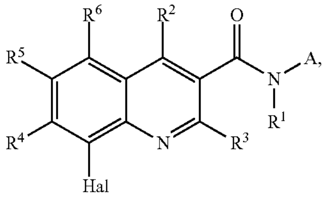

in which A, $R^1$, $R^2$, $R^3$, $R^4$, $R^5$ and $R^6$ are as defined for the compound of general formula (I) according to claim 1, and in which Hal is halogen, to react with a compound of general formula 1H $Q\text{-}B(OR)_2$ 1H, in which Q is 2,3,5-trifluorophenyl, and each R may be individually H or Me or both R are pinacolate, thereby giving a compound of general formula (I)

(I)

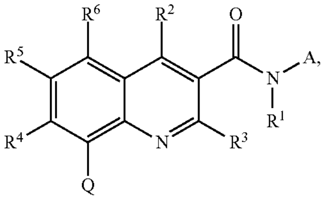

in which A, $R^1$, $R^2$, $R^3$, $R^4$, $R^5$, $R^6$, and Q are as defined for the compound of general formula (I) according to claim 1, or the step of allowing an intermediate compound of general formula 1W:

1W

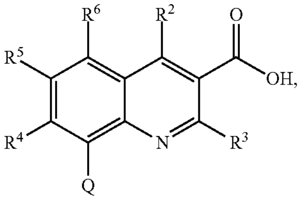

in which Q, $R^2$, $R^3$, $R^4$, $R^5$ and $R^6$ are as defined for the compound of general formula (I) according to claim 1, to react with a compound of general formula 1M

1M

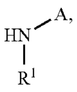

in which $R^1$ and A are as defined for the compound of general formula (I) according to claim 1, thereby giving a compound of general formula (I)

(I)

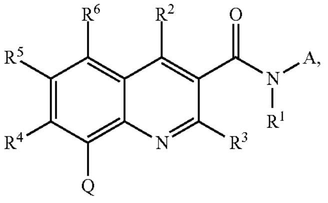

in which A, $R^1$, $R^2$, $R^3$, $R^4$, $R^5$, $R^6$, and Q are as defined for the compound of general formula (I) according to claim 1, or the step of allowing an intermediate compound of general formula 1N

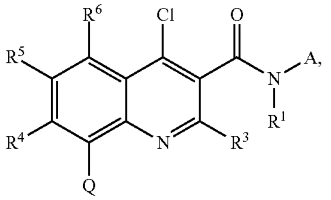
1N in which Q, A, $R^1$, $R^3$, $R^4$, $R^5$ and $R^6$ are as defined for the compound of general formula (I) according to claim 1, to react with a compound of general formula 2A:

$R^2$Met-X 2A, in which $R^2$ is 3,6-dihydro-2H-pyran-4-yl,

Met is magnesium or zinc, and X is chlorine, bromine or iodine, thereby giving a compound of general formula (I)

(I)
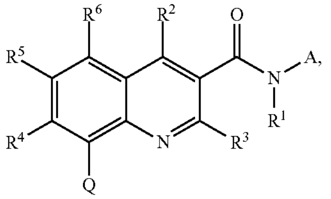

in which A, $R^1$, $R^3$, $R^4$, $R^5$, $R^6$, and Q are as defined for the compound of general formula (I) according to claim 1 and $R^2$ is 3,6-dihydro-2H-pyran-4-yl.

13. A compound of general formula (II):

(II)
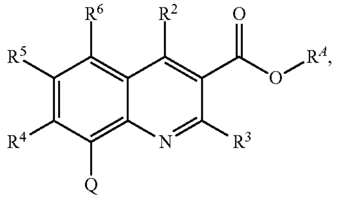

in which:

$R^2$ is —OH or as defined for the compound of general formula (I) according to any one of claims 1 to 10, $R^3$, $R^4$, $R^5$, $R^6$, and Q are as defined for the compound of general formula (I) according to any one of claims 1 to 10, and $R^{A}$ is H or $C_1$-$C_4$-alkyl, or a stereoisomer, a tautomer, an N-oxide, a hydrate, a solvate, or a salt thereof, or a mixture of same.

14. A pharmaceutical composition comprising a compound of general formula (I) according to claim 1 and one or more pharmaceutically acceptable excipients.

15. A method for control, treatment and/or prevention of a disease in humans and/or animals, comprising administering to a human or an animal in need thereof an amount of the compound of formula (I) according to claim 1, or a stereoisomer, a tautomer, an N-oxide, a hydrate, a solvate, or a salt thereof, or a mixture of the foregoing, wherein the disease is a helminthic infection.

16. A method for controlling helminth infections in humans and/or animals by administering an anthelminthically effective amount of at least one compound of formula (I) according to claim 1 to a human or an animal in need thereof.

17. A method for control, treatment and/or prevention of a disease in humans and/or animals, comprising administering to a human or an animal in need thereof a pharmaceutical composition according to claim 14, wherein the disease is a helminthic infection.

18. A method according to claim 12, wherein Hal in 1T is selected from the group consisting of chlorine, bromine and iodine.

* * * * *